United States Patent
Ge et al.

(10) Patent No.: US 10,456,405 B2
(45) Date of Patent: Oct. 29, 2019

(54) NITRIC OXIDE-RELEASING PRODRUG MOLECULE OF SUBSTITUTED QUINAZOLINES

(71) Applicants: ZHEJIANG HUAHAI PHARMACEUTICAL CO., LTD, Linhai (CN); SHANGHAI SYNERGY PHARMACEUTICAL SCIENCES CO., LTD, Shanghai (CN)

(72) Inventors: Jian Ge, Shanghai (CN); Yunfei Li, Shanghai (CN); Zhen Zhang, Shanghai (CN); Yijin Wang, Shanghai (CN); Jiamiao Wang, Shanghai (CN); Tao Cheng, Shanghai (CN)

(73) Assignees: ZHEJIANG HUAHAI PHARMACEUTICAL CO., LTD, Linhai (CN); SHANGHAI SYNERGY PHARMACEUTICAL SCIENCES CO., LTD, Shanghai (CN)

(*) Notice: Subject to any disclaimer, the term of this patent is extended or adjusted under 35 U.S.C. 154(b) by 0 days.

(21) Appl. No.: 15/756,476

(22) PCT Filed: Sep. 6, 2016

(86) PCT No.: PCT/CN2016/098217
§ 371 (c)(1),
(2) Date: Feb. 28, 2018

(87) PCT Pub. No.: WO2017/041701
PCT Pub. Date: Mar. 16, 2017

(65) Prior Publication Data
US 2018/0250305 A1  Sep. 6, 2018

(30) Foreign Application Priority Data

Sep. 7, 2015 (CN) .......................... 2015 1 0563200

(51) Int. Cl.
| | | |
|---|---|---|
| *A61K 31/517* | (2006.01) | |
| *C07D 239/88* | (2006.01) | |
| *A61K 31/5355* | (2006.01) | |
| *C07D 217/24* | (2006.01) | |
| *C07D 239/91* | (2006.01) | |
| *A61P 9/10* | (2006.01) | |
| *A61P 25/28* | (2006.01) | |
| *A61P 3/06* | (2006.01) | |
| *A61P 3/10* | (2006.01) | |
| *A61K 31/4418* | (2006.01) | |
| *A61K 31/519* | (2006.01) | |

(52) U.S. Cl.
CPC ...... *A61K 31/5355* (2013.01); *A61K 31/4418* (2013.01); *A61K 31/517* (2013.01); *A61K 31/519* (2013.01); *A61P 3/06* (2018.01); *A61P 3/10* (2018.01); *A61P 9/10* (2018.01); *A61P 25/28* (2018.01); *C07D 217/24* (2013.01); *C07D 239/91* (2013.01)

(58) Field of Classification Search
CPC ........................... A61K 31/517; C07D 239/88
USPC ....................................... 514/266.3; 544/287
See application file for complete search history.

(56) References Cited

U.S. PATENT DOCUMENTS

2015/0307650 A1   10/2015  Hammond et al.

FOREIGN PATENT DOCUMENTS

| | | | |
|---|---|---|---|
| CN | 101641339 | | 2/2010 |
| CN | 101768145 | | 7/2010 |
| CN | 102458405 | | 5/2012 |
| EP | 0984012 | | 8/1999 |
| EP | 1336602 | | 8/2003 |
| EP | 3348548 | * | 7/2018 |
| JP | 2007-504136 | | 3/2007 |
| JP | 2007-509842 | | 4/2007 |
| JP | 2008-528507 | | 7/2008 |
| JP | 2010-517946 | | 5/2010 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — Norton Rose Fulbright US LLP

(57) ABSTRACT

Provided are a compound of the formula below, and a pharmaceutically acceptable salt or stereoisomer thereof that can be used for treating cardiovascular diseases and compositions containing the compounds. The compounds, a pharmaceutically acceptable salt or stereoisomer thereof and the compositions can improve lipid metabolism disorders by increasing high-density lipoprotein cholesterol in blood; in addition, the compounds, a pharmaceutically acceptable salt or stereoisomer thereof and the compositions can also release nitric oxide, and reduce the onset risk of cardiovascular diseases by means of relaxing blood vessels, lowering blood pressure, inhibiting platelet adhesion and aggregation and maintaining vascular tension, and thus play an important role in preventing and treating the occurrence and development of cardiovascular diseases.

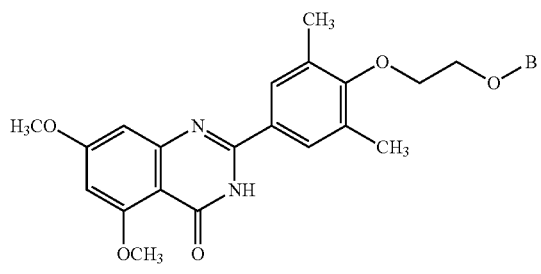

9 Claims, 1 Drawing Sheet

(56) References Cited

FOREIGN PATENT DOCUMENTS

| JP | 2012-524794 | 10/2012 |
| JP | 2013-010773 | 1/2013 |
| JP | 2013-512962 | 4/2013 |
| WO | WO 2001/049275 | 7/2001 |
| WO | WO 2004/105754 | 12/2004 |
| WO | WO 2005/011646 | 2/2005 |
| WO | WO 2005/032559 | 4/2005 |
| WO | WO 2006/045096 | 4/2006 |
| WO | WO 2008/092231 | 8/2008 |
| WO | WO 2009/158404 | 12/2009 |
| WO | WO 2010/123975 | 10/2010 |
| WO | WO 2014/113700 | 7/2014 |
| WO | WO 2015/109210 | 7/2015 |

OTHER PUBLICATIONS

Hackam, et al. JAMA, 296(14), 2006, 1731-1732.*
Search Report issued in International Application No. PCT/CN2016/098217, dated Nov. 28, 2016.
McLure et al., "RVX-208, an Inducer of ApoA-I in Humans, Is a BET Bromodomain Antagonist" *PloS One*, 2013,8(12):e83190.
Miller & Megson, "Recent developments in nitric oxide donor drugs" *British Journal of Pharmacology*, 2007, 151:305-321.
Switzer et al., "The emergence of nitroxyl (HNO) as a pharmacological agent" *Biochimica et Biophysica Acta*, 2009, 1787:835-840.
Extended European Search Report issued in corresponding European Patent Application No. 16843639, dated Feb. 28, 2019.
Office Action issued in Corresponding Japanese Patent Application No. 2018-530955, dated Feb. 5, 2019 (Machine Translation).

* cited by examiner

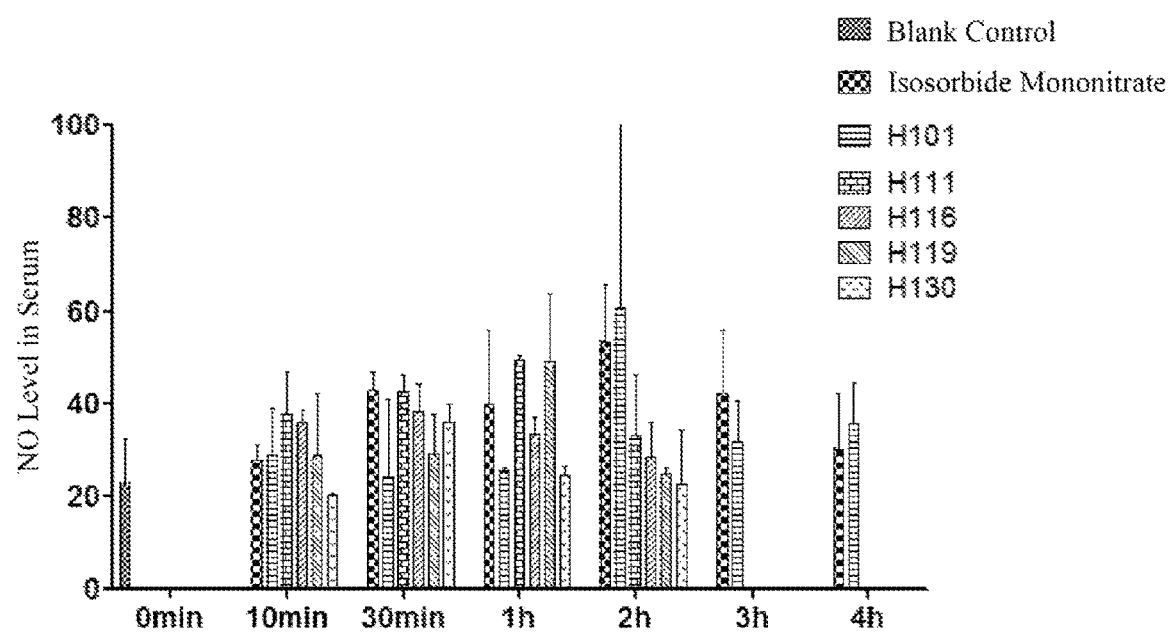

NITRIC OXIDE-RELEASING PRODRUG MOLECULE OF SUBSTITUTED QUINAZOLINES

CROSS-REFERENCE TO RELATED APPLICATIONS

The present application is a national phase under 35 U.S.C. § 371 of International Application No. PCT/CN2016/098217, filed Sep. 6, 2016, which claims the priority of Chinese Patent Application No. 201510563200.2, with the title of "Nitric Oxide-Releasing Prodrug Molecule", filed on Sep. 7, 2015, the entire contents of each of which are incorporated herein by reference.

FIELD OF THE INVENTION

The present invention belongs to the research and development field of pharmaceutical chemistry, in particular to a kind of nitric oxide-releasing prodrug molecules and their medicinal applications.

BACKGROUND OF THE INVENTION

Nitric oxide provider (NO Provider) is a kind of prodrugs that are capable of releasing NO in vivo. It refers to a drug that produces NO per se or by interacting with other substances, without catalyzed by nitric oxide synthase (NOS). It may act as a transportation form as well as a storage form of NO in vivo. It extends the half-life of NO, and overcomes inconveniences caused by inhaling NO and the disadvantage of difficulty in controlling the amount of the inhaled NO. NO provider-type drugs are prodrugs mainly made by binding a mother nucleus, which is the structure of known drugs or active compounds, to the NO provider through various linking groups. They can release the original drug and NO through relevant enzymatic or non-enzymatic action in vivo. Studies have shown that due to the effect of releasing NO, the efficacy of the NO provider-type drug is generally better than the original drug, and the adverse reaction is significantly less than the original drug.

At present, the trend of researching NO provider-type drugs is binding the NO provider to the effective drug by using the principle of the prodrug to form a new bound drug which is more effective. The advantages of this drug design manner consist in improving the bioavailability of the drugs, increasing the stability of the drugs, reducing toxic and side effects, and prolonging the efficacy of the drugs, etc. At the same time, it has the features of NO provider, and provides a biological activity depending on NO. The research on NO providers has become one of the hot spots and frontiers in the fields of biomedicine and pharmacy in recent years.

Cardiovascular diseases have been a worldwide public health concern. According to the statistics, about 3.5 million people die of cardiovascular diseases every year, i.e., one person die of cardiovascular diseases every 10 seconds. Fat metabolism or abnormal functioning in human body results in hyperlipidemia. Hyperlipidemia can directly induce some diseases that severely harm human health, such as atherosclerosis. Hyperlipidemia can cause insufficient blood supply to human tissues and organs, thereby inducing cardiovascular and cerebrovascular diseases such as coronary heart disease, cerebral stroke, hypertension, and renal failure. The mechanism of reverse cholesterol transport (RCT) in human body can ameliorate hyperlipidemia. RCT is a normal physiological process that can transport atherosclerotic plaques out of the arteries and eliminate it from the body through liver.

Apolipoprotein A-I (ApoA-I) is an important component of functional high density lipoprotein (HDL) particulates. ApoA-I can promote RCT, effectively eliminate atherosclerotic plaques, prevent and treat hyperlipidemia. On the other hand, ApoA-I can also activate phosphorylated acetyl coenzyme carboxylase by activating AMPK signal pathway, improve the absorption of glucose in muscle cells, and ameliorate blood glucose metabolism in vivo. With further researches, it is found that ApoA-I not only relates to the regulation of lipid and blood glucose metabolism in vivo, but also closely relates to immune function and neurological function. Clinical experimental data shows that a low level of ApoA-I in vivo can lead to increased incidences of cardiovascular diseases. Therefore, increasing the content of ApoA-I in human body will play an active role in preventing and treating cardiovascular diseases.

The development of small molecule compounds that increase the level of ApoA-I in vivo has become an important direction in the development of therapeutic drugs for cardiovascular diseases. This kind of small molecule compounds are disclosed in patents of WO 2006/045096, WO 2008/092231, and WO 2010/123975, etc.

BRIEF SUMMARY OF THE INVENTION

The compounds of the present invention are small molecule compounds, which can rapidly release NO and increase the level of ApoA-I in vivo once entering into the body. They can not only improve cardiovascular and cerebrovascular functions, but also have certain preventive and therapeutic effects on dyslipidemia and diabetic complications. The compounds provided by the present invention are the compounds represented by general formula (II), and the pharmaceutically acceptable salts or stereoisomers thereof:

A-B    (II)

wherein A is a residue group of a small molecule compound which is capable of preventing and treating cardiovascular diseases, selected from the following groups:

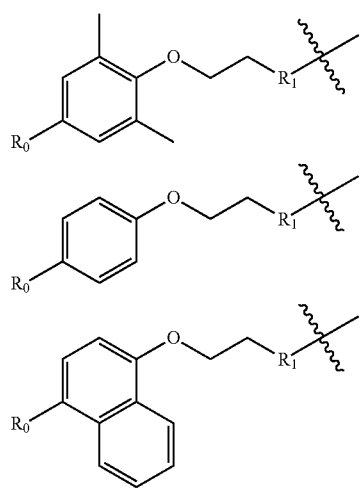

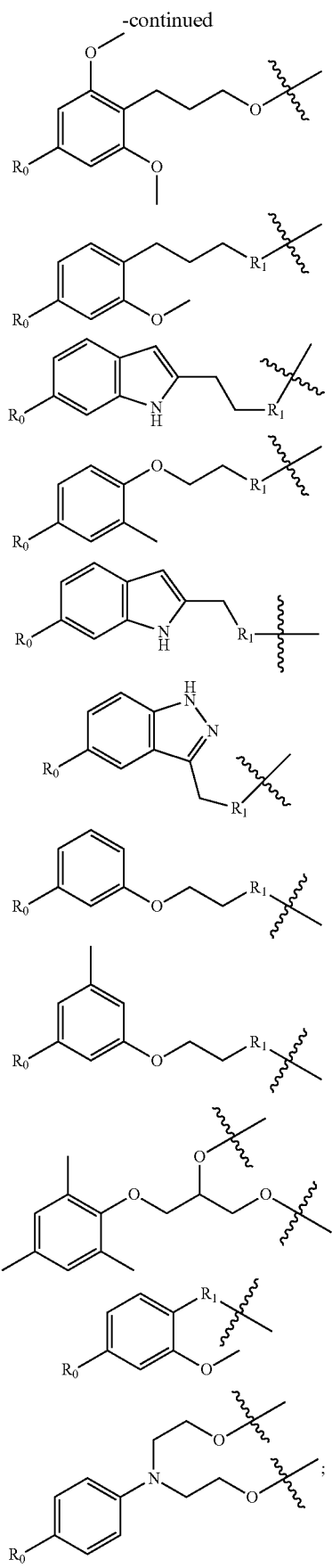
wherein $R_1$ is —O—; $R_0$ is selected from the following groups:
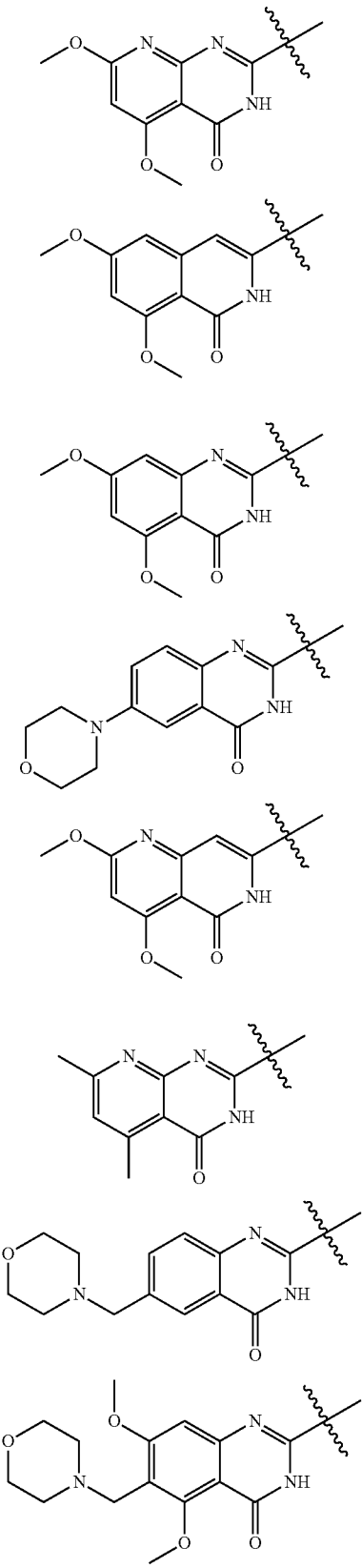

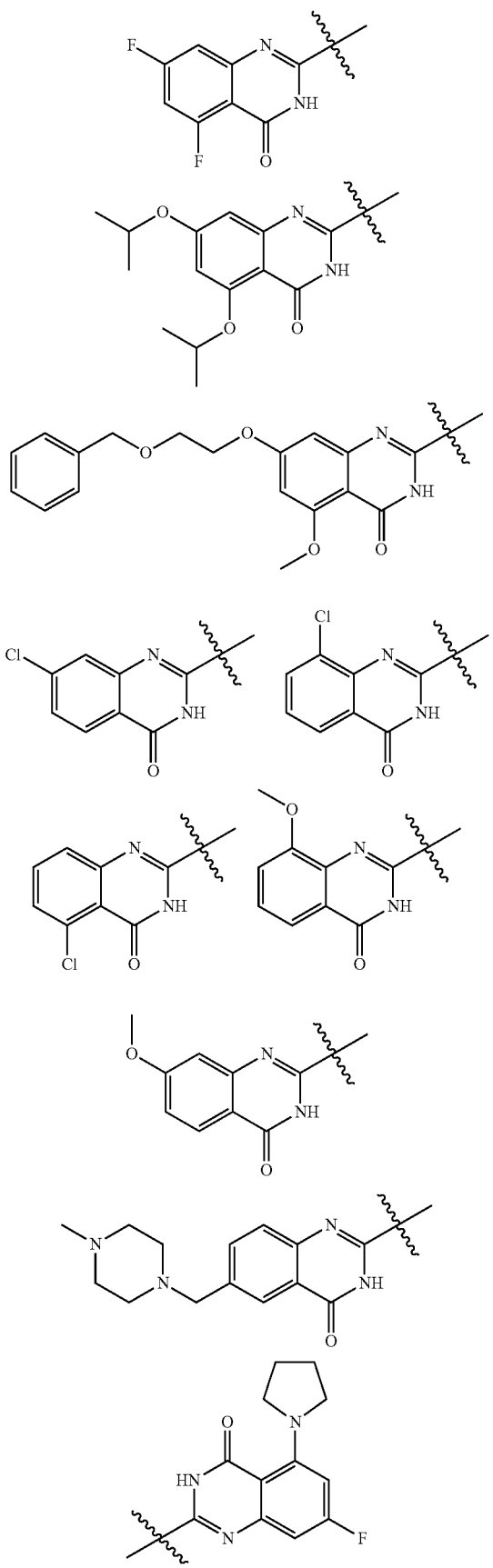
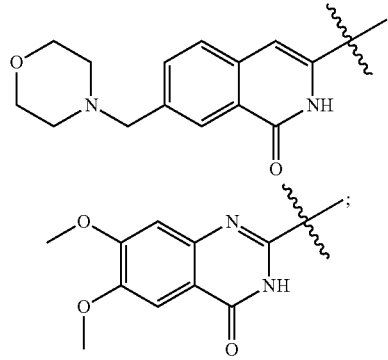
B is selected from:
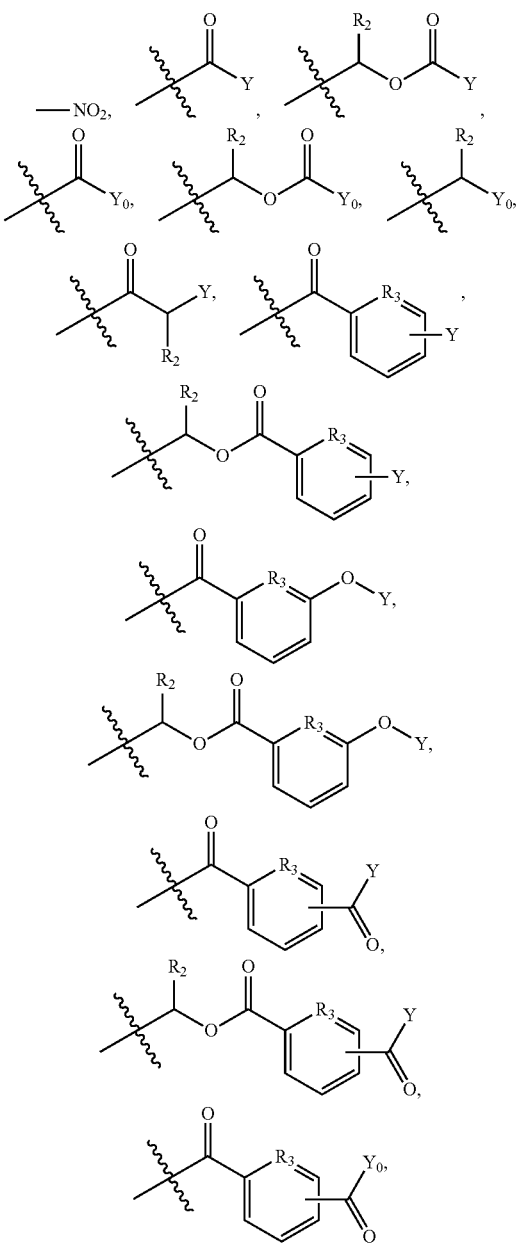

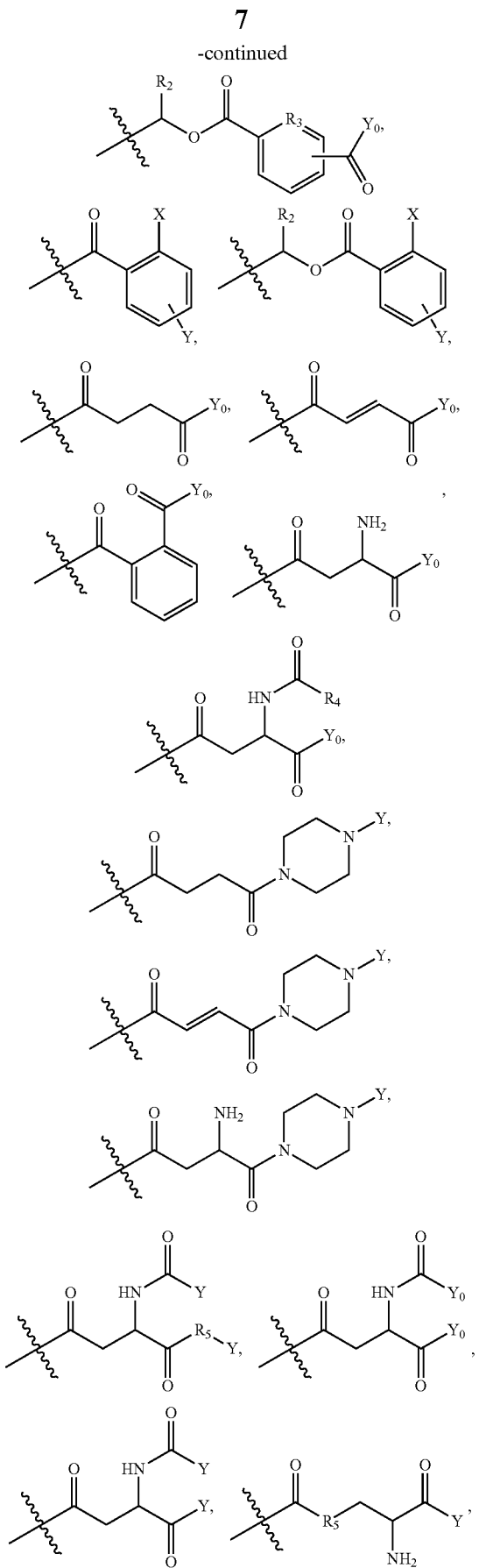
in addition to the structures listed above, B can be represented by the following general formulas:
—C(O)—CH$_2$—NH—C(O)—Y$_0$;
—C(O)—CH$_2$—NH—C(O)—Y;
—C(O)—CH$_2$—CH$_2$—NH—C(O)—Y$_0$;
—C(O)—CH$_2$—CH$_2$—NH—C(O)—Y;
in addition to the above general formulas, B also specifically refers to:

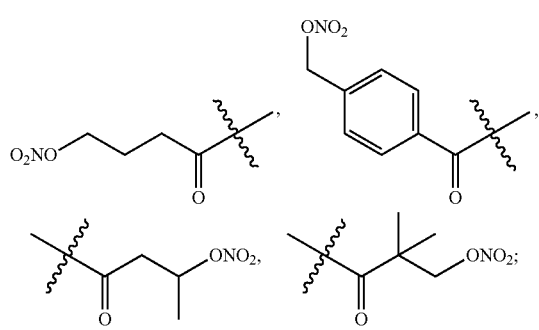

wherein, $R_2$ is H, a linear $C_{1-4}$ alkyl group, or a branched $C_{3-4}$ alkyl group;

$R_3$ is —CH— or a nitrogen atom;

X is a fluorine atom or a chlorine atom;

$R_4$ is a $C_{1-3}$ alkyl group;

$R_5$ is —O—, —S—, —NH—, or a nitrogen atom substituted with a $C_{1-3}$ alkyl group;

$R_7$ is

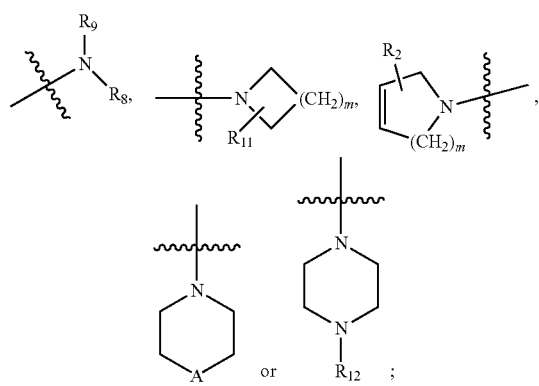

$R_8$ and $R_9$ are each independently $C_{1-6}$ alkyl group, $C_{1-6}$ alkyl group substituted with alkyl group, $C_{1-6}$ alkyl group substituted with hydroxyl group, $C_{1-6}$ alkyl group substituted with fluorine, $C_{1-6}$ alkyl group substituted with deuterium, —$CH_2$—$R_{10}$, or —$CH_2$—$CH_2$—$R_{10}$;

wherein $R_{10}$ is —OH, —O—$C_{1-6}$ alkyl group, —$OCD_3$, —C(O)-$T_2$, —C(O)—$R_5$-$T_2$, —OC(O)-$T_2$, —$R_5$—C(O)$R_5$-$T_2$, —$NH_2$, —$C_6H_5$, or an unsubstituted 5 or 6 membered heteroaryl ring having 1, 2 or 3 nitrogen atoms, or a substituted 5 or 6 membered heteroaryl ring having 1, 2 or 3 nitrogen atoms, wherein the substituted 5 or 6 membered heteroaryl ring is mono- or di-substituted on any carbon atom with a group selected from the following substituent groups:

—OH, —O—$C_{1-6}$ alkyl group, —$OCD_3$, —C(O)-$T_2$, —C(O)—$R_5$-$T_2$, —OC(O)-$T_2$, —$R_5$—C(O)$R_5$-$T_2$, —$NH_2$, —$C_{1-6}$ alkyl group, a $C_{1-6}$ alkyl group substituted with a hydroxyl group, a $C_{1-6}$ alkyl group substituted with fluorine, or a $C_{1-6}$ alkyl group substituted with deuterium;

$R_{11}$ is hydrogen, $C_{1-8}$ alkyl, a substituted $C_{1-8}$ alkyl group, phenyl group, aryl group, a substituted phenyl or aryl, or a cycloalkyl group having 4 to 7 carbon atoms; or a substituted cycloalkyl group having 4 to 7 carbon atoms, wherein the substituent group is defined as $T_2$ or $R_{10}$;

$R_{12}$ is $R_{11}$, —C(O)—$R_5$—$R_{11}$, or —C(O)—$R_{11}$, preferably —C(O)—$OCH_2CH_3$;

$R_{13}$ is H, $C_{1-4}$ alkyl, cyano, benzyl, nitro, p-nitrophenyl, alkylsulfonyl, arylsulfonyl, alkylcarbonyl, or cycloalkyl group;

$R_{14}$ is H,

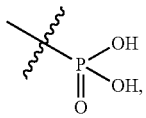 [SMILES: *P(=O)(O)O]

or $R_8$;

$Y_0$ is —$R_5$—Y,

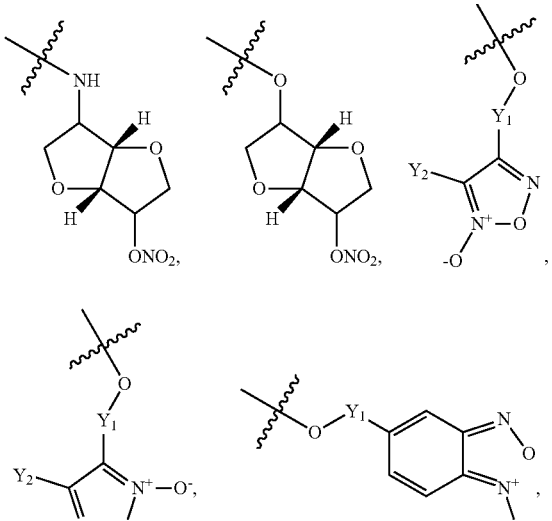

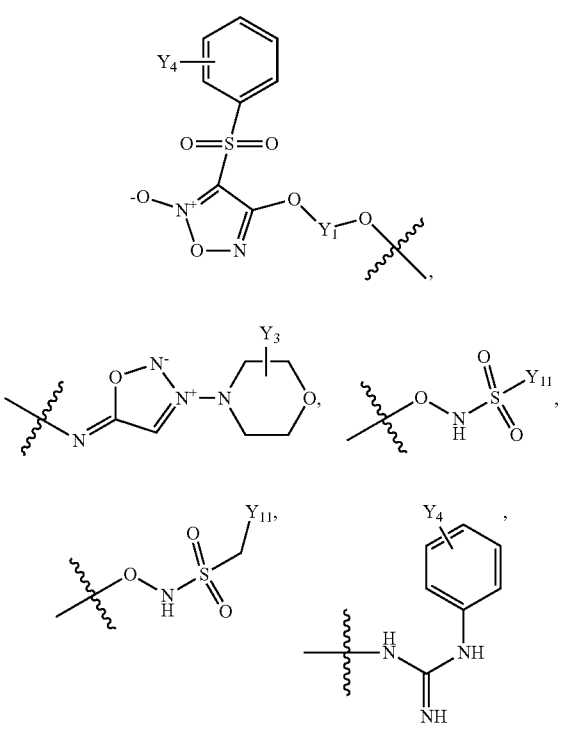

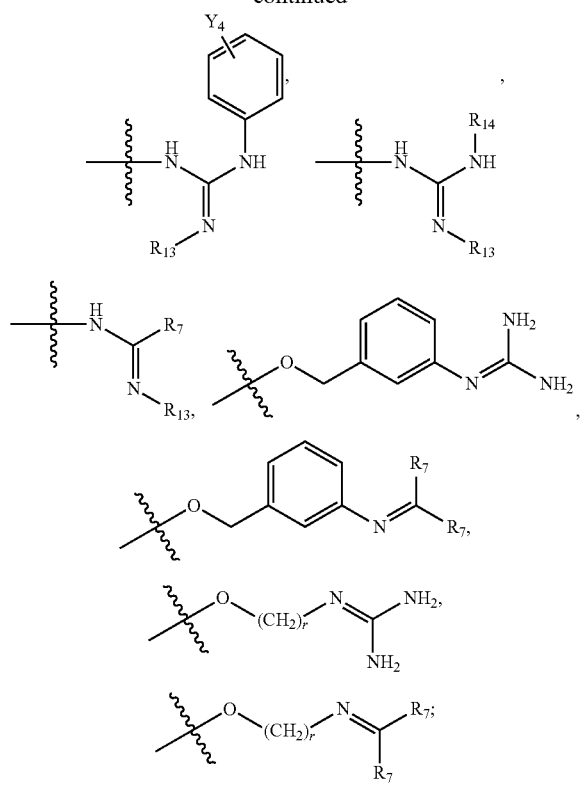
in addition to the above general formulas, Y₀ also specifically represents:
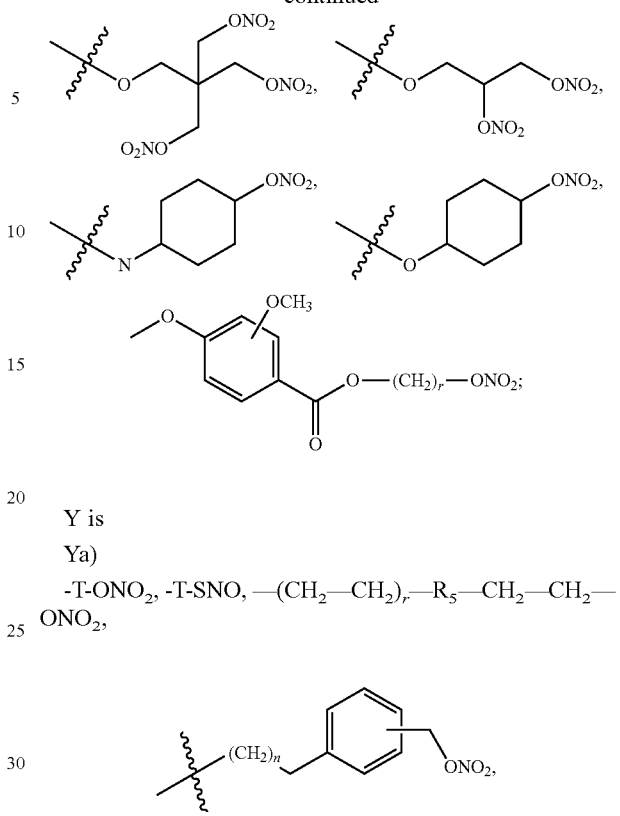
Y is
Ya)
-T-ONO₂, -T-SNO, —(CH₂—CH₂)ᵣ—R₅—CH₂—CH₂—ONO₂,
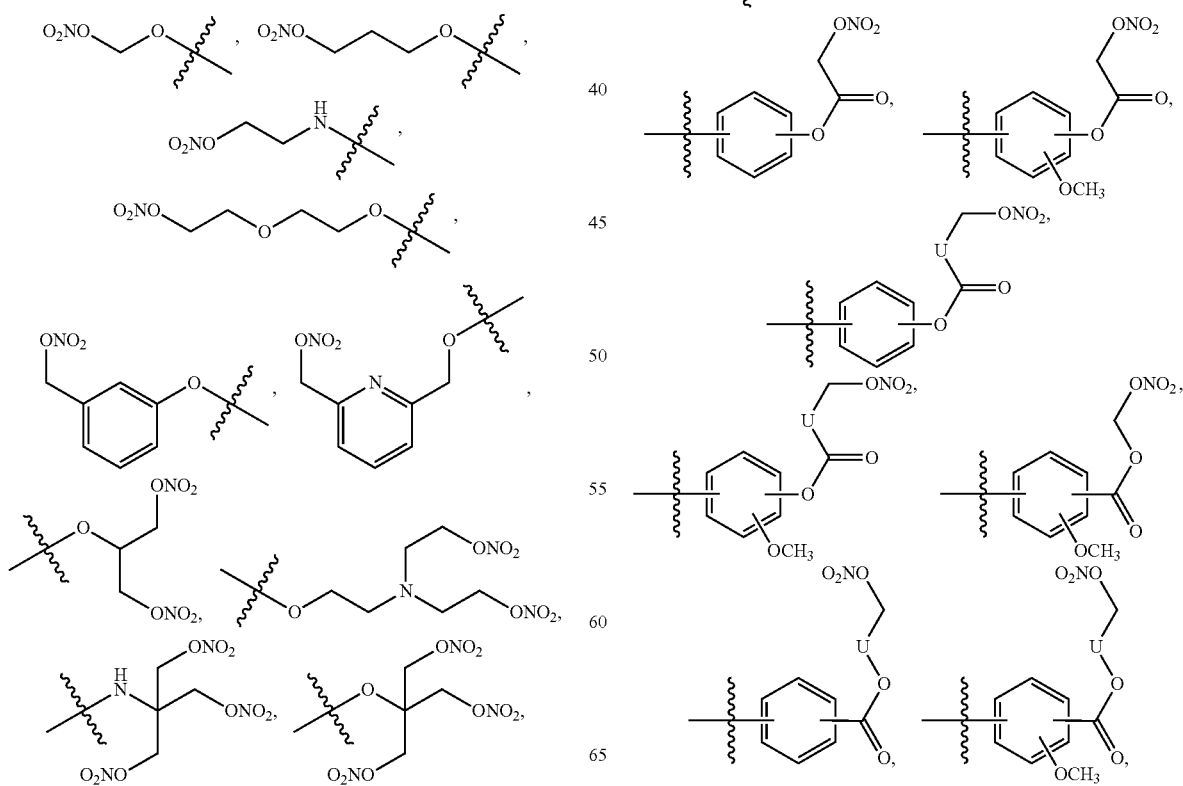

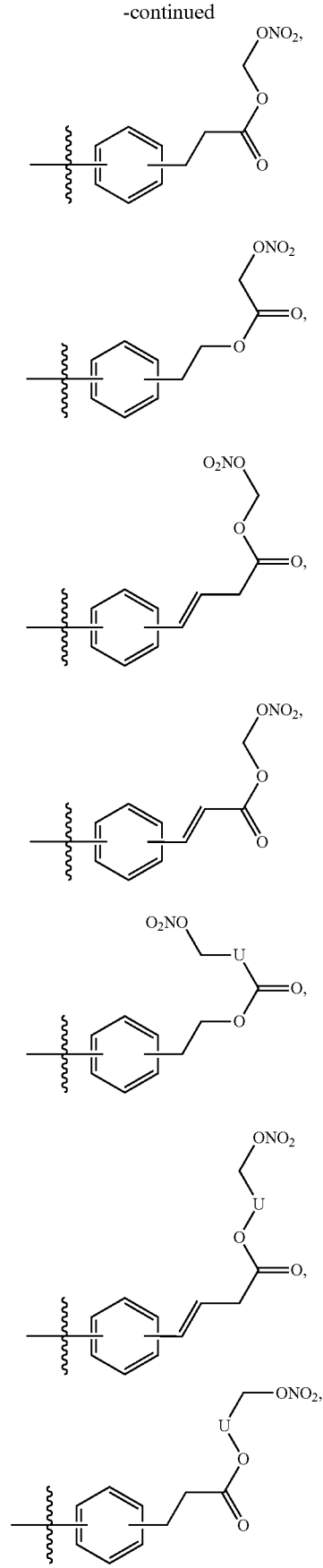
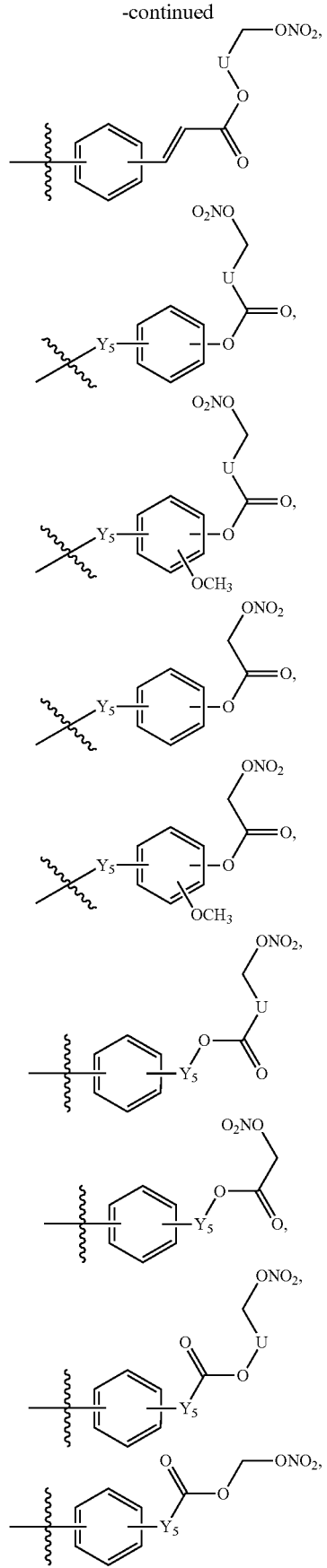

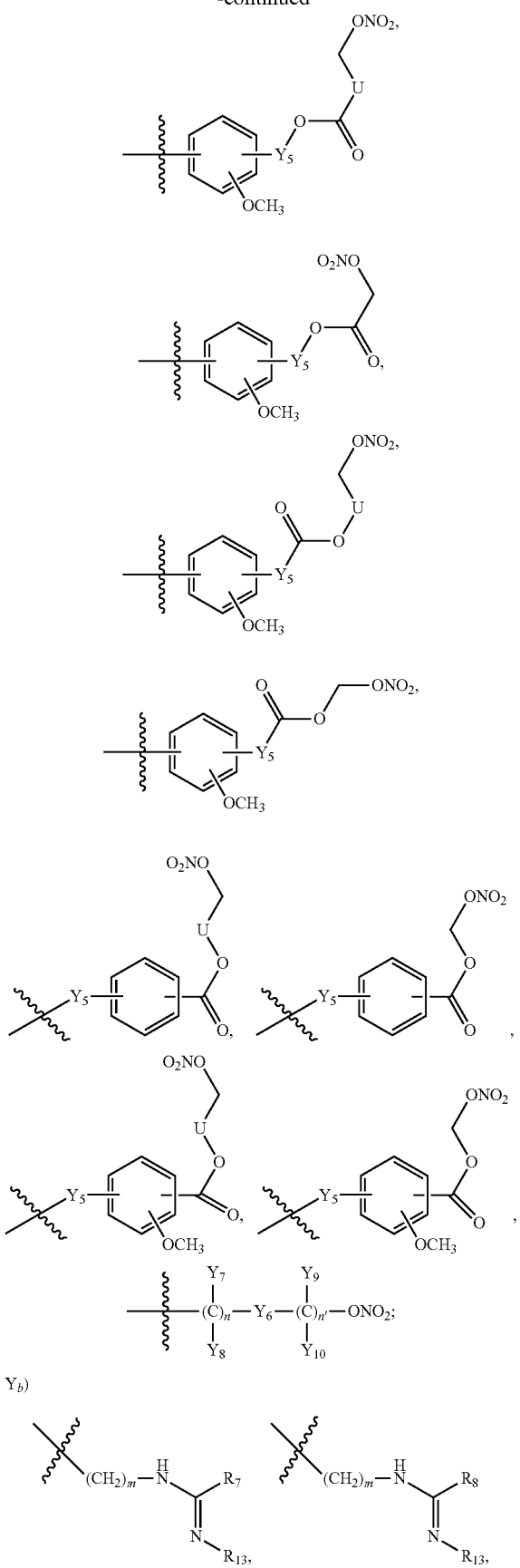
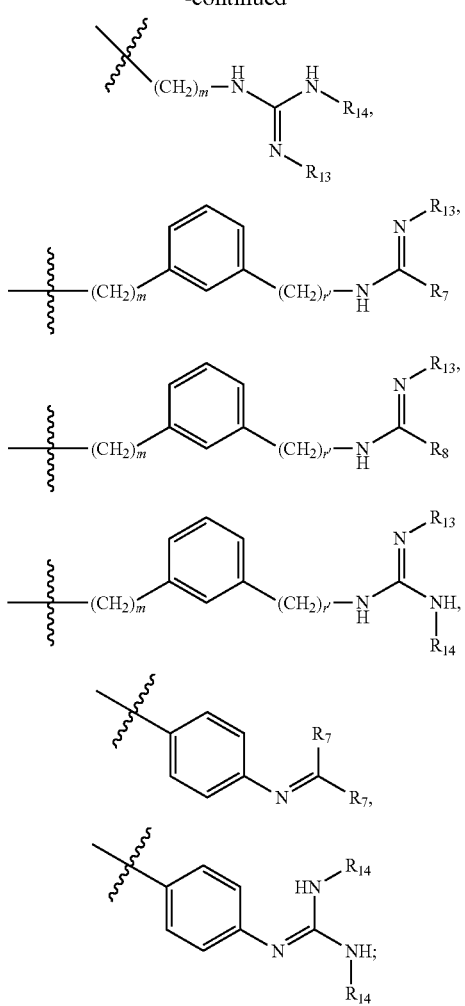
in addition to the above general formulas, Y further represents:
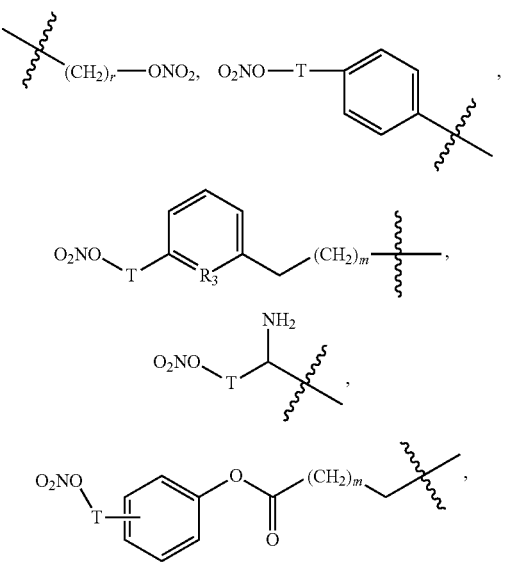

-continued

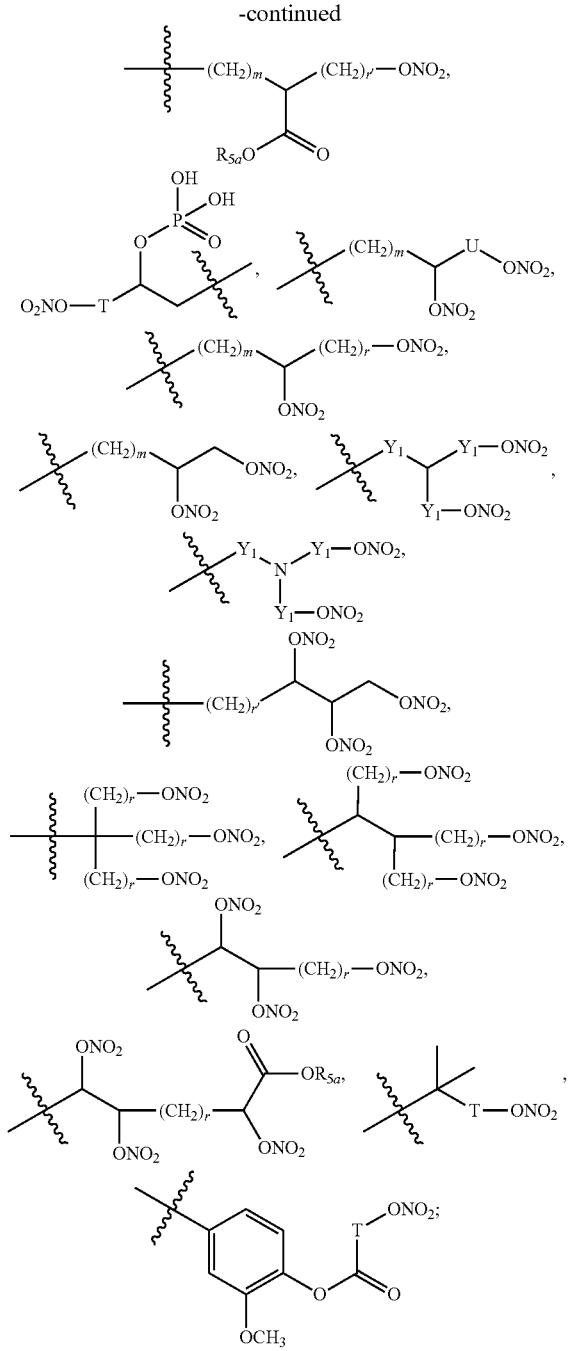

T is a linear $C_{1-20}$ alkylene group, a branched $C_{3-20}$ alkylene group, or a cycloalkylene group having 3 to 7 carbon atoms, the cycloalkylene group is optionally substituted with one or more linear $C_{1-10}$ alkyl chains or branched $C_{3-10}$ alkyl chains;

or a $C_{1-20}$ alkylene group substituted with one or more substituent groups, wherein the substituent group is hydroxyl group, nitrate group (—$ONO_2$), or $T_1$;

U is a linear $C_{1-20}$ alkylene group or a branched $C_{3-20}$ alkylene group optionally substituted with —$ONO_2$ group;

$Y_1$ is a linear $C_{1-20}$ alkylene group, a branched $C_{3-20}$ alkylene group, a linear $C_{2-20}$ alkenylene group, a branched $C_{3-20}$ alkenylene group;

or a $C_{1-20}$ alkylene group substituted with one or more substituent groups, or a $C_{2-20}$ alkenylene group substituted with one or more substituent groups, wherein the substituent group is $T_2$;

or a cycloalkylene group having 4 to 7 carbon atoms, and the cycloalkylene group is optionally substituted with one or more linear $C_{1-10}$ alkyl chains or branched $C_{3-10}$ alkyl chains; in particular, $Y_1$ is represented by the following general formulas:

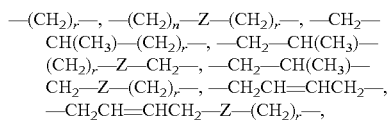

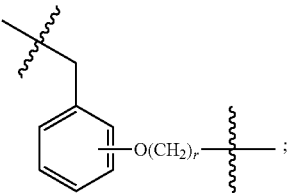

wherein Z is $R_5$,

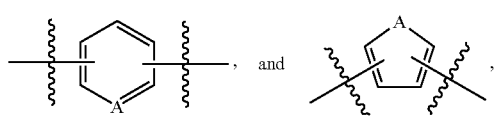

and A is O, N, S, C;

$T_1$ is an unsubstituted or substituted linear $C_{1-12}$ alkyl group, an unsubstituted or substituted branched $C_{3-12}$ alkyl group, an unsubstituted or substituted linear $C_{2-12}$ alkenyl group, an unsubstituted or substituted branched $C_{3-12}$ alkenyl group, an unsubstituted or substituted benzyl group, an unsubstituted or substituted phenyl group, a $C_{1-4}$ alkyl group substituted with an unsubstituted or substituted aryl group, an unsubstituted or substituted heteroaryl group, —OC(O)—($C_{1-10}$ alkyl)-$ONO_2$, or —O—($C_{1-10}$ alkyl)-$ONO_2$; $T_2$ is an unsubstituted or substituted linear $C_{1-12}$ alkyl group, an unsubstituted or substituted branched $C_{3-12}$ alkyl group, an unsubstituted or substituted linear $C_{2-12}$ alkenyl group, an unsubstituted or substituted branched $C_{3-12}$ alkenyl group, an unsubstituted or substituted benzyl group, an unsubstituted or substituted phenyl group, a $C_{1-4}$ alkyl group substituted with an unsubstituted or substituted aryl group, an unsubstituted or substituted heteroaryl group;

$Y_2$ is $C_{1-8}$ alkyl group, phenyl group, phenylsulfonyl, cyano, trifluoromethyl, $C_{1-8}$ alkoxy, or $C_{1-8}$ alkyl nitrate group;

$Y_3$ is H, F, Cl, Br, I, OH, $C_{1-6}$ alkyl group, —$OC_{1-6}$ alkyl group;

$Y_4$ is hydrogen, halogen, trifluoromethyl, $C_{1-8}$ alkoxy, $C_{1-8}$ alkyl, nitro, sulfonamido, amino, or cyano group;

$Y_5$ is —$CH_2$—$CH_2$—, —CH=CH—$CH_2$—, or —CH=CH—;

$Y_6$ is a saturated 5 or 6 membered aromatic heterocycle, an unsaturated 5 or 6 membered aromatic heterocycle, wherein the heterocycle comprises one or more heteroatoms selected from nitrogen, oxygen, and sulfur, specifically selected from:

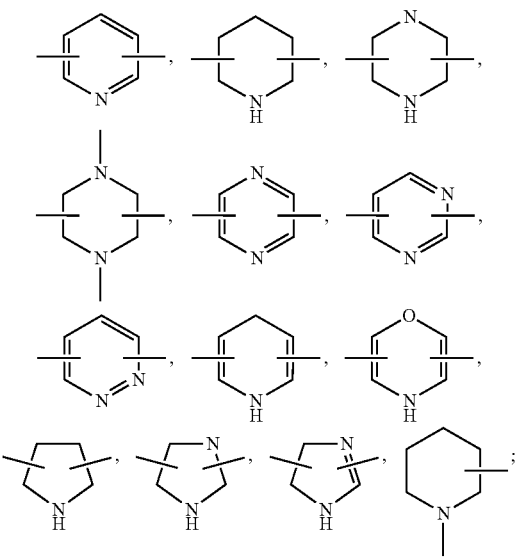

$Y_7$, $Y_8$, $Y_9$, and $Y_{10}$ are the same or different, and represent H, a linear $C_{1-4}$ alkyl group, or a branched $C_{3-5}$ alkyl group;

$Y_{11}$ is

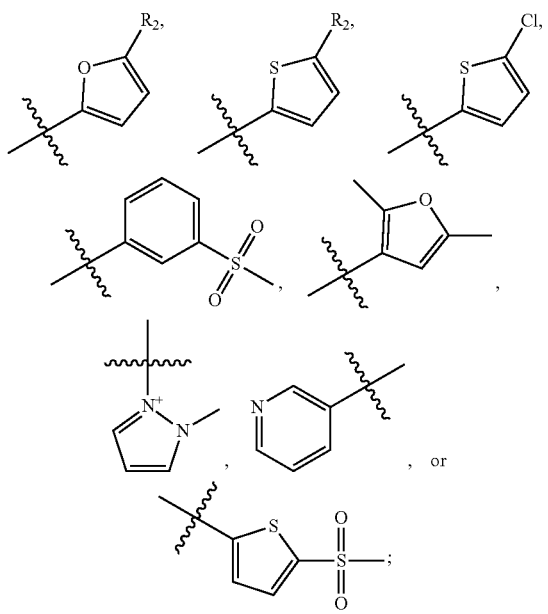

and n is an integer from 0 to 10; n' is an integer from 1 to 10; m is an integer from 0 to 3; m' is 1 or 2; r is an integer from 1 to 6; and r' is an integer from 0 to 6.

The term "alkyl group" comprises a saturated aliphatic group, including a linear alkyl group (such as methyl, ethyl, propyl, butyl, pentyl, hexyl, heptyl, octyl, nonyl, and decyl group, etc.), a branched alkyl group (such as isopropyl, t-butyl, and isobutyl, etc.), a cycloalkyl group (cyclopropyl, cyclopentyl, cyclohexyl, cycloheptyl, and cyclooctyl group), a cycloalkyl group substituted with an alkyl group, and an alkyl group substituted with a cycloalkyl group.

In some embodiments, the linear or branched alkyl group has 6 or less carbon atoms in the backbone (e.g., the linear chain is $C_{1-6}$, and the branched chain is $C_{3-6}$), and more preferably 4 or less carbon atoms. Likewise, the preferred cycloalkyl group has 3 to 8 carbon atoms in the cyclic structure thereof, and more preferably 5 or 6 carbons in the cyclic structure thereof.

The term "$C_{1-6}$ alkyl group" comprises an alkyl group containing 1 to 6 carbon atoms.

In addition, the term "alkyl group" also comprises "an unsubstituted alkyl group" and "a substituted alkyl group", the latter refers to an alkyl group in which the hydrogen on one or more carbon atoms in the hydrocarbon backbone is replaced by a substituent group. The substituent group can comprise alkenyl, alkynyl, halogen, hydroxy, alkylcarbonyloxy, arylcarbonyloxy, alkoxycarbonyloxy, aryloxycarbonyloxy, hydroxycarbonyl, alkylcarbonyl, arylcarbonyl, alkoxycarbonyl, aminocarbonyl, alkylaminocarbonyl, dialkylaminocarbonyl, alkylthiocarbonyl, alkoxy, phosphate, phosphorate, cyano, amino (including alkylamino, dialkylamino, arylamino, diarylamino, and alkylarylamino), acylamino (including alkylcarbonylamino, arylcarbonylamino, carbamoyl, and ureido), amidino, imino, mercapto, alkylthio, arylthio, hydroxythiocarbonyl, sulfate, alkylsulfinyl, sulfo, sulfamoyl, sulfonylamino, nitro, trifluoromethyl, cyano, azido, heterocyclyl, alkylaryl, or aromatic or heteroaromatic groups.

The term "aryl group" comprises 5 and 6 membered monocyclic aromatic groups, which can contain 0 to 4 heteroatoms, such as phenyl, pyrrolyl, furanyl, thienyl, thiazolyl, isothiazolyl, imidazolyl, triazolyl, tetrazolyl, pyrazolyl, oxazolyl, isoxazolyl, pyridinyl, pyrazinyl, pyridazinyl, and pyrimidinyl, etc. Furthermore, the term "aryl group" also comprises polycyclic aryl groups, such as tricyclic and bicyclic aryl groups, e.g., naphthyl, benzoxazolyl, benzodioxazolyl, benzothiazolyl, benzimidazolyl, benzothienyl, methylenedioxyphenyl, quinolyl, isoquinolyl, naphthyridinyl, indolyl, benzofuranyl, purinyl, deazapurinyl, or indolizinyl. These heteroatom-containing aryl groups are also referred to as "arylheterocyclic group", "heterocyclic group", "heteroaryl group", or "heteroaromatic group".

Typical heteroaryl groups comprise 2- or 3-thienyl; 2- or 3-furyl; 2- or 3-pyrrolyl; 2-, 4-, or 5-imidazolyl; 3-, 4-, or 5-pyrazolyl; 2-, 4-, or 5-thiazolyl; 3-, 4-, or 5-isothiazolyl; 2-, 4-, or 5-oxazolyl; 3-, 4-, or 5-isoxazolyl; 3- or 5-1,2,4-triazolyl; 4- or 5-1,2,3-triazolyl; tetrazolyl; 2-, 3-, or 4-pyridyl; 3- or 4-pyridazinyl; 3-, 4-, or 5-pyrazinyl; 2-pyrazinyl; 2-, 4-, or 5-pyrimidinyl.

The term "heteroaryl group" also refers to a group in which a heteroaromatic ring is fused to one or more rings of aryl, cycloaliphatic, or heterocyclyl groups, wherein the linking group or linking point is located on the heteroaromatic ring. Examples thereof include, but are not limited to, 1-, 2-, 3-, 5-, 6-, 7-, or 8-indolizinyl; 1-, 3-, 4-, 5-, 6-, or 7-isoindolyl; 2-, 3-, 4-, 5-, 6-, or 7-indolyl; 2-, 3-, 4-, 5-, 6-, or 7-indazolyl; 2-, 4-, 5-, 6-, 7-, or 8-purinyl; 1-, 2-, 3-, 4-, 6-, 7-, 8-, or 9-quinolizinyl; 2-, 3-, 4-5-, 6-, 7-, or 8-quinolyl; 1-, 3-, 4-, 5-, 6-, 7-, or 8-isoquinolyl; 1-, 4-, 5-, 6-, 7-, or 8-phthalazinyl; 2-, 3-, 4-, 5-, or 6-naphthyridinyl; 2-, 3-, 5-, 6-, 7-, or 8-quinazolinyl; 3-, 4-, 5-, 6-, 7-, or 8-cinnolinyl; 2-, 4-, 6-, or 7-pteridinyl; 1-, 2-, 3-, 4-, 5-, 6-, 7-, or 8-4aH carbazolyl; 1-, 2-, 3-, 4-, 5-, 6-, 7-, or 8-carbazolyl; 1-, 3-, 4-, 5-, 6-, 7-, 8-, or 9-carbolinyl; 1-, 2-, 3-, 4-, 6-, 7-, 8-, 9-, or 10-phenanthridinyl; 1-, 2-, 3-, 4-, 5-, 6-, 7-, 8-, or 9-acridinyl; 1-, 2-, 4-, 5-, 6-, 7-, 8-, or 9-pyridyl; 2-, 3-, 4-, 5-, 6-, 8-, 9- or 10-phenanthrolinyl; 1-, 2-, 3-, 4-, 6-, 7-, 8-, or 9-phenazinyl; 1-, 2-, 3-, 4-, 6-, 7-, 8-, 9-, or 10-phenothiazinyl; 1-, 2-, 3-, 4-, 6-, 7-, 8-, 9-, or 10-phenazinyl; 2-, 3-, 4-, 5-, 6-, or 1-, 3-, 4-, 5-, 6-, 7-, 8-, 9-, or 10-benzoisoquinolyl; 2-, 3-, 4-, or thieno [2,3-b] furanyl; 2-, 3-, 5-, 6-, 7-, 8-, 9-, 10-, or 11-7H-pyrazino [2,3-c] carbazolyl; 2-, 3-, 5-, 6-, or 7-2H-furo [3,2-b]-pyranyl; 2-, 3-, 4-, 5-, 7-, or 8-5H-pyridino [2,3-d]-o-oxazinyl; 1-, 3-, or 5-1H-pyrazolo [4,3-d]-oxazolyl; 2-, 4-, or 5-4H-imidazo [4,5-d] thiazolyl; 3-, 5-, or 8-pyrazino [2,3-d] pyridazinyl; 2-, 3-, 5-, or 6-imidazo [2,1-b] thiazolyl; 1-, 3-, 6-, 7-, 8-, or 9-furo [3,4-c] cinnolinyl; 1-, 2-, 3-, 4-, 5-, 6-, 8-, 9-, 10, or 11-4H-pyridino [2,3-c] carbazolyl; 2-, 3-, 6-, or 7-imidazo [1,2-b][1,2,4] triazinyl; 7-benzo [b] thienyl; 2-, 4-, 5-, 6-, or 7-benzoxazolyl; 2-, 4-, 5-, 6-, or 7-benzimidazolyl; 2-, 3-, 4-, 5-, 6-, or 7-benzothiazolyl; 1-, 2-, 4-, 5-, 6-, 7-, 8-, or 9-benzoxazolyl; 2-, 4-, 5-, 6-, 7-, or 8-benzoxazinyl; 1-, 2-, 3-, 5-, 6-, 7-, 8-, 9-, 10-, or 11-1H-pyrrolo [1,2-b][2] benzazepinyl. Typical fused heteroaryl groups comprise 2-, 3-, 4-, 5-, 6-, 7-, or 8-quinolyl; 1-, 3-, 4-, 5-, 6-, 7-, or 8-isoquinolyl; 2-, 3-, 4-, 5-, 6-, or 7-indolyl; 2-, 3-, 4-, 5-, 6-, or 7-benzo [b] thienyl; 2-, 4-, 5-, 6-, or 7-benzoxazolyl; 2-, 4-, 5-, 6-, or 7-benzimidazolyl; 2-, 4-, 5-, 6-, or 7-benzothiazolyl groups.

The aromatic ring of "aryl group" or "heteroaryl group" can be substituted at one or more sites of the ring with the substituent groups described above, for example, halogen, hydroxy, alkoxy, alkylcarbonyloxy, arylcarbonyloxy, alkoxycarbonyloxy, aryloxycarbonyloxy, hydroxycarbonyl, alkylcarbonyl, alkylaminocarbonyl, arylalkylaminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphorate, cyano, amino (including alkylamino, dialkylamino, arylamino, diarylamino, and alkylarylamino), acylamino (including alkylcarbonylamino, arylcarbonylamino, carbamoyl, and ureido), amidino, imino, mercapto, alkylthio, arylthio, hydroxythiocarbonyl, sulfate, alkylsulfinyl, sulfonate, sulfamoyl, sulfonylamino, nitro, trifluoromethyl, cyano, azido, heterocyclyl, alkylaryl, or aromatic or heteroaromatic group, wherein the aryl group can also be fused or bridged with non-aromatic alicyclic or heterocyclic groups to form polycyclic groups (e.g., tetrahydronaphthalene).

The term "alkenyl group" comprises an unsaturated aliphatic group which is analogous in length and possible substitutions to the alkyl groups described above, but it comprises at least one double bond.

For example, the term "alkenyl group" comprises a linear alkenyl group (e.g., vinyl, propenyl, butenyl, pentenyl, hexenyl, heptenyl, octenyl, nonenyl, decenyl, etc.), a branched alkenyl group, a cycloalkenyl group (e.g., cyclopropenyl, cyclopentenyl, cyclohexenyl, cycloheptenyl, cyclooctenyl), a cycloalkenyl group substituted with an alkyl or alkenyl group, and an alkenyl group substituted with a cycloalkyl or cycloalkenyl group. The term "alkenyl group" also comprises an alkenyl group containing an oxygen, nitrogen, sulfur or phosphorous atom that replaces one or more carbon atoms in the hydrocarbon backbone. In some embodiments, a linear or branched alkenyl group has 6 or less carbon atoms in the backbone thereof (e.g., a linear $C_{2-6}$ alkenyl group, and a branched $C_{3-6}$ alkenyl group). The term $C_{2-6}$ alkylene group comprises an alkenyl group containing 2 to 6 carbon atoms.

In addition, the term "alkenyl group" comprises "an unsubstituted alkenyl group" and "a substituted alkenyl group", and the latter refers to an alkenyl groups in which the hydrogen on one or more carbon atoms in the hydrocarbon backbone is replaced by a substituent. The substituent can include, for example, alkyl, alkynyl, halogen, hydroxy, alkylcarbonyloxy, arylcarbonyloxy, alkoxycarbonyloxy, aryloxycarbonyloxy, hydroxycarbonyl, alkylcarbonyl, arylcarbonyl, alkoxycarbonyl, aminocarbonyl, alkylaminocarbonyl, dialkylaminocarbonyl, alkylthiocarbonyl, alkoxy, phosphate, phosphorate, cyano, amino (including alkylamino, dialkylamino, arylamino, diarylamino, and alkylarylamino), acylamino (including alkylcarbonylamino, arylcarbonylamino, carbamoyl, and ureido), amidino, imino, mercapto, alkylthio, arylthio, hydroxythiocarbonyl, sulfate, alkylsulfinyl, sulfonyl, sulfamoyl, sulfonylamino, nitro, trifluoromethyl, cyano, azido, heterocyclyl, alkylaryl, or aromatic groups.

The term "alkoxy group" comprises a substituted and unsubstituted alkyl group covalently connected to an oxygen atom. Examples of alkoxy groups include methoxy, ethoxy, isopropyloxy, propoxy, butoxy, and pentoxy groups. Examples of the substituted alkoxy groups include a haloalkoxy group. The alkoxy group can be substituted with the following groups: alkenyl, alkynyl, halogen, hydroxy, alkylcarbonyloxy, arylcarbonyloxy, alkoxycarbonyloxy, aryloxycarbonyloxy, hydroxycarbonyl, alkylcarbonyl, arylcarbonyl, alkoxycarbonyl, aminocarbonyl, alkylaminocarbonyl, dialkylaminocarbonyl, alkylthiocarbonyl, phosphate, cyano, amino (including alkylamino, dialkylamino, arylamino, diarylamino, and alkylarylamino), acylamino (including alkylcarbonylamino, arylcarbonylamino, carbamoyl, and ureido), amidino, imino, mercapto, alkylthio, arylthio, hydroxythiocarbonyl, alkylsulfinyl, sulfonyl, sulfamoyl, sulfonylamino, nitro, trifluoromethyl, cyano, azido, heterocyclyl, alkylaryl or aromatic groups.

The Synthetic Procedure of the Compounds Provided by the Present Invention:

The compounds represented by the general formula of the present invention can be synthesized according to a variety of reaction procedures. Those skilled in the art can readily design the reaction procedures of other compounds by virtue of some preparation methods provided in the examples herein.

In a general synthetic route, the A-H compound is firstly synthesized. The preparation method of this compound can refer to the patent WO2009158404. After the A-H compound is obtained, the compound further reacts with a fragment containing a NO provider. The reaction is generally carried out at a temperature of −20° C. to 50° C. in the presence of a condensing agent such as DCC, EDCI, CDI, or HOBt, in the presence or absence of a base such as DMAP, in an anhydrous organic solvent such as DMF, THF, toluene, dioxane, or polyhalogenated aliphatic hydrocarbon. The reaction is completed within a period of 30 min to 36 h.

After the A-H compound is prepared, it generally reacts with an anhydride to produce an ester firstly. The reaction is stirred at a temperature of 100° C. to 120° C. in the presence of an anhydrous organic solvent such as DMF, THF, DCM, and it is completed within a period of 2 to 4 h. After purification, the resulting product reacts with an acyl chloride compound at a temperature of −20° C. to 40° C. in the presence of an organic base such as DMAP, triethylamine, or pyridine, in an inert organic solvent such as DMF, THF, benzene, toluene, dioxane, or polyhalogenated aliphatic hydrocarbon. The reaction is completed within a period of 30 min to 36 h. After purification, the condensation reaction of the resulting product with a chemical fragment containing a NO provider is then carried out.

The NO provider compound provided by the present invention is represented by Y or $Y_0$.

The synthetic method thereof can refer to the patents WO2014113700, WO2015109210, EP0984012, and EP1336602.

When B in the general formula of the compound of the present invention is selected from

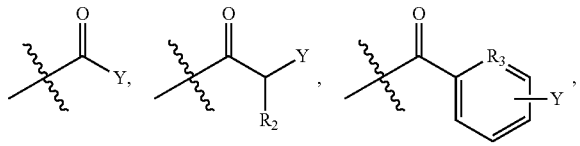

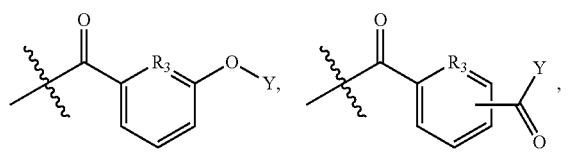

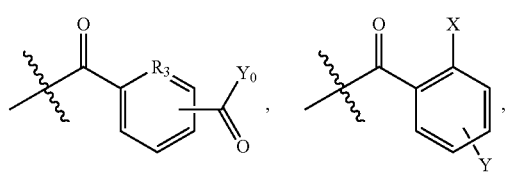

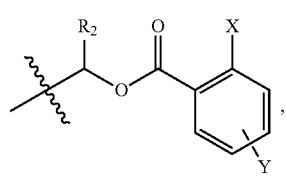

the synthesis method can refer to Example 2 of the present invention.

When B is selected from

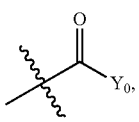

the synthesis method can refer to Example 3 of the present invention.

When B is selected from

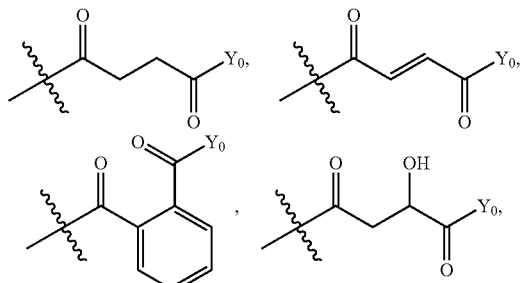

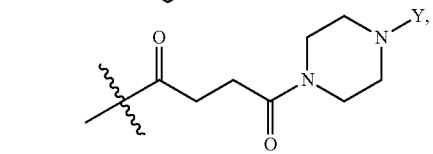

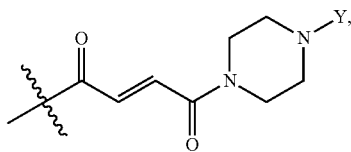

the synthesis method can refer to Example 6 of the present invention.

When B is selected from

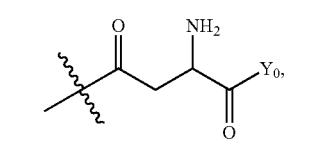

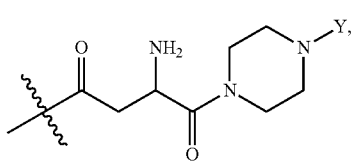

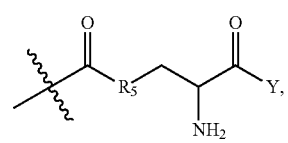

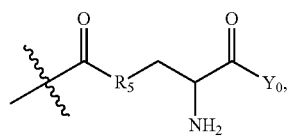

the synthesis method can refer to Example 18 of the present invention.

When B is selected from

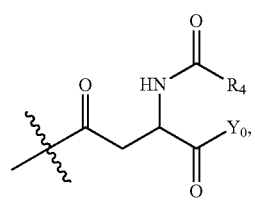

the synthesis method can refer to Example 24 of the present invention.

When B is selected from

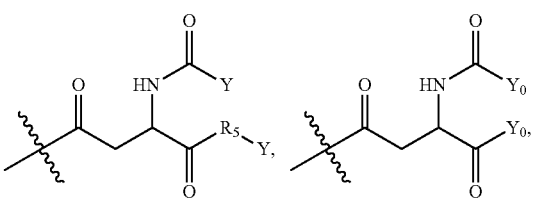

-continued

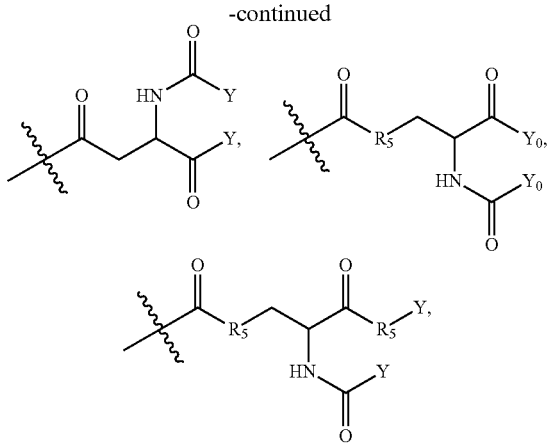

the synthesis method can refer to Example 25 of the present invention.

When B is selected from

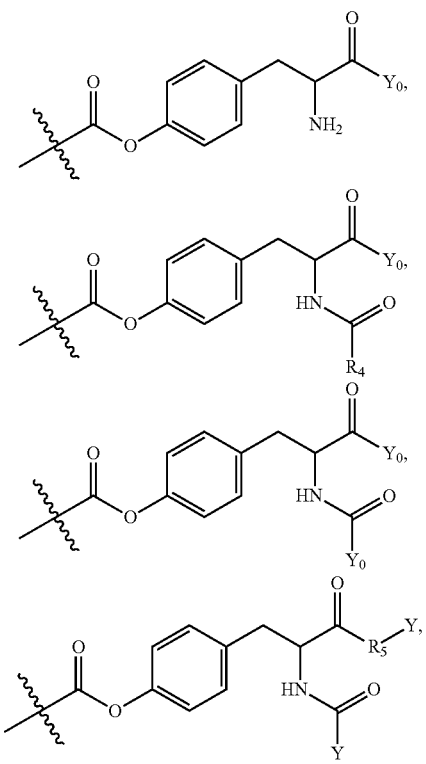

the synthesis method can refer to Example 23 and Example 25 of the present invention.

When B is selected from —C(O)—CH₂—NH—C(O)—Y₀; —C(O)—CH₂—NH—C(O)—Y; —C(O)—CH₂—CH₂—NH—C(O)—Y₀; —C(O)—CH₂—CH₂—NH—C(O)—Y, the synthesis method can refer to Example 9 of the present invention.

The following abbreviations can be used throughout the examples and the description:
g (gram); mg (milligram);
L (liter); mL (milliliter);
M (molar); mM (millimole/liter);
i.v. (intravenous); Hz (Hertz);
MHz (megahertz); mol (mole);
mmol (millimole); TLC (thin layer chromatography);
min (minute); h (hour);
MeOH (methanol); THF (tetrahydrofuran);
TEA (triethylamine); TFA (trifluoroacetic acid);
DIPEA (N, N-diisopropylethylamine) DMAP (4-dimethylaminopyridine);
DMSO (dimethyl sulfoxide); EtOAc (ethyl acetate);
DCM (dichloromethane); BOC (tert-butoxycarbonyl);
DMF (N, N-dimethylformamide); CDI (1, 1'-carbonyldiimidazole);
IBCF (isobutyl chloroformate); HOAc (acetic acid);
HOBt (1-hydroxybenzotriazole); DCC (dicyclohexylcarbodiimino);
Et₂O (diethyl ether); Ac₂O (acetic anhydride)
EDCI (1-(3-dimethylaminopropyl)-3-ethylcarbodiimide hydrochloride);
NMP (N-methylpyrrolidone) Me (methyl);
P-TSA (p-toluenesulfonic acid); Ac (acetyl);
OMe (methoxy); Et (ethyl);
EtOH (ethanol); RP (reverse phase);
BOP (benzotriazol-1-yloxy tris(dimethylamino) phosphonium hexafluorophosphate).

Representative Compounds of the General Formula A-B of the Present Invention are as Follows:

2-(4-(2-nitroxy-ethoxy)-3,5-dimethylphenyl)-5,7-dimethoxyquinazolin-4(3H)-one;

2-[4-(5,7-dimethoxy-4-oxo-3,4-dihydro-quinazolin-2-yl)-2,6-dimethyl-phenoxy)-ethyl 3-nitroxymethyl-benzoate;

N-((2-(4-(5,7-dimethoxy-4-oxo-3,4-dihydro-quinazolin-2-yl)-2,6-dimethylphenoxy)ethoxy)carbonyloxy)-5-methylthiophene-2-sulfonamide;

N-((2-(4-(5,7-dimethoxy-4-oxo-3,4-dihydroquinazolin-2-yl)-2,6-dimethylphenoxy)ethoxy)carbonyloxy)-5-methylfuran-2-sulfonamide;

2-[4-(5,7-dimethoxy-4-oxo-3,4-dihydro-quinazolin-2-yl)-2,6-dimethyl-phenoxy]-ethyl 3-(3-nitroxy-propionyl)-benzoate;

2-[4-(5,7-dimethoxy-4-oxo-3,4-dihydro-quinazolin-2-yl)-2,6-dimethyl-phenoxy]-ethyl 3-(nitroxy)-2,2-di((nitroxy)methyl) propyl succinate;

2-[4-(5,7-dimethoxy-4-oxo-3,4-dihydro-quinazolin-2-yl)-2,6-dimethyl-phenoxy]-ethyl 3-(2,3-dinitroxy-propoxy)-benzoate;

2-[4-(5,7-dimethoxy-4-oxo-3,4-dihydro-quinazolin-2-yl)-2,6-dimethyl-phenoxy]-ethyl 4,5-dinitroxy-pentanoate;

2-[4-(5,7-dimethoxy-4-oxo-3,4-dihydro-quinazolin-2-yl)-2,6-dimethyl-phenoxy]-ethyl(4-nitroxy-butyrylamino)-acetate;

2-nitroxy-ethyl 2-amino-3-(4-{2-[4-(5,7-dimethoxy-4-oxo-3,4-dihydro-quinazolin-2-yl)-2,6-dimethyl-phenoxy]-ethoxycarbonyloxy}-phenyl)-propionate hydrochloride;

2-[4-(5,7-dimethoxy-4-oxo-3,4-dihydro-quinazolin-2-yl)-2,6-dimethyl-phenoxy]-ethyl 4-(2-oxo-3-nitroxymethyl-1,2,5-oxadiazol-3-methyl)oxy-4-oxo-butyrate;

2-[4-(5,7-dimethoxy-4-oxo-3,4-dihydro-quinazolin-2-yl)-2,6-dimethyl-phenoxy]-ethyl 3-(6-nitroxy-caproylamido)-propionate;

2-[4-(5,7-dimethoxy-4-oxo-3,4-dihydro-quinazolin-2-yl)-2,6-dimethyl-phenoxy]-ethyl(2-oxo-4-phenyl-furazan-3-yl)-methyl 2-hydroxy succinate;

4-(2-(((2-(4-(5,7-dimethoxy-4-oxo-3,4-dihydro-quinazolin-2-yl)-2,6-dimethyl-phenoxy)ethoxy)carbonyl)oxy) ethoxy)-3-(phenylsulfonyl)-2-oxo-furazan;

2-[4-(5,7-dimethoxy-4-oxo-3,4-dihydro-quinazolin-2-yl)-2,6-dimethyl-phenoxy]-ethyl(E)-4-((furan-2-sulfonylamino)oxy)-4-oxo-2-butenoate;

2-[4-(5,7-dimethoxy-4-oxo-3,4-dihydro-quinazolin-2-yl)-2,6-dimethyl-phenoxy]-ethyl 4-(((3-(methylsulfonyl)phenyl)sulfonamido)oxy)-4-oxo-butyrate;

2-[4-(5,7-dimethoxy-4-oxo-3,4-dihydro-quinazolin-2-yl)-2,6-dimethyl-phenoxy]-ethyl 4-[4-(2-(nitroxy)ethyl)-piperazin-1-yl]-4-oxo-butyrate;

1-(2,3-dinitroxy-propyl) 4-{2-[4-(5,7-dimethoxy-4-oxo-3,4-dihydro-quinazolin-2-yl)-2,6-dimethyl-phenoxy]-ethyl}2-amino-succinate hydrochloride;

2-[4-(5,7-dimethoxy-4-oxo-3,4-dihydro-quinazolin-2-yl)-2,6-dimethyl-phenoxy]-ethyl(6-nitroxy-hexahydrofuro[3,2-b]furan-3-yl)-carbonate;

2-[4-(5,7-dimethoxy-4-oxo-3,4-dihydro-quinazolin-2-yl)-2,6-dimethyl-phenoxy]-ethyl(6-nitroxy-hexahydrofuro[3,2-b]furan-3-yl)-carbamate;

2-[4-(5,7-dimethoxy-4-oxo-3,4-dihydro-quinazolin-2-yl)-2,6-dimethyl-phenoxy]-ethyl 4-(((5-chlorothiophene)-2-sulfonylamino)oxy)-4-oxo-butyrate;

2-(N-(((2-(4-(5,7-dimethoxy-4-oxo-3,4-dihydro-quinazolin-2-yl)-2,6-dimethyl-phenoxy]-ethoxy)carbonyl)oxy)sulfamoyl)-1-methyl-1H-pyridine 1-2-onium salt;

3,4-(dinitroxy) butyl 2-acetylamino-3-(4-((2-(5,7-dimethoxy-4-oxo-3,4-dihydro-quinazolin-2-yl)-2,6-dimethyl-phenoxy]-ethoxy)carbonyl)oxy)phenyl) propionate;

3-(nitroxy)-2,2-di(nitroxymethyl) propyl 4-(2-[4-(5,7-dimethoxy-4-oxo-3,4-dihydro-quinazolin-2-yl)-2,6-dimethyl-phenoxy]butyl)-4-oxo-2-acetylamino-butyrate; and 2-nitroxyethyl 4-(2-[4-(5,7-dimethoxy-4-oxo-3,4-dihydro-quinazolin-2-yl)-2,6-dimethyl-phenoxy]butoxy)-4-oxo-2-(2-(nitroxy)acetylamino)-butyrate.

As mentioned above, the present invention also comprises pharmaceutically acceptable salts and stereoisomers of the compounds of formula (II).

The pharmaceutically acceptable salts mean inorganic basic salts, such as sodium, potassium, calcium or aluminum salts; and organic basic salts, such as lysine, arginate, triethylamine, dibenzylamine, piperidine salts and other pharmaceutically acceptable organic amine salts.

When at least one nitrogen atom, which is capable of forming a salt, is contained in the molecule of the compound of the present invention, the compound can be converted to the corresponding salt by reacting with the corresponding organic or inorganic acids in an organic solvent such as acetonitrile and tetrahydrofuran. Typical organic acids are oxalic acid, tartaric acid, maleic acid, succinic acid, and citric acid. Typical inorganic acids are nitric acid, hydrochloric acid, sulfuric acid, and phosphoric acid, preferably nitric acid.

When one or more asymmetric carbon atoms are contained in the compound of the present invention, they can exist in the following forms: an optically pure enantiomer, a pure diastereomer, a mixture of enantiomerics, a mixture of diastereomers, a racemic mixture of enantiomers, a racemate, or a mixture of the racemates. All the possible isomers, stereoisomers of the compound of formula (II) and the mixture thereof are also within the scope of the present invention.

The invention also provides a pharmaceutical composition comprising at least one compound described above and optionally one or more pharmaceutically acceptable carriers and/or diluents.

The pharmaceutical compositions provided by the present invention can be prepared in any form, for example granules, powders, tablets, coated tablets, capsules, pills, syrups, drops, solutions, suspensions and emulsions, or sustained release preparations of the active ingredients, wherein examples of capsules include hard or soft gelatin capsules, the granules and powders can be in a non-effervescent or effervescent form.

The pharmaceutical composition of the present invention can further comprise one or more pharmaceutically or physiologically acceptable carriers which will be suitably formulated for the convenience of administration. For example, the pharmaceutically or physiologically acceptable carriers can be saline, autoclaved water, Ringer's solution, buffered saline, glucose, maltodextrin, glycerol, ethanol, and the mixture thereof. The pharmaceutical composition of the present invention can further comprise pharmaceutically or physiologically acceptable additives such as diluents, lubricants, binders, glidants, disintegrants, sweeteners, flavoring agents, humectants, dispersants, surfactants, solvents, coating agents, foaming agents, or fragrances.

Examples of diluents that can be used include but not limited to, lactose, sucrose, starch, kaolin, salt, mannitol, and dicalcium phosphate. Examples of lubricants include but not limited to, talc, starch, magnesium or calcium stearates, lycopodium, and stearic acid. Examples of binders include but not limited to, microcrystalline cellulose, gum tragacanth, glucose solution, mucilago acaciae, gelatin solution, sucrose, and starch paste. Examples of glidants include but not limited to, colloidal silica. Examples of disintegrants include but not limited to, croscarmellose sodium, sodium starch glycolate, alginic acid, corn starch, potato starch, bentonite, methylcellulose, agar, and carboxymethylcellulose. Examples of sweeteners include but not limited to, sucrose, lactose, mannitol, and artificial sweeteners such as sodium cyclamate, and saccharin, and any amount of flavoring agents for spray drying. Examples of flavoring agents include but not limited to, natural flavoring agents extracted from plants such as fruits, and flavorful compounds such as, but not limited to, peppermint, and methyl salicylate. Examples of humectants include but not limited to, propylene glycol monostearate, sorbitan monooleate, diethylene glycol monolaurate, and polyoxyethylene lauryl ether.

The pharmaceutical composition of the present invention can be administered by a variety of routes according to conventional methods including oral, intravenous, intraarterial, intraperitoneal, intrathoracic, transdermal, nasal, inhalational, rectal, ophthalmic, and subcutaneous import routes.

Pharmaceutically acceptable carriers optionally added into the pharmaceutical composition of the present invention are one or more of water, alcohol, honey, mannitol, sorbitol, dextrin, lactose, caramel, gelatin, calcium sulfate, magnesium stearate, talc, kaolin, glycerin, Tween, agar, calcium carbonate, calcium bicarbonate, surfactant, cyclodextrin and its derivatives, phospholipids, phosphate salts, starchs and their derivatives, derivatives of silicon, celluloses and their derivatives, pyrrolidones, polyethylene glycols, acrylic resins, phthalates, acrylic copolymers, and trimellitates.

As verified by pharmacological experiments, the compound or pharmaceutical composition provided by the present invention can exert anti-inflammatory effects by inhibiting interleukin-66, vascular cell adhesion molecule-1, and monocyte chemoattractant protein-1; exert immunosuppressive effects by inhibiting the release of inflammatory cytokines; and regulate glucose metabolism disorder and lipid metabolism disorder in vivo by promoting the increase of high-density lipoprotein cholesterol (HDL-C), inhibiting the synthesis of cholesterol, fatty acid, and triglyceride and reducing the uptake and production of glucose.

On the other hand, the compound or pharmaceutical composition of the present invention also has neuroprotective effect. It can resist nerve apoptosis, inhibit nerve necrosis, and promote nerve regeneration.

The present invention provides the use of the compound or pharmaceutical composition mentioned above in the preparation of a medicament for preventing and treating cardiovascular and cerebrovascular diseases, inflammatory diseases, neurodegenerative diseases, metabolic disorders and their secondary diseases.

The present invention provides a method for preventing and/or treating cardiovascular and cerebrovascular diseases, inflammatory diseases, neurodegenerative diseases, metabolic disorders and their secondary diseases, which comprises administering therapeutically effective amount of the compound or pharmaceutical composition according to the present invention to a subject in need.

In another aspect, the compound or pharmaceutical composition according to the present invention are used for preventing and/or treating cardiovascular and cerebrovascular diseases, inflammatory diseases, neurodegenerative diseases, metabolic disorders and their secondary diseases.

Furthermore, the cardiovascular and cerebrovascular diseases include atherosclerosis, cerebral atherosclerosis, cerebral thrombosis, cerebral infarction, hyperlipidemia, ischemic myocardial injury, stroke, coronary heart disease, cardiac hypertrophy, heart failure, myocardial infarction, rheumatic heart disease, congenital heart disease, left ventricular dysfunction, endothelial dysfunction, fibrous degeneration and structural remodeling after endothelial dysfunction, hypertrophic cardiomyopathy, diabetic cardiomyopathy, supraventricular and ventricular arrhythmia, atrial fibrillation, cardiac fibrosis, atrial flutter, harmful vascular remodeling, myocardial infarction and its sequela, angina, hypertension, primary and secondary pulmonary hypertension, renovascular hypertension, hypertensive retinopathy, or retinal vasculopathy.

The inflammatory diseases include chronic kidney disease, chronic nephritis, arthritis, rheumatoid arthritis, psoriasis, inflammatory bowel disease, autoimmune diseases, ulcerative colitis, gastric ulcer, chronic gastritis, cervicitis, hepatitis B, hepatitis C, non-alcoholic steatohepatitis, chronic skin ulcers, organ transplant rejection; neuroinflammatory diseases such as diabetic neuropathy, amyotrophic lateral sclerosis, prion diseases, spinal muscular atrophy, multiple sclerosis, neuropathic pain, primary lateral sclerosis, meningitis, or viral encephalitis.

The neurodegenerative diseases include Alzheimer's disease, Parkinson's disease, multiple sclerosis, and Huntington's disease.

The metabolic disorders and their secondary diseases include type 2 diabetes, diabetic dyslipidemia, diabetic macular edema, diabetic retinopathy, macular degeneration, cataract, diabetic nephropathy, glomerulosclerosis, diabetic neuropathy, metabolic acidosis, premenstrual syndrome, appetite regulation and obesity.

The dosage of the compound provided by the present invention generally ranges from about 0.001 mg/kg to 1000 mg/kg per day, preferably about 0.01 mg/kg to 100 mg/kg per day, more preferably about 0.1 to 20 mg/kg per day. The dosage range of the pharmaceutical composition is calculated as the amount of the above compounds contained therein.

The NO prodrug provided by the present invention has a novel molecular structure, and has the following features and advantages:

① The NO provider-type prodrug is decomposed in vivo into small molecule therapeutic drugs, which can regulate the expression or secretion of ApoA-I, and NO molecules, thereby further providing exogenous NO based on the pharmacological effect of the ApoA-I regulators per se, which is of great significance for the treatment of cardiovascular and cerebrovascular diseases.

② The chemical structures of some ApoA-I regulators selected by the inventors comprise free alcoholic hydroxyl groups. Such drugs are easy to directly conjugate with glucuronic acid in vivo to carry out phase II bioconversion so as to be metabolized. In addition, such drugs are directly excreted out of the body by being oxidized to free carboxylic acid through phase I bioconversion catalyzed by alcohol dehydrogenase in vivo, or the free carboxylic acid further conjugate with glycine to carry out phase II bioconversion so as to be metabolized. These ApoA-I regulators are coupled with NO providers by the inventors so as to form the NO prodrugs, which retard these metabolic pathways to a great extent, thereby increasing the bioavailability of the drugs, increasing the stability of the drugs, and achieving the effect of prolonging the effect of the drugs.

③ Many drugs used clinically for cardiovascular and cerebrovascular diseases have a relatively high lipophilicity, e.g., the alcohol-water partition coefficient (log P) values of both statins and sartan esters are about 5. Nevertheless, the ApoA-I regulators are coupled with NO providers by the inventors so as to form the NO prodrugs, which have an increased lipophilic level, and the log P value increases from 3 to 5, thereby the absorption fraction of the drug in vivo and further the bioavailability increase.

BRIEF DESCRIPTION OF THE SEVERAL VIEWS OF THE DRAWINGS

FIG. 1 shows the effect of the tested compounds on the NO level in the serum of C57 mice.

DETAILED DESCRIPTION OF THE INVENTION

Example 1: Preparation of 2-(4-(2-nitrooxy-ethoxy)-3,5-dimethylphenyl)-5,7-dimethoxyquinazolin-4(3H)-one (H101)

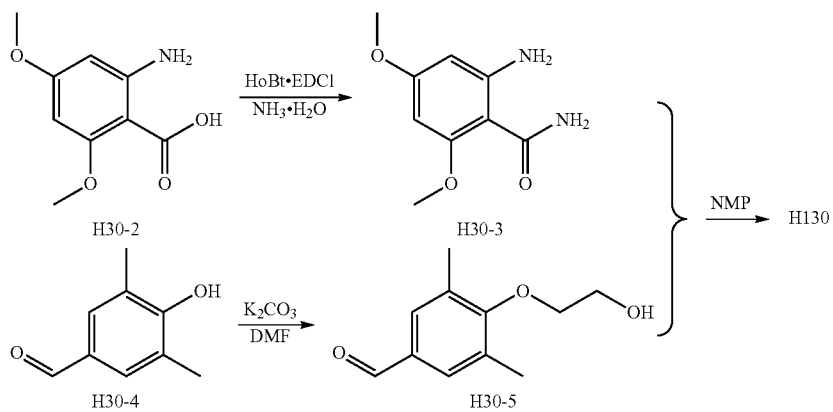

Step 1

The starting materials H30-2 (19.7 g, 0.1 mol), HOBt (20.3 g, 0.15 mol), carbodiimide EDCI (28.8 g, 0.15 mol), DIPEA (32.3 g, 0.25 mol), and THF (1 L) were added into a three-necked round bottom flask, and stirred for 3 h. Then 40 mL of aqueous ammonia was added, stirring overnight at room temperature. After the completion of reaction detected by TLC, the mixture was extracted with DCM (2×200 mL). The organic layer was separated, then washed twice with water, and distilled under reduced pressure. Ether (50 mL) was added into the residue. After stirring and mixing homogeneously, the mixture was filtered. The filtrate was discarded to give the intermediate H30-3 (13.4 g, yield 68%).

Step 2

The starting materials H30-4 (36 g, 0.24 mol), 2-bromoethanol (60 g, 0.48 mol), potassium carbonate (130 g, 0.94 mol), and EtOH (600 mL) were added into a beaker. The mixture was refluxed at 79° C. for 8 h. After the completion of the reaction detected by TLC, the mixture was filtered. The resulting filtrate was distilled under reduced pressure. Water (300 mL) was then added to the residue. The mixture was extracted with EtOAc (3×100 mL). The organic layer was separated, then washed with saturated aqueous NaCl solution (3×100 mL), dried by adding sodium sulfate, and filtered. The resulting filtrate was distilled under reduced pressure. The resulting crude product was purified by silica gel column chromatography (eluent: petroleum ether:ethyl acetate=4:1) to give the intermediate H30-5 (37.5 g, yield 80%).

Step 3

The intermediate H30-3 (15.2 g, 77.5 mol), H30-5 (15.06 g, 77.5 mmol), NaHSO$_3$ (8.9 g, 85.3 mmol), P-TSA (1.34 g, 7.75 mmol), and NMP (140 mL) were added into a flask in the presence of nitrogen gas. The mixture was stirred for 3 h at 130° C. After the completion of the reaction detected by TLC, the mixture was extracted by adding water (450 mL) and DCM (500 mL). The separated aqueous layer was extracted with DCM (4×400 mL). The resulting organic layers were combined, washed with water (3×400 mL), dried by adding sodium sulfate, and filtered. The resulting filtrate was distilled under reduced pressure. The resulting crude product was purified by silica gel column chromatography (dichloromethane:methanol=80:1) to give the intermediate H130:2-(4-(2-hydroxyethoxy)-3,5-dimethylphenyl)-5,7-dimethoxyquinazoline-4(3H)-one (18 g, yield 62.7%).

Step 4

The intermediate H130 (370.4 mg, 1 mmol) and concentrated nitric acid (35 mL) were mixed at 0° C. Let the mixture stand for 2 h. After the completion of the reaction detected by TLC, the mixture was slowly heated to room temperature. Water (100 mL) and DCM (100 mL) were added into the mixture to separate it into layers. The aqueous layer was separated, and extracted with DCM (3×100 mL). The resulting organic layers were combined, dried by adding sodium sulfate, and filtered. The resulting filtrate was distilled under reduced pressure. The crude product was purified by silica gel column chromatography (eluent: dichloromethane:methanol=100:1) to give 120 mg of the target compound 2-(4-(2-nitroxy-ethoxy)-3,5-dimethylphenyl)-5,7-dimethoxyquinazolin-4(3H)-one, yield 29%. Its structure was confirmed by $^1$H NMR and mass spectrometry. $^1$H NMR (400 MHz, CDCl$_3$) δ: 9.87 (s, 1H), 7.75 (s, 2H), 6.83 (d, J=2.2 Hz, 1H), 6.46 (d, J=2.2 Hz, 1H), 4.90-4.81 (m, 2H), 4.15-4.09 (m, 2H), 3.95 (d, 6H), 2.38 (s, 6H). LC-MS: m/z (ES$^+$), 415[M+1]$^+$.

Example 2: Preparation of 2-[4-(5,7-dimethoxy-4-oxo-3,4-dihydro-quinazolin-2-yl)-2,6-dimethyl-phenoxy]-ethyl 3-nitroxymethyl-benzoate (H102)

M-bromomethyl benzoic acid (258 mg, 1.2 mmol), AgNO$_3$ (245 mg, 1.44 mmol), and acetonitrile (5 ml) were added into a 25 mL flask. The mixture was stirred at 70° C. for 48 h. After the completion of the reaction detected by TLC, the mixture was filtered. The resulting filtrate was distilled under reduced pressure to give 3-nitroxymethyl-benzoic acid (211 mg, yield 89%).

H130 (370 mg, 1 mmol), 3-nitroxymethyl-benzoic acid (211 mg, 1 mmol), DCC (309 mg, 1.5 mmol), HOBt (202.5 mg, 1.5 mmol), DMAP (183 mg, 1.5 mmol) and THF (40 mL) were added into a 100 mL flask. The mixture was stirred at room temperature for 3 h. After the completion of the reaction detected by TLC, water (30 mL) and DCM (30 mL) were added to separate the mixture into layers. The aqueous layer was separated, and extracted with DCM (3×100 mL). The resulting organic layers were combined, dried by adding sodium sulfate, and filtered. The resulting filtrate was distilled under reduced pressure. The crude product was purified by silica gel column chromatography (eluent: dichloromethane:methanol=100:1) to give 180 mgof the target compound 2-[4-(5,7-dimethoxy-4-oxo-3,4-dihydro-quinazolin-2-yl)-2,6-dimethyl-phenoxy]-ethyl 3-nitroxymethyl-benzoate (H102), yield 32.7%. Its structure was confirmed by $^1$H NMR and mass spectrometry. $^1$H NMR (400 MHz, DMSO-d$_6$) δ: 11.86 (s, 1H), 8.09-8.00 (m, 2H), 7.91 (s, 2H), 7.78 (d, J=7.5 Hz, 1H), 7.62 (t, J=7.7 Hz, 1H), 6.74 (d, J=2.2 Hz, 1H), 6.51 (d, J=1.7 Hz, 1H), 5.67 (s, 2H), 4.64 (m, 2H), 4.19 (m, 2H), 3.86 (d, 6H), 2.31 (s, 6H). LC-MS: m/z (ES$^+$), 549 [M+1]$^+$.

Example 3: Preparation of N-((2-(4-(5,7-dimethoxy-4-oxo-3,4-dihydroquinazolin-2-yl)-2,6-dimethylphenoxy) ethoxy)carbonyloxy)-5-methylthiophene-2-sulfonamide (H103)

Step 1

2-methylthiophene (4.4 mL, 51 mmol) was added to a solution of CH$_2$Cl$_2$ (100 mL) containing ClSO$_3$OH (10 mL, 155 mmol) at 0° C. over a period of 30 min. At this temperature, the mixture was stirred for another 3 h. The mixture was then poured into ice water (100 mL), and extracted with CH$_2$Cl$_2$ (2×50 mL). The organic layer was collected, washed with saturated aqueous NaCl solution (100 mL), dried by sodium sulfate, and suction filtration. The resulting filtrate was distilled under reduced pressure to give 1.5 g of the intermediate 5-methylthiophene-2-sulfonyl chloride, yield 15%.

Step 2

Aqueous hydroxylamine solution (1.6 g, 22.8 mmol) was dissolved in THF (50 mL) and water (20 mL). The solution was cooled to −5° C. 5-methylthiophene-2-sulfonyl chloride (1.5 g, 7.6 mmol) dissolved in THF (10 mL) was added slowly at a temperature maintained not higher than 10° C. during the addition. After the complete consumption of sulfonyl chloride was detected by thin layer chromatography TLC, DCM (50 mL) was added. The organic layer was separated, washed with water (2×50 mL), dried by adding sodium sulfate, and suction filtration under reduced pressure. The resulting filtrate was distilled under reduced pressure. The resulting product was purified by silica gel column chromatography (eluent:petroleum ether:ethyl acetate=20:1 to 1:1) to give the intermediate N-hydroxy-5-methylthiophene-2-sulfonamide (0.5 g, yield 33%).

Step 3

The intermediate H130 (420 mg, 1.1 mmol), BOP (673 mg, 2.3 mmol), and THF (100 mL) were added into a 250 mL flask. The mixture was stirred for 48 h. After the completion of the reaction detected by TLC, the mixture was distilled under reduced pressure. Ether (60 mL) was added. The mixture was stirred, and filtrated. The filtrate was discarded. The resulting product was the intermediate 2-[4-(5,7-dimethoxy-4-oxo-3,4-dihydro-quinazolin-2-yl)-2,6-dimethyl-phenoxy]-ethylcarbonyl chloride (450 mg, yield 94.5%).

Step 4

The resulting product from Step 2 (193 mg, 1 mmol), triethylamine (202 mg, 2 mmol), and DCM (20 mL) were added into a 50 mL flask. The resulting product from Step 3 (216 mg, 0.5 mmol) was then added. The mixture was stirred at room temperature for 3 h. After the completion of the reaction detected by TLC, the mixture was filtrated. The resulting filtrate was distilled under reduced pressure. The resulting crude product was purified by silica gel column chromatography (eluent:methylene chloride:methanol=100:1) to give 130 mg of the target compound N-((2-(4-(5,7-dimethoxy-4-oxo-3,4-dihydroquinazolin-2-yl)-2,6-dimethylphenoxy)ethoxy)carbonyloxy)-5-methylthiophene-2-sulfonamide (H103), yield 44%. Its structure was confirmed by $^1$H NMR and mass spectrometry. $^1$H NMR (400 MHz, DMSO-$d_6$) δ: 11.88 (s, 1H), 11.59 (s, 1H), 7.91 (s, 2H), 7.58 (d, J=3.7 Hz, 1H), 7.05-7.01 (m, 1H), 6.74 (d, J=2.1 Hz, 1H), 6.52 (d, J=1.9 Hz, 1H), 4.56-4.51 (m, 2H), 4.09-4.05 (m, 2H), 3.86 d, 6H), 2.55 (s, 3H), 2.28 (s, 6H). LC-MS: m/z (ES$^+$), 589 [M+1]$^+$.

Example 4: Preparation of N-((2-(4-(5,7-dimethoxy-4-oxo-3,4-dihydroquinazolin-2-yl)-2,6-dimethylphenoxy)ethoxy)carbonyloxy)-5-methylfuran-2-sulfonamide (H104)

Step 1

2-methyl-furan (4.1 g, 50 mmol) was dissolved in DME (20 mL). Sulfur trioxide pyridine (9.5 g, 60 mmol) was added. The mixture was stirred under argon gas for 3 days. The reactant was diluted with EtOAc (60 mL), stirred at 5° C. for 2 h, and filtrated. The filtrate was discarded to give the intermediate 5-methylfuran-2-sulfonic acid (9 g, 75% yield).

Step 2

The product from the previous step (9 g, 37 mmol, pyridine salt) was dissolved in DME (60 mL). Oxalyl chloride (15 mL, 172 mmol) and DMF (1 mL) were added successively at 0° C. under argon gas. The mixture was then stirred at room temperature for 12 h. The mixture was then quenched with ice water (60 mL), and extracted with toluene (3×40 mL). The organic layer was separated. The organic layer was washed successively with aqueous NaHCO$_3$ solution (40 mL), water (40 mL), and saturated aqueous NaCl solution (40 mL), then dried by adding sodium sulfate, and filtrated. The resulting filtrate was distilled under reduced pressure to give the intermediate 5-methylfuran-2-sulfonyl chloride (2 g, 30% yield).

Step 3

50% of aqueous hydroxylamine solution (3 mL, 45 mmol), THF (15 mL), and water (5 mL) were mixed and cooled to 0° C. 5-methylfuran-2-sulfonyl chloride (2 g, 11 mmol) dissolved in THF (10 mL) was added dropwise at a temperature maintained not higher than 10° C. during the addition. The reactant was stirred for 5 min. After the complete consumption of sulfuryl chloride detected by thin layer chromatography TLC, the reactant was diluted with DCM (2×50 mL). The organic layer was separated, washed with water (10 mL), dried by adding sodium sulfate, and suction filtration under reduced pressure. The resulting filtrate was distilled under reduced pressure. The residue was purified by silica gel column chromatography (eluent:petroleum ether:ethyl acetate=4:1) to give the intermediate N-hydroxy-5-methylfuran-2-sulfonamide (0.6 g, 31% yield).

Step 4

The intermediate H130 prepared in Example 1 (185 mg, 0.5 mmol), pyridine (130 mg, 1.65 mmol), and DCM (5 ml) were added into a 25 mL flask. P-nitrophenyl chloroformate (110 mg, 0.55 mmol) dissolved in DCM (2 mL) was added dropwise into the above mixture at 0° C. The mixture was allowed to naturally warm up to room temperature, and stirred overnight. After the completion of the reaction detected by TLC, the reactant was washed with water. The organic layer was separated, and distilled under reduced pressure. The residue was purified by silica gel column chromatography (DCM:MeOH=95:5) to give the intermediate H04-7 (130 mg, yield 48.6%).

H130 ⟶

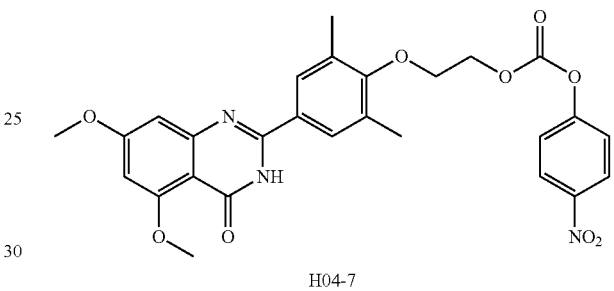

H04-7

Step 5

The intermediate H04-7 (160 mg, 0.3 mmol), N-hydroxy-5-methylfuran-2-sulfonamide (89 mg, 0.5 mmol), DMAP (122 mg, 1 mmol), and DCM (20 mL) were added into a 50 mL flask. The mixture was stirred overnight at room temperature. After the completion of the reaction detected by TLC, the mixture was then washed with water. The organic layer was separated, and distilled under reduced pressure. The residue was purified by silica gel column chromatography (DCM:MeOH=95:5) to give 10 mg of the target compound N-((2-(4-(5,7-dimethoxy-4-oxo-3,4-dihydroquinazolin-2-yl)-2,6-dimethylphenoxy)ethoxy)carbonyloxy)-5-methylfuran-2-sulfonamide (H104), yield 5.8%. Its structure was confirmed by $^1$H NMR and mass spectrometry. $^1$H NMR (400 MHz, DMSO-$d_6$) δ: 11.86 (s, 2H), 7.90 (s, 2H), 7.26 (d, J=3.5 Hz, 1H), 6.74 (d, J=2.3 Hz, 1H), 6.52 (d, J=2.2 Hz, 1H), 6.44 (d, J=3.4 Hz, 1H), 4.55-4.49 (m, 2H), 4.08-4.03 (m, 2H), 3.86 (d, 6H), 2.40 (s, 3H), 2.27 (s, 6H). LC-MS: m/z (ES$^+$), 573 [M+1]$^+$.

Example 5: Preparation of 2-[4-(5,7-dimethoxy-4-oxo-3,4-dihydro-quinazoline-2-yl)-2,6-dimethyl-phenoxy]-ethyl 3-(3-nitroxy-propionyl)-benzoate (H105)

The preparation method was the same as that of Example 2, except that the starting material was changed from m-bromomethylbenzoic acid to 3-(3-bromo-propionyl)-benzoic acid. The structure of the final product was confirmed by $^1$H NMR and mass spectrometry.

$^1$H NMR (400 MHz, DMSO-$d_6$) δ: 11.65 (s, 1H), 8.11-8.06 (m, 2H), 7.88 (s, 1H), 7.72 (d, J=6.2 Hz, 2H), 7.54 (m, 1H), 6.71 (d, J=2.8 Hz, 1H), 6.48 (d, J=2.5 Hz, 1H), 4.65 (m, 2H), 4.38 (m, 2H), 3.81 (d, 6H), 2.69 (m, 2H), 2.33 (s, 6H). LC-MS: m/z (ES$^+$), 592[M+1]$^+$.

Example 6: Preparation of 2-[4-(5,7-dimethoxy-4-oxo-3,4-dihydro-quinazolin-2-yl)-2,6-dimethyl-phenoxy]-ethyl 3-(nitroxy)-2,2-di((nitroxy)methyl) propyl succinate (H106)

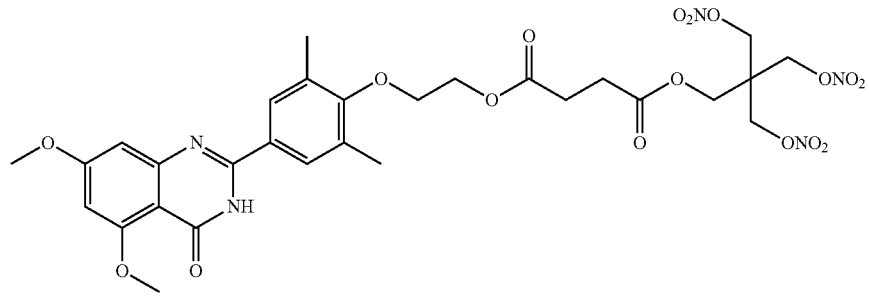

Step 1

The intermediate H130 prepared in Example 1 (1.5 g, 4.05 mmol), succinic anhydride (810 mg, 8.1 mmol), and DMF (15 mL) were added into a 25 mL flask. The mixture was stirred at 110° C. for 2 h. After the completion of the reaction detected by TLC, the mixture was distilled under reduced pressure. Ethyl acetate (30 mL) was then added to obtain a suspension. The suspension was filtered. The filtrate was discarded. The resulting product was the intermediate mono-{2-[4-(5,7-dimethoxy-4-oxo-3,4-dihydro-quinazolin-2-yl)-2,6-dimethyl-phenoxy]-ethyl}succinate (1 g, yield 52.5%).

Step 2

The product prepared in the previous step (400 mg) and DCM (20 mL) were added into a 50 mL flask, and mixed homogeneously. Oxalyl chloride (6 mL) was added. The mixture was stirred at room temperature for 1 h. After the completion of the reaction detected by TLC, the mixture was distilled under reduced pressure to give the product 4-chloro-4-oxobutyric acid {2-[4-(5,7-dimethoxy-4-oxo-3,4-dihydro-quinazolin-2-yl)-2,6-dimethyl-phenoxy]-ethyl} ester.

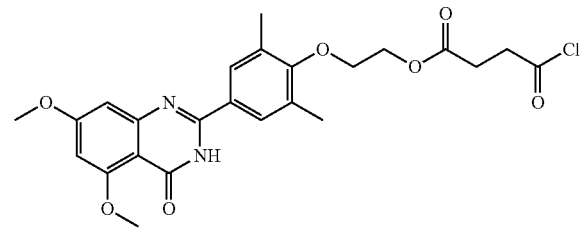 [SMILES: COc1cc(OC)c2c(=O)[nH]c(-c3cc(C)c(OCCOC(=O)CCC(=O)Cl)c(C)c3)nc2c1]

Step 3

2,2-di(nitroxymethyl)-3-nitroxy-propanol (285 mg, 1.05 mmol), triethylamine (239 mg, 2.35 mmol), and DCM (30 mL) were added into a 100 mL flask. The product obtained in step 2 (512 mg, 1.05 mmol) was dissolved in DCM (20 mL), and then added dropwise into the mixture at 0° C. After the reactant was warmed up to room temperature, it was stirred for 1 h. After the completion of the reaction detected by TLC, the reactant was washed with water. The organic layer was washed, dried with sodium sulfate, and filtered. The resulting filtrate was distilled under reduced pressure. The residue was purified by silica gel column chromatography (eluent:dichloromethane:methanol=95:5) to give 251 mg of the target compound (H106), yield 33%. Its structure was confirmed by $^1$H NMR and mass spectrometry.

$^1$H NMR (400 MHz, DMSO-$d_6$) δ: 11.80 (s, 1H), 7.85 (s, 2H), 6.71 (d, J=2.9 Hz, 1H), 6.50 (d, J=2.6 Hz, 1H), 4.49-4.38 (m, 2H), 4.08-4.18 (m, 2H), 3.98 (m, 1H), 3.85 (d, 6H), 3.45 (s, 6H), 2.79-2.81 (m, 4H), 2.33 (s, 6H). LC-MS: m/z (ES$^+$), 724[M+1]$^+$.

Example 7: 2-[4-(5,7-dimethoxy-4-oxo-3,4-dihydro-quinazolin-2-yl)-2,6-dimethyl-phenoxy]-ethyl 3-(2,3-dinitroxy-propoxy)-benzoate (H107)

The preparation method was the same as that of Example 2, except that the starting material was changed from m-bromomethylbenzoic acid to 3-allyloxy-benzoyl chloride (the preparation method referred to US 20150307650). The structure of the final product was confirmed by $^1$H NMR and mass spectrometry.

$^1$H NMR (400 MHz, DMSO-$d_6$) δ: 11.78 (s, 1H), 7.96-7.85 (m, 4H), 7.60 (m, 1H), 7.34 (m, 1H), 6.71 (d, J=2.8 Hz, 1H), 6.54 (d, J=3.2 Hz, 1H), 4.60 (m, 2H), 4.32 (m, 2H), 3.98-3.91 (m, 3H), 3.81 (d, 6H), 3.77-3.61 (m, 2H), 2.35 (s, 6H). LC-MS: m/z (ES$^+$), 655 [M+1]$^+$.

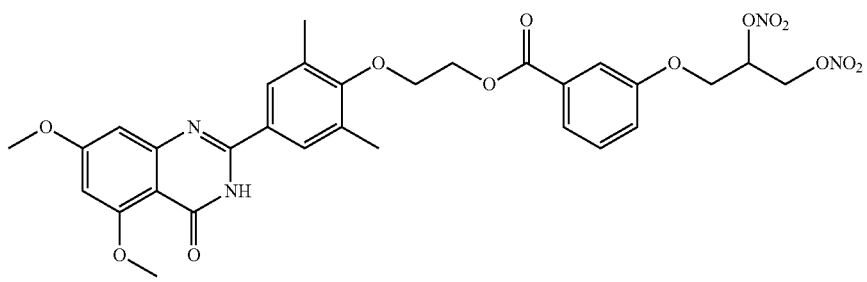

Example 8: Preparation of 2-[4-(5,7-dimethoxy-4-oxo-3,4-dihydro-quinazolin-2-yl)-2,6-dimethyl-phenoxy]-ethyl 4,5-dinitroxy-pentanoate (H108)

Step 1

4-pentenoic acid (2 g, 20 mmol) was dissolved in formic acid (5 mL), and added dropwise into formic acid solution (20 mL) containing 35% of hydrogen peroxide (28 mmol) at 50° C. over 15 min. At this temperature, the mixture was stirred for 2 h, and distilled under reduced pressure to give the product 2-keto-5-hydroxymethyl-tetrahydrofuran (2 g, yield 97%).

Step 2

The product obtained in the previous step (2 g, 17.2 mmol) was added into HCl (6M, 20 mL), and heated to reflux for 2 h. After the completion of the reaction detected by TLC, the reactant was distilled under reduced pressure to give the product 4,5-dihydroxy-pentanoic acid (2 g, yield 95%).

Step 3

The product obtained in the previous step (2 g, 15 mmol) was dissolved in ethyl acetate (10 mL), and added into nitric acid (90%, 15 mL, 300 mmol) and anhydrous acetic acid (20 mL) cooled by ice bath. The mixture was stirred in ice bath for 10 min, and then stirred at room temperature for 2 h. The mixture was distilled under reduced pressure at 40° C. The product was purified by silica gel column chromatography (gradient elution with eluent:petroleum ether:ethyl acetate=20:1 to 1:1) to give the intermediate 4,5-dinitroxy-pentanoic acid (1 g, yield 45%).

Step 4

The product obtained in the previous step (448 mg, 2 mmol), the intermediate H130 (370.4 mg, 1 mmol) prepared in Example 1, DCC (618 mg, 3 mmol), HOBt (405 mg, 3 mmol), DMAP (366 mg, 3 mmol), and THF (30 mL) were added into a 50 mL flask. The mixture was stirred overnight at room temperature. After the completion of the reaction detected by TLC, water (10 mL) and DCM (10 mL) were added. The separated aqueous layer was extracted with DCM (3×10 mL). The organic layer was collected. The organic layer was dried with sodium sulfate, and suction filtration. The filtrate was distilled under reduced pressure. The resulting crude product was purified by silica gel column chromatography (eluent:dichloromethane:methanol=100:1) to give 115 mg of the target compound 2-[4-(5,7-dimethoxy-4-oxo-3,4-dihydro-quinazolin-2-yl)-2,6-dimethyl-phenoxy]-ethyl 4,5-dinitroxy-pentanoate (H108), yield 20%. Its structure was confirmed by $^1$H NMR and mass spectrometry.

$^1$H NMR (400 MHz, DMSO-d$_6$) δ: 11.85 (s, 1H), 7.90 (s, 2H), 6.73 (d, J=2.6 Hz, 1H), 6.51 (d, J=2.5 Hz, 1H), 5.56-5.45 (m, 1H), 4.95 (d, J=2.0 Hz, 1H), 4.74 (d, J=5.8 Hz, 1H), 4.42-4.31 (m, 2H), 4.07-3.99 (m, 2H), 3.86 (d, 6H), 2.57 (m, 2H), 2.29 (s, 6H), 2.09-1.97 (m, 2H). LC-MS: m/z (ES$^+$), 576 [M+1]$^+$.

Example 9: Preparation of 2-[4-(5,7-dimethoxy-4-oxo-3,4-dihydro-quinazolin-2-yl)-2,6-dimethyl-phenoxy]-ethyl (4-nitroxy-butyrylamido)-acetate (H109)

Step 1

540 mg of 2-(4-(2-hydroxyethoxy)-3,5-dimethylphenyl)-5,7-dimethoxyquinazolin-4(3H)-one was dissolved in 35 mL of acetone. N-Boc-glycine (0.334 g) and 4-dimethylaminopyridine (DMAP, 20 mg) were added. The above mixed solution was cooled at 0° C. EDC (0.365 g) was added. The mixture was stirred at room temperature. After reacting for 2 h, the solvent was evaporated under vacuum. The resulting residue was washed with water (50 mL) and dichloromethane (3×50 mL) successively. The organic layer obtained was dried by sodium sulfate, and distilled under reduced pressure. The concentrate was purified by column chromatography (eluent: the ratio of n-hexane to ethyl acetate was 6:4) to give the intermediate (d), i.e. 2-[4-(5,7-dimethoxy-4-oxo-3,4-dihydro-quinazolin-2-yl)-2,6-dimethyl-phenoxy]-ethyl (tert-butoxycarbonylamino)-acetate.

Step 2

The intermediate (d) was added into 70 mL of dichloromethane. After sufficiently dissolving, HCl gas was introduced into the mixture for 1 h. The solvent was evaporated under reduced pressure to give the intermediate (e), i.e. glycine 2-[4-(5,7-dimethoxy-4-oxo-3,4-dihydro-quinazolin-2-yl)-2,6-dimethyl-phenoxy]-ethyl ester hydrochloride. The intermediate (e) was dissolved in 40 mL of dichloromethane. Pentafluorophenol 4-nitroxybutyrate (0.41 g), DMAP (20 mg), and triethylamine (0.3 mL) were further added. The mixture was stirred at room temperature. After reacting for 24 h, the mixture was wash with 5% of H$_3$PO$_4$ solution (50 mL). The resulting organic layer was dried by sodium sulfate, and distilled under reduced pressure. The concentrate was purified by column chromatography (eluent: the gradient of n-hexane/ethyl acetate was 1:1 to 100, the amount of ethyl acetate in the eluent was gradient increased until the eluent was 130 mL of ethyl acetate) to give the target compound.

$^1$H NMR (400 MHz, CDCl$_3$) δ: 9.92 (s, 1H), 8.91 (s, 1H), 7.73 (s, 2H), 6.80 (d, J=2.9 Hz, 1H), 6.51 (d, J=3.1 Hz, 1H), 4.81-4.75 (m, 2H), 4.26-4.15 (m, 4H), 4.08 (s, 2H), 3.90 (d, 6H), 2.36 (m, 8H), 2.09 (m, 2H); LC-MS: m/z (ES$^+$), 559 [M+1]$^+$.

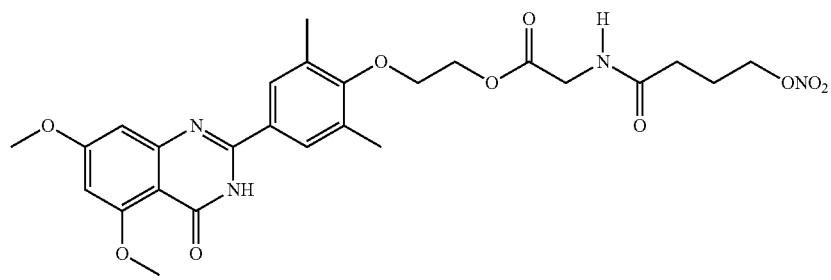

Example 10: Preparation of 2-nitroxy-ethyl 2-amino-3-(4-{2-[4-(5,7-dimethoxy-4-oxo-3,4-dihydro-quinazolin-2-yl)-2,6-dimethyl-phenoxy]-ethoxycarbonyloxy}-phenyl)-propionate hydrochloride (H110)

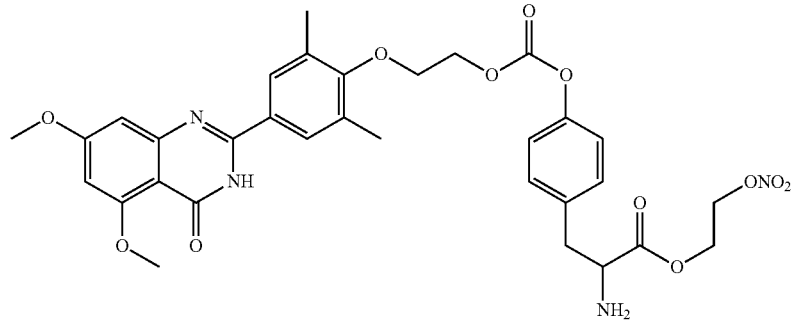

Step 1

Cesium carbonate (5.79 g) was added into Boc-(L)-tyrosine (5.0 g) in N, N-dimethylformamide (40 mL) solution. After dissolving, the solution was cooled to 0° C. 2-bromoethyl nitrate (3.48 g) dissolved in 20 mL of dichloromethane solution was added dropwise. The mixture was stirred at 0° C. After reacting for 20 min, the mixture was stirred continuously for 22 h at room temperature. After the completion of the reaction, the mixture was poured into 5% of aqueous $NaH_2PO_4$ solution, and extracted with diethyl ether (40 mL×4). The resulting organic layer was dried with sodium sulfate, and then distilled under reduced pressure. The concentrate was purified by column chromatography (eluent: the gradient of n-hexane/ethyl acetate was 9:1 to 1:1, and 4000 mL of the eluent was used in total) to give the intermediate (f), i.e. 2-(nitroxy) ethyl 2-(tert-butoxycarbonylamino)-3-(4-hydroxyphenyl)propionate.

Step 2

The intermediate (f) from the previous step was dissolved in 24 mL of dichloromethane Pyridine (0.5 mL) was added into the resulting solution. The solution was cooled to 0° C. P-nitrophenol chloroformate (980 mg) was added. The mixture was stirred at 0° C. After reacting for 10 minutes, the mixture was stirred for another 21 h at room temperature. After the completion of the reaction, the reactant was diluted with 25 mL of dichloromethane, washed with 1 M aqueous HCl solution, and then washed with saturated aqueous sodium carbonate solution. The resulting organic layer was dried by sodium sulfate, and distilled under reduced pressure. The concentrate was purified by column chromatography (eluent: the gradient of n-hexane/ethyl acetate was 98:2 to 6:4, and 1600 mL of the eluent was used in total) to give the intermediate (i), i.e. 2-(nitroxy) ethyl 2-(tert-butoxycarbonylamino)-3-(4-[4-nitrophenoxycarbonyloxy)-phenyl]-propionate.

Step 3

Scandium triflate (0.11 g) and 0.57 g of DMAP were added into the solution of intermediate (i) in dichloromethane (40 mL). The mixed solution was cooled to 0° C. 2-(4-(2-hydroxyethoxy)-3,5-dimethylphenyl)-5,7-dimethoxyquinazolin-4(3H)-one (1.07 g) was added. The mixture was stirred at room temperature, allowed to react for 70 h, and distilled under reduced pressure. The concentrate was purified by column chromatography (eluent: the gradient of n-hexane/ethyl acetate was 9:1 to 3:7, and 1600 mL of the eluent was used in total) to give the product 2-nitroxy-ethyl 2-(tert-butoxycarbonylamino)-3-(4-{2-[4-(5,7-dimethoxy-4-oxo-3,4-dihydro-quinazolin-2-yl)-2,6-dimethyl-phenoxy]-ethoxycarbonyloxy}-phenyl)-propionate.

Step 4

The product from the previous step was dissolved in 30 mL of dichloromethane at room temperature. After the product was sufficiently dissolved, HCl gas was introduced therein for 15 min. The reaction solution was further diluted with dichloromethane (35 mL), and washed with saturated aqueous sodium carbonate solution. The resulting organic layer was dried with sodium sulfate, and then distilled under reduced pressure. The concentrate was purified by reverse-phase flash chromatography (eluent: the gradient of water/acetonitrile was 9:1 to 2:8, and 1400 mL of the eluent was used in total) to give the product 2-nitroxy-ethyl 2-amino-3-(4-{2-[4-(5,7-dimethoxy-4-oxo-3,4-dihydro-quinazolin-2-yl)-2,6-dimethyl-phenoxy]-ethoxycarbonyloxy}-phenyl)-propionate. The product was treated with a solution of hydrochloric acid/diethyl ether, filtered, and dried under vacuum to give the target compound.

$^1$H NMR (400 MHz, DMSO-$d_6$) δ: 11.80 (s, 1H), 8.89 (d, 2H), 7.85 (s, 2H), 7.54-6.78 (m, 4H), 6.71 (d, J=2.4 Hz, 1H), 6.55 (d, J=2.5 Hz, 1H), 4.59-4.54 (m, 2H), 4, 50 (m, 2H), 4.39 (m, 4H), 4.21 (t, 1H), 3.91 (d, 6H), 3.61-3.32 (m, 2H), 2.27 (s, 6H). LC-MS: m/z (ES$^+$), 667 [M+1]$^+$.

Example 11: Preparation of 2-[4-(5,7-dimethoxy-4-oxo-3,4-dihydro-quinazolin-2-yl)-2,6-dimethyl-phenoxy]-ethyl 4-(2-oxo-3-nitroxymethyl-1,2,5-oxadiazol-3-methyl)oxy-4-oxo-butyrate (H111)

Step 1

(E)-2-butenal (30 g, 0.43 mol) and HOAc (60 mL) were added into a 1 L round bottom flask. $NaNO_2$ (107 g, 1.55 mol) dissolved in water (200 mL) was added dropwise into the mixture at 0° C., and stirred at room temperature for 70 min. After the completion of the reaction detected by TLC, 100 mL of water was added. The mixture was extracted with DCM (3×100 mL). The resulting organic layer was dried with sodium sulfate, and filtered. The resulting filtrate was distilled under reduced pressure. The residue was purified by silica gel column chromatography (eluent:petroleum ether: ethyl acetate=20:1) to give 2-oxo-3-methyl-4-formyl-1,2,5-oxadiazol (14.8 g, yield 26.9%).

Step 2

The product from the previous step (4.2 g, 33 mmol), $NaBH_4$ (2.5 g, 66 mmol), and THF (12 mL) were added into a 50 mL flask. The mixture was stirred at room temperature for 1.5 h. After the completion of the reaction detected by TLC, the reaction mixture was quenched with saturated aqueous ammonium chloride solution (20 mL). Water (10 mL) and ethyl acetate (10 mL) were further added. The organic layer was separated, distilled under reduced pressure to give 2-oxo-4-hydroxymethyl-3-methyl-1,2,5-oxadiazole (3.3 g, yield 76.9%).

Step 3

The product from the previous step (10.1 g, 77.7 mmol), Ac$_2$O (28 g, 274 mmol), DIPEA (55 g, 426 mmol), and DCM (200 mL) were added into a 1 L flask. The mixture was stirred at room temperature overnight. After the completion of the reaction detected by TLC, the reactant was washed with water (4×150 mL). The resulting aqueous layer was separated, and then extracted with DCM (4×100 mL). The resulting organic layers were combined, dried by sodium sulfate, and filtered. The resulting filtrate was distilled under reduced pressure. The residue was purified by silica gel column chromatography (eluent:petroleum ether:ethyl acetate=5:1) to give 2-oxo-3-methyl-4-((methylperoxy)methyl)-1,2,5-oxadiazole (16 g, yield 100%).

Step 4

The product from the previous step (4 g, 23 mmol), N-bromosuccinimide NBS (10.4 g, 58 mmol), benzoyl peroxide (catalytic amount), and CCl$_4$ (40 mL) were added into a 100 mL flask. The mixture was refluxed at 90° C. for 48 h. After the completion of the reaction detected by TLC, the reaction mixture was filtered. The resulting filtrate was distilled under reduced pressure. The crude product was purified by silica gel column chromatography (eluent:petroleum ether:ethyl acetate=3:1) to give 2-oxo-3-bromomethyl-4-((methylperoxy)methyl)-1,2,5-oxadiazole (2.14 g, yield 37%).

Step 5

The product from the previous step (2.14 g, 8.52 mmol), AgNO$_3$ (3.66 g, 21.5 mmol), and CH$_3$CN (20 mL) were added into a 100 mL flask. The mixture was stirred overnight at 60° C. After the completion of the reaction detected by TLC, the mixture was filtrated. The resulting filtrate was distilled under reduced pressure. The crude product was purified by silica gel column chromatography (eluent:petroleum ether:ethyl acetate=3:1) to give 2-oxo-3-nitroxymethyl-4-((methylperoxy)methyl)-1,2,5-oxadiazole (1.95 g, yield 98%).

Step 6

The product from the previous step (1.95 g, 8.37 mmol), HCl (2 mol/L, 3.3 mL), and 1,4-dioxane (16.7 mL) were added into a 100 mL flask. The mixture was stirred at 60° C. overnight. After the completion of the reaction detected by TLC, the mixture was distilled under reduced pressure. Water (100 mL) was added into the residue. Then the mixture was extracted with ethyl acetate (3×50 mL). The organic layer was dried by sodium sulfate, and filtered. The resulting filtrate was distilled under reduced pressure. The residue was purified by silica gel column chromatography (eluent:petroleum ether:ethyl acetate=4:1) to give 2-oxo-3-nitroxymethyl-4-hydroxymethyl-1,2,5-oxadiazole (1.4 g, yield 87%).

Step 7

The product from the previous step (245 mg, 1.28 mmol), triethylamine (260 mg, 2.56 mmol), and DCM (30 mL) were added into a 100 mL flask. The product obtained in Step 2 of Example 6 (624 mg, 1.28 mmol) was dissolved in DCM (20 mL), and added dropwise into the mixture at 0° C. After the reactant was warmed up to room temperature, the mixture was stirred for 1 h. After the completion of the reaction detected by TLC, the reactant was washed with water. The organic layer was separated, dried with sodium sulfate, and filtered. The resulting filtrate was distilled under reduced pressure. The residue was purified by silica gel column chromatography (DCM:MeOH=9:1) to give 50 mg of the target compound 2-[4-(5,7-dimethoxy-4-oxo-3,4-dihydro-quinazolin-2-yl)-2,6-dimethyl-phenoxy]-ethyl 4-(2-oxo-3-nitroxymethyl-1,2,5-oxadiazol-3-methyl)oxy-4-oxo-butyrate (H111), yield 6.1%. Its structure was confirmed by $^1$H NMR and mass spectrometry. $^1$H NMR (400 MHz, DMSO-d$_6$) δ: 11.86 (s, 1H), 7.91 (s, 2H), 6.74 (d, J=2.3 Hz, 1H), 6.52 (d, J=2.3 Hz, 1H), 5.60 (s, 1H), 5.32 (d, J=5.5 Hz, 2H), 4.80 (s, 1H), 4.39-4.31 (m, 2H), 4.05-3.98 (m, 2H), 3.87 (d, 6H), 2.76-2.63 (m, 4H), 2.30 (s, 6H). LC-MS: m/z (ES$^+$), 643 [M+1]$^+$.

Example 12: Preparation of 2-[4-(5,7-dimethoxy-4-oxo-3,4-dihydro-quinazolin-2-yl)-2,6-dimethyl-phenoxy]-ethyl 3-(6-nitroxy-caproylamido)propionate (H112)

The preparation method was the same as that of Example 9, except that the starting material was changed from N-Boc-glycine to Boc-β-alanine. Pentafluorophenol 4-nitroxybutyrate in preparation step 2 was changed to pentafluorophenol 3-nitroxypropionate. The structure was confirmed by $^1$H NMR and mass spectrometry.

$^1$H NMR (400 MHz, CDCl$_3$) δ: 9.96 (s, 1H), 8.95 (s, 1H), 7.75 (s, 2H), 6.77 (d, J=2.9 Hz, 1H), 6.55 (d, J=3.1 Hz, 1H), 4.78 (t, 2H), 4.28-4.22 (m, 4H), 3.86 (d, 6H), 2.52 (t, 2H), 2.33 (t, 2H), 2.12 (s, 6H); LC-MS: m/z (ES$^+$), 559 [M+1]$^+$.

Example 13: Preparation of 2-[4-(5,7-dimethoxy-4-oxo-3,4-dihydro-quinazolin-2-yl)-2,6-dimethyl-phenoxy]-ethyl (2-oxo-4-phenyl-furazan-3-yl)-methyl 2-hydroxy succinate (H113)

The preparation method was the same as that of Example 6, except that the succinic anhydride in step 1 of Example 6 was replaced by 2-hydroxysuccinic acid, and the one in step 3 of Example 6 was replaced by (2-oxo-4-phenyl-furazan-3-yl)-methanol. The resulting structure was confirmed by $^1$H NMR and mass spectrometry.

$^1$H NMR (400 MHz, DMSO-d$_6$) δ: 11.81 (s, 1H), 7.89 (m, 2H), 7.78-7.62 (m, 6H), 6.73 (s, 1H), 6.59 (d, J=3.1 Hz, 1H), 5.56 (s, 1H), 4.80 (s, 1H), 4.42-4.35 (m, 2H), 4.01-3.93 (m, 2H), 3.91 (d, 6H), 2.87-2.70 (m, 2H), 2.35 (s, 6H). LC-MS: m/z (ES$^+$), 661 [M+1]$^+$.

Example 14: Preparation of 4-(2-(((2-(4-(5,7-dimethoxy-4-oxo-3,4-dihydro-quinazolin-2-yl)-2,6-dimethyl-phenoxy)ethoxy) carbonyl)oxy)ethoxy)-3-(phenylsulfonyl)-2-oxo-furazan (H114)

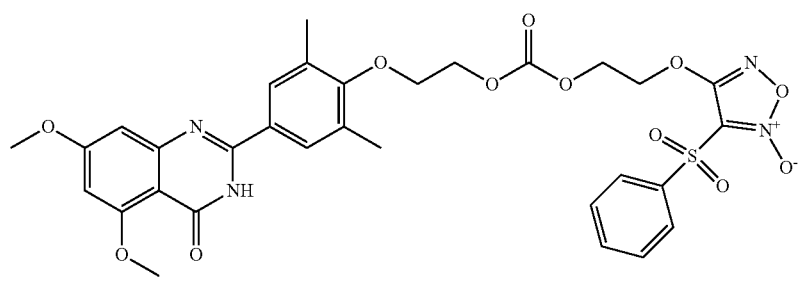 [SMILES: COc1cc(OC)c2c(=O)[nH]c(-c3cc(C)c(OCCOC(=O)OCCOc4no[n+]([O-])c4S(=O)(=O)c4ccccc4)c(C)c3)nc2c1]

3-[(4-phenylsulfonyl-5-oxo-furan-3-yl)-oxy]-propanol (143 mg, 0.5 mmol), triethylamine (101 mg, 1 mmol), and DCM (20 mL) were added into a 50 mL flask. The product obtained in step 3 of Example 3 (216 mg, 0.5 mmol) was then added. The mixture was stirred at room temperature for 3 h. After the completion of the reaction detected by TLC, the mixture was filtered. The resulting filtrate was distilled under reduced pressure. The resulting crude product was purified by silica gel column chromatography (eluent:dichloromethane:methanol=9:1) to give 88 mgof the target compound (H114), yield 26%. Its structure was confirmed by $^1$H NMR and mass spectrometry.

$^1$H NMR (400 MHz, DMSO-$d_6$) δ: 11.82 (s, 1H), 8.21 (d, 2H), 7.88 (m, 1H), 7.79 (m, 2H), 6.85 (s, 1H), 6.62 (s, 1H), 4.62-4.49 (m, 8H), 3.87 (d, 6H), 2.32 (s, 6H). LC-MS: m/z (ES$^+$), 683 [M+1]$^+$.

Example 15: Preparation of 2-[4-(5,7-dimethoxy-4-oxo-3,4-dihydro-quinazolin-2-yl)-2,6-dimethyl-phenoxy]-ethyl (E)-4-((furan-2-sulfonylamino)oxy)-4-oxo-2-crotonate (H115)

The preparation method is the same as that of Example 6, except that the succinic anhydride in Step 1 of Example 6 was replaced by butenedioic acid, and the one in step 3 of Example 6 was replaced by N-hydroxythiophene-2-sulfonamide (the preparation method of N-hydroxythiophene-2-sulfonamide referred to the patent WO2014113700). The resulting structure was confirmed by $^1$H NMR and mass spectrometry.

$^1$H NMR (400 MHz, DMSO-$d_6$) δ: 11.81 (s, 1H), 7.91 (d, 1H), 7.69 (m, 2H), 7.69 (m, 4H), 7.4 (s, 1H), 6.78 (d, J=3.6 Hz, 1H), 6.54 (d, J=2.9 Hz, 1H), 6.36 (s, 2H), 4.48-4.37 (m, 2H), 3.91 (d, 6H), 2.35 (s, 6H). LC-MS: m/z (ES$^+$), 614 [M+1]$^+$.

Example 16: Preparation of 2-[4-[5,7-dimethoxy-4-oxo-3,4-dihydro-quinazolin-2-yl)-2,6-dimethyl-phenoxy]-ethyl 4-(((3-(methylsulfonyl))phenyl)sulfonylamino)oxy)-4-oxo-butyrate (H116)

Step 1

Methylsulfonylbenzene (5 g, 32 mmol) was placed into chlorosulfonic acid (37 g, 320 mmol), heated at 90° C. for 18 h, and cooled to room temperature. The mixture was slowly poured into crushed ice. The resulting suspension was extracted with ethyl acetate (2×200 mL). The organic layers were separated, combined, washed with saturated aqueous NaCl solution (50 mL), and dried with sodium sulfate. After suction filtration, the resulting filtrate was distilled under reduced pressure. The residue was the intermediate 3-methylsulfonylphenyl-1-sulfonyl chloride (50 mg, yield 6.1%).

Step 2

Aqueous hydroxylamine solution (50 mmol) was dissolved in THF (60 mL) and water (10 mL), cooled to −5° C. 3-methylsulfonylphenyl-1-sulfonyl chloride (5.1 g, 20 mmol) was slowly added, while the reaction temperature was kept not higher than 10° C. Under the low temperature, DCM (100 mL) was added into the mixture after the completion of the reaction. The organic layer was collected, and washed with water (2×50 mL). The resulting separated organic layer was dried with sodium sulfate. After suction filtration, the filtrate was distilled under reduced pressure to give the intermediate N-hydroxy-3-(methylsulfonyl) benzsulfamide (3 g, yield 60%).

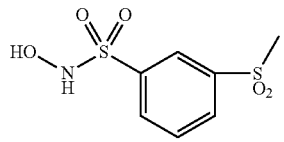

Step 3

The product from the previous step (427 mg, 1.7 mmol), triethylamine (172 mg, 1.7 mmol), and DCM (20 mL) were added into a 50 mL flask. The intermediate prepared in Step 8 of Example 4 (416 mg, 0.85 mmol) was dissolved in DCM (20 mL), and added dropwise into the reaction mixture at 0° C., and then stirred for 1 h. After the completion of the reaction detected by TLC, the mixture was washed with water, dried with sodium sulfate, and suction filtration. The filtrate was then distilled under reduced pressure. The resulting crude product was purified by silica gel column chromatography (eluent: dichloromethane:methanol=80:1) to give 120 mgof the target compound 2-[4-(5,7-dimethoxy-4-oxo-3,4-dihydro-quinazolin-2-yl)-2,6-dimethyl-phenoxy]-ethyl 4-(((3-(methylsulfonyl)phenyl)sulfonylamido)oxy)-4-oxo-butyrate (H116), yield 20%. Its structure was confirmed by $^1$H NMR and mass spectrometry.

$^1$H NMR (400 MHz, DMSO-$d_6$) δ: 11.86 (s, 1H), 11.52 (s, 1H), 8.38-8.23 (m, 3H), 8.00-7.89 (m, 3H), 6.74 (d, J=2.3 Hz, 1H), 6.52 (d, J=2.3 Hz, 1H), 4.38-4.31 (m, 2H), 4.05-3.99 (m, 2H), 3.87 (d, 6H), 3.35 (s, 3H), 2.66 (m, 4H), 2.29 (s, 6H). LC-MS: m/z (ES$^+$). 703 [M+1]$^+$.

Example 17: Preparation of 2-[4-(5,7-dimethoxy-4-oxo-3,4-dihydro-quinazolin-2-yl)-2,6-dimethyl-phenoxy]-ethyl 4-[4-(2-(nitroxy)ethyl)-piperazin-1-ly]-4-oxo-butyrate (H117)

The preparation method was the same as that in Step 3 of Example 16, except that the starting material was changed from N-hydroxy-3-(methylsulfonyl) benzsulfamide to 1-(2-(nitroxy)ethyl)-piperazine). The structure of the final product was confirmed by mass spectrometry.

$^1$H NMR (400 MHz, DMSO-$d_6$) δ: 11.83 (s, 1H), 7.88 (s, 2H), 6.70 (d, J=2.9 Hz, 1H), 6.54 (d, J=2.8 Hz, 1H), 4.36-4.30 (m, 2H), 4.11-4.05 (m, 2H), 3.84 (d, 6H), 3.67 (m, 2H), 3.44 (m, 4H), 2.68-2.54 (m, 10H), 2.35 (s, 6H). LC-MS: m/z (ES$^+$), 703 [M+1]$^+$.

Example 18: Preparation of 1-(2,3-dinitroxy-propyl) 4-{2-[4-(5,7-dimethoxy-4-oxo-3,4-dihydro-quinazolin-2-yl)-2,6-dimethyl-phenoxy]-ethyl}2-aminosuccinate hydrochloride (H118)

Step 1

2,3-dibromo-1-propanol (2 g, 9.2 mmol), silver nitrate (15.6 g, 91.8 mmol), and CH$_3$CN (100 mL) were mixed, and stirred at room temperature for 2 days. After the completion of the reaction detected by TLC, the mixture was diluted with water (50 mL) added therein, and extracted with ethyl acetate (3×50 mL). The organic layers were separated, and combined. The combined organic layer was dried with sodium sulfate, and suction filtration under reduced pressure. The resulting filtrate was distilled under reduced pressure. The crude product was purified by silica gel column chromatography (eluent: petroleum ether:ethyl acetate=4:1) to give 2,3-dinitroxy-1-propanol (0.5 g, yield 30%).

Step 2

The intermediate H130 (2.22 g, 59.9 mmol), H18-7 (1.94 g, 59.9 mmol), DCC (1.86 g, 90 mmol), DMAP (1.1 g, 1.1 mmol), and THF (60 mL) were added into a 100 mL flask. The mixture was stirred overnight at room temperature. After the completion of the reaction detected by TLC, DCM (50 mL) was added to obtain a suspension. The suspension was filtered. The filtrate was washed with water, then dried with sodium sulfate, and suction filtration under reduced pressure. The resulting filtrate was distilled under reduced pressure. The crude product was purified by silica gel column chromatography (eluent: dichloromethane:methanol=100:1) to give H18-8 (4.1 g, 6.07 mmol, yield 100%).

Step 3

H18-8 (4 g, 5.9 mmol), palladium carbon Pd/C (200 mg), and methanol (200 mL) were added into a 500 mL flask, replacing with hydrogen gas under vacuum. The mixture was stirred under hydrogen gas overnight. After the completion of the reaction detected by TLC, the mixture was filtrated. The resulting filtrate was dried under vacuum to give the intermediate H18-9 (2.5 g, yield 72.4%).

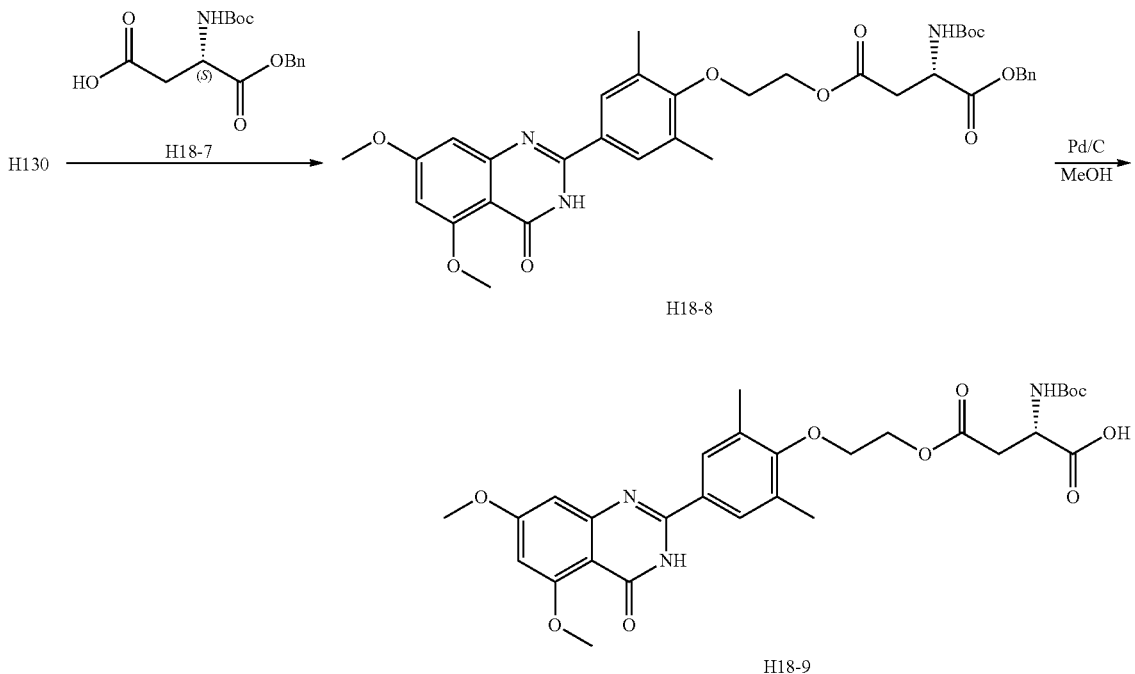

Step 4

H18-9 (585.6 mg, 1 mmol), the product prepared in step 1 (182.09 mg, 1 mmol), DCC (309 mg, 1.5 mmol), HOBt (202.5 mg, 1.5 mmol), DMAP (183 mg, 1.5 mmol), and THF (20 mL) were added into a 100 mL flask. The resulting mixture was stirred overnight at room temperature. After the completion of the reaction detected by TLC, the mixture was filtered. Water (20 mL) and DCM (20 mL) were added into the filtrate. The organic layer was separated, and distilled under reduced pressure. The resulting crude product was purified by silica gel column chromatography (eluent:dichloromethane:methanol=100:1) to give the intermediate H18-11 (300 mg, yield 40%).

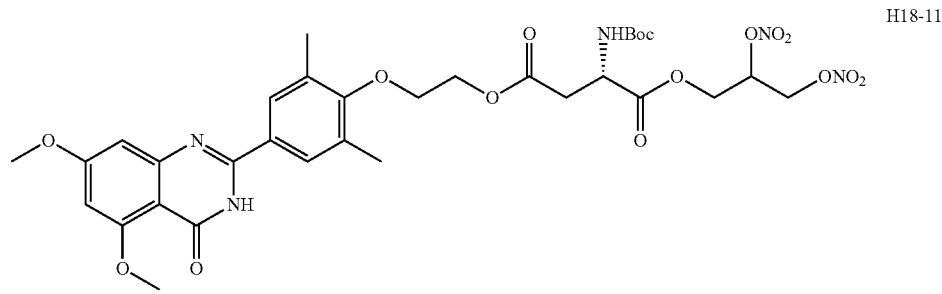

Step 5

The product from the previous step (280 mg, 0.37 mmol) was dissolved in ethyl acetate (30 mL). HCl/EtOAc (100 mL) was added dropwise into the solution. The mixture was stirred at room temperature for 2 h, and filtered. The filtrate was discarded. The resulting residue was dried under vacuum to give 150 mg of the target compound (H118), 1-(2,3-dinitroxy-propyl) 4-{2-[4-(5,7-dimethoxy-4-oxo-3,4-dihydro-quinazolin-2-yl)-2,6-dimethyl-phenoxy]-ethyl}2-amino-succinate, yield 59%. Its structure was confirmed by $^1$H NMR and mass spectrometry.

$^1$H NMR (400 MHz, DMSO-$d_6$) δ: 8.73 (s, 3H), 7.90 (s, 2H), 6.83 (s, 1H), 6.57 (s, 1H), 5.75-5.62 (m, 1H), 5.03-4.95 (m, 1H), 4.87 (d, J=6.2 Hz, 1H), 4.65-4.40 (m, 5H), 4.07 (s, 2H), 3.88 (d, 6H), 3.11 (m, 2H), 2.31 (s, 6H); LC-MS: m/z (ES$^+$), 649 [M+1]$^+$.

Example 19: Preparation of 2-[4-(5,7-dimethoxy-4-oxo-3,4-dihydro-quinazolin-2-yl)-2,6-dimethyl-phenoxy]-ethyl (6-nitroxy-hexahydrofuro[3,2-b]furan-3-yl)-carbonate (H119)

The intermediate H04-7 (53.6 mg, 0.1 mmol), isosorbide mononitrate (38 mg, 0.2 mmol), DMAP (18.4 mg, 0.15 mmol), and DCM (5 mL) were added into a 10 mL flask, and stirred at room temperature overnight. After the completion of the reaction detected by TLC, the product was washed with water, then dried with sodium sulfate, and suction filtration under reduced pressure. The resulting filtrate was distilled under reduced pressure. The resulting crude product was purified by silica gel column chromatography (eluent: dichloromethane:methanol=100:1) to give 35 mg of the target compound H119:
2-[4-(5,7-dimethoxy-4-oxo-3,4-dihydro-quinazolin-2-yl)-2,6-dimethyl-phenoxy]-ethyl(6-nitroxy-hexahydrofuro[3,2-b]furan-3-yl)-carbonate, yield 60%. Its structure was confirmed by $^1$H NMR and mass spectrometry.

$^1$H NMR (400 MHz, DMSO-$d_6$) δ: 11.85 (s, 1H), 7.90 (s, 2H), 6.74 (d, J=2.0 Hz, 1H), 6.52 (d, J=2.1 Hz, 1H), 5.52 (td, J=5.3, 1.6 Hz, 1H), 5.06-4.99 (m, 2H), 4.52-4.42 (m, 3H), 4.08-3.98 (m, 4H), 3.90-3.80 (m, 8H), 2.28 (s, 6H). LC-MS: m/z (ES$^+$), 587 [M+1]$^+$.

Example 20: Preparation of 2-[4-(5,7-dimethoxy-4-oxo-3,4-dihydro-quinazolin-2-yl)-2,6-dimethyl-phenoxy]-ethyl (6-nitroxy-hexahydrofuro[3,2-b]furan-3-yl)-carbamate (H120)

The preparation method was the same as that of Example 19, except that the starting material isosorbide mononitrate was replaced by 6-nitroxy-hexahydrofuro [3,2-b]furan-3-yl-amino Its structure was confirmed by $^1$H NMR and mass spectrometry.

$^1$H NMR (400 MHz, DMSO-$d_6$) δ: 11.72 (s, 1H), 8.04 (s, 1H), 7.81 (s, 2H), 6.71 (m, 2H), 6.59 (d, J=3.4 Hz, 1H), 5.48 (td, J=4.3, 1.9 Hz, 1H), 5.12-4.92 (m, 2H), 4.47-4.38 (m, 3H), 4.13-3.92 (m, 4H), 3.85-3.73 (m, 8H), 2.31 (s, 6H). LC-MS: m/z (ES$^+$), 586 [M+1]$^+$.

The preparation method of 6-nitroxy-hexahydrofuro[3,2-b]furan-3-yl-amino was as follows:

Step 1

28.0 g of NaN$_3$ was dissolved in 160 mL of chloroform, and cooled to 0° C. under stirring. Then 10 mL of concentrated sulfuric acid was slowly added dropwise. The mixture was then reacted for 2.5 h, and filtered. The filtrate was dried with sodium sulfate to give hydrazoic acid.

Step 2

12.6 g of triphenyl phosphine and 8.4 g of isosorbide mononitrate were dissolved in 100 mL of anhydrous tetrahydrofuran (THF), stirred, and cooled to 0° C. The chloroform solution of the product obtained in the previous step (100 mL) was added dropwise in portions, with 20 mL each portion. After the completion of the addition, the reaction continued for another 30 min. 8.6 mL solution of diisopropyl azodicarboxylate (DIAD) in THF (20 mL) was added dropwise in portions into the reaction solution. After the reaction continued for another 5 h, the mixture was returned to room temperature, and then heated to 60° C. in an oil bath, and then reacted for another 28 h. 8 mL of distilled water was added. 2M HCl was added to adjust the pH of the reaction solution to 1-2. Then the reaction solution was extracted 3 times with anhydrous dichloromethane, with 30 mL each time. The dichloromethane layers were combined, and washed with distilled water (3×15 mL), dried with sodium sulfate, and filtrated. The solvent in the filtrate was evaporated with a rotary evaporator to give 6-nitroxy-hexahydrofuro[3,2-b] furan-3-yl-amino.

Example 21: Preparation of 2-[4-(5,7-dimethoxy-4-oxo-3,4-dihydro-quinazolin-2-yl)-2,6-dimethyl-phenoxy]-ethyl 4-(((5-chlorothiophene)-2-sulfonylamino)oxy)-4-oxo-butyrate (H121)

N-hydroxy-5-chlorothiophene-2-sulfonamide (362 mg, 1.7 mmol, the preparation method referred to patent WO2014113700), triethylamine (172 mg, 1.7 mmol), and DCM (20 mL) were added into a 50 mL flask. The intermediate prepared in step 2 of Example 6 (416 mg, 0.85 mmol) was dissolved in DCM (20 mL), added dropwise into the reaction mixture at 0° C., and stirred for 1 h. After the completion of the reaction detected by TLC, the reaction mixture was washed with water, dried with sodium sulphate, and suction filtration. The filtrate was distilled under reduced pressure. The resulting crude product was purified by silica gel column chromatography to give 147 mg of the target compound 2-[4-(5,7-dimethoxy-4-oxo-3,4-dihydro-quinazolin-2-yl)-2,6-dimethyl-phenoxy]-ethyl 4-(((5-chlorothiophene)-2-sulfonylamino)oxy)-4-oxo-butyrate (H116), yield 26%. Its structure was confirmed by $^1$H NMR and mass spectrometry.

$^1$H NMR (400 MHz, DMSO-$d_6$) δ: 11.86 (s, 1H), 7.97 (s, 1H), 7.64 (m, 2H), 6.71 (d, J=2.5 Hz, 1H), 6.55 (d, J=3.1 Hz, 1H), 4.45-4.36 (m, 2H), 4.05-3.99 (m, 2H), 3.87 (d, 3H), 2.69 (m, 4H), 2.28 (s, 6H). LC-MS: m/z (ES$^+$), 666 [M+1]$^+$.

Example 22: Preparation of 2-(N-((2-(4-(5,7-dimethoxy-4-oxo-3,4-dihydro-quinazolin-2-yl)-2,6-dimethyl-phenoxy]-ethoxy) carbonyl)oxy)sulfamoyl)-1-methyl-1H-pyridine 1-2-onium salt (H122)

The preparation method was the same as that of Example 21, except that the starting material was changed from N-hydroxy-5-chlorothiophene-2-sulfonamide to 2-(N-hydroxyaminosulfonyl)-1-methyl-1H-pyrazole-2-onium salt (the preparation method referred to the patent WO2014113700). The structure of the resulting target compound is confirmed by $^1$H NMR and mass spectrometry.

$^1$H NMR (400 MHz, DMSO-$d_6$) δ: 11.83 (s, 2H), 11.56 (s, 1H), 7.93 (s, 1H), 7.82 (d, 2H), 7.67 (d, J=3.2 Hz, 2H), 6.76 (d, J=2.5 Hz, 1H), 6.53 (d, J=2.3 Hz, 1H), 4.55-4.52 (m, 2H), 4.08-4.02 (m, 2H), 3.89 (d, 6H), 2.48 (s, 3H), 2.25 (s, 6H). LC-MS: m/z (ES$^+$), 575 [M+1]$^+$.

Example 23: Preparation of 3,4-(dinitroxy) butyl 2-acetamino-3-(4-(((2-(4-(5,7-dimethoxy-4-oxo-3,4-dihydro-quinazolin-2-yl)-2,6-dimethyl-phenoxy]-ethoxy) carbonyl)oxy)phenyl)propionate (H123)

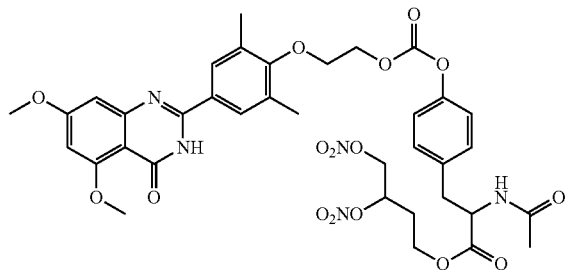

Step 1

Boc-(L)-tyrosine (380 mg, 1.35 mmol) was dissolved in a solution of N, N-dimethylformamide (10 mL). Cesium carbonate (440 g, 1.35 mmol) was added. A solution of 3,4-dinitroxy-1-bromobutane (350 mg, 1.35 mmol, the preparation method referred to WO 2001049275) dissolved in dichloromethane (20 mL) was added dropwise into the mixture at 0° C. The mixture was stirred at 0° C. for 20 min, slowly warmed up to room temperature, and stirred for another 22 h. 5% aqueous solution of sodium dihydrogen phosphate (20 mL) was added. The mixture was extracted with diethyl ether (4×20 mL). The resulting organic layer was dried with sodium sulfate, and distilled under reduced pressure. The residue was purified by silica gel column chromatography (gradient elution with eluent: n-hexane/ethyl acetate) to give the intermediate 3,4-(dinitroxy) butyl 2-(tert-butoxycarbonylamino)-3-(4-hydroxyphenyl)propionate (267 mg, 43% yield).

Step 2

The product from the previous step (0.97 g, 2.12 mmol) was dissolved in dichloromethane (20 mL) to form a solution. HCl gas was introduced into the solution for 3 hours. Then dichloromethane (25 mL) was added. The mixture was washed with saturated aqueous solution of sodium carbonate. The organic layer was separated, dried with sodium sulfate, and distilled under reduced pressure to give the intermediate 3,4-(dinitroxy) butyl 2-amino-3-(4-hydroxyphenyl) propionate.

Step 3

The product from the previous step (0.66 g, 1.85 mmol) was dissolved in dichloromethane solution (15 mL). Then triethylamine (0.25 mL, 1.85 mmol) was added. The reactants were cooled to 0° C. and acetyl chloride (0.14 mL, 1.98 mmol) was added dropwise thereto. The reactants were stirred at 0° C. for 10 min, and then at room temperature for 16 h, and dichloromethane (25 mL) was added thereto. The mixture was washed with water. The resulting organic layer was dried with sodium sulfate, and distilled under reduced pressure. The residue was purified by silica gel column chromatography (gradient elution with eluent: n-hexane/ethyl acetate) to give the intermediate 3,4-(dinitroxy) butyl 2-acetamino-3-(4-hydroxyphenyl) propionate (341 mg, yield 46%).

Step 4

The product from the previous step (0.46 g, 1.15 mmol) was dissolved in dichloromethane (8 mL). Pyridine (0.11 mL, 1.15 mmol) was then added. The reactants were cooled to 0° C. Then p-nitrophenyl chloroformate (233 mg, 1.15 mmol) was added. The reactants were stirred at 0° C. for 15 min, and then at room temperature for 48 h. Dichloromethane (20 mL) was added. The mixture was washed with aqueous solution of HCl (1 M, 20 mL), and then washed with saturated aqueous sodium carbonate solution. The organic layer was dried with sodium sulfate, and distilled under reduced pressure. The residue was purified by silica gel column chromatography (gradient elution with eluent: n-hexane/ethyl acetate) to give the intermediate 3,4-(dinitroxy)-butyl 2-acetylamino-3-(4-nitrophenoxy)carbonyloxy)phenyl) propionate (228 mg, yield 35%).

Step 5

The product from the previous step (453 mg, 0.8 mmol) was dissolved in dichloromethane (15 mL). Then scandium triflate (0.04 g, 0.09 mmol) and DMAP (0.21 g, 1.8 mmol) were added. The reactants were cooled to 0° C. The intermediate H130 (296 mg, 0.8 mmol) was added. The reactants were stirred at room temperature for 18 h. Dichloromethane (24 mL) was added. The mixture was washed with 5% of sodium dihydrogen phosphate solution, and then washed with saturated aqueous sodium carbonate solution. The organic layer was dried with sodium sulfate, and distilled under reduced pressure. The residue was purified by silica gel column chromatography (gradient elution with eluent: n-hexane/ethyl acetate) to give the target compound (204 mg, yield 32%). The structure of the resulting target compound was confirmed by $^1$H NMR and mass spectrometry.

$^1$H NMR (400 MHz, DMSO-$d_6$) δ: 11.81 (s, 1H), 7.89 (s, 2H), 7.52-6.74 (m, 4H), 6.73 (d, J=2.8 Hz, 1H), 6.57 (d, J=2.7 Hz, 1H), 4.58-4.53 (m, 3H), 4.11-4.05 (m, 2H), 3.98 (m, 2H), 3.91 (s, 3H), 3.88-3.82 (t, 5H), 3.58-3.52 (m, 1H), 3.49-3.40 (m, 2H), 2.29 (s, 6H), 1.95 (m, 3H). LC-MS: m/z (ES+), 798 [M+1]+.

Example 24: Preparation of 3-(nitroxy)-2,2-di(nitroxymethyl) propyl 4-(2-[4-(5,7-dimethoxy-4-oxo-3,4-dihydro-quinazolin-2-yl)-2,6-dimethyl-phenoxy] butyl)-4-oxo-2-acetamino-butyrate (H124)

Step 1

The intermediate H130 (1.3 g, 3.5 mmol) was dissolved in acetone (100 mL) to form a solution. Then N-acetyl aspartic acid (1.09 g, 6.25 mmol) and DMAP (catalytic amount) were added. The reactants were cooled to 0° C. EDAC (1.19 g, 6.25 mmol) was added. The reactants were stirred at room temperature for 24 h, and distilled under reduced pressure. The residue was purified by silica gel column chromatography (gradient elution with eluent: dichloromethane/methanol) to give 4-(2-[4-(5,7-dimethoxy-4-oxo-3,4-dihydro-quinazolin-2-yl)-2,6-dimethyl-phenoxy] butyl)-4-oxo-2-acetamino-butyric acid (0.83 g, yield 45%).

Step 2

The product from the previous step (0.66 g, 1.25 mmol) was dissolved in dichloromethane (30 mL). Then 3-chloro-2,2-di(chloromethyl) propane-1-ol (0.24 g, 1.25 mmol) and DMAP (catalytic amount) were added. The reactants were cooled to 0° C. EDAC (0.24 g, 1.25 mmol) was then added. The reactant was stirred at room temperature for 24 h, and distilled under reduced pressure. The residue was purified by silica gel column chromatography (gradient elution with eluent: N-hexane/ethyl acetate) to give 3-chloro-2,2-di(chloromethyl) propyl 4-(2-[4-(5,7-dimethoxy-4-oxo-3,4-dihydro-quinazolin-2-yl)-2,6-dimethyl-phenoxy] butyl)-4-oxo-2-acetamino-butyrate (0.57 g, yield 65%).

Step 3

The product from the previous step (525 mg, 0.75 mmol) was dissolved in acetonitrile (20 mL). Then sodium iodide (0.45 g, 3.06 mmol) was added. The reactants were heated to 120° C. under microwave irradiation, standing for 60 min. The resulting mixture was cooled, and filtered. The resulting organic layer was distilled under reduced pressure to give the intermediate 3-iodo-2,2-di(iodomethyl) propyl 4-(2-[4-(5,7-dimethoxy-4-oxo-3,4-dihydro-quinazolin-2-yl)-2,6-dimethyl-phenoxy]butyl)-4-oxo-2-acetamino-butyrate (417 mg, yield 57%).

Step 4

The product from the previous step (0.6 g, 0.62 mmol) was dissolved in acetonitrile (20 mL) to form a solution. Silver nitrate (405 mg, 2.43 mmol) was added. The reactants were heated to 120° C. under microwave irradiation, standing for 5 min. The resulting mixture was cooled, and filtrated. The resulting organic layer was distilled under reduced pressure. The residue was then purified by silica gel column chromatography (gradient elution with eluent: n-hexane/ethyl acetate) to give the target compound (232 mg, yield 48%). The structure of the resulting target compound was confirmed by $^1$H NMR and mass spectrometry.

$^1$H NMR (400 MHz, DMSO-$d_6$) δ: 11.86 (s, 1H), 8.58 (s, 1H), 7.94 (s, 2H), 6.81 (s, 1H), 6.55 (s, 1H), 5.93-5.85 (m, 1H), 4.42-4.36 (m, 2H), 4.03 (m, 2H), 3.87-3.81 (m, 8H), 3.39 (s, 6H), 3.09-3.01 (m, 2H), 2.34 (s, 6H), 1.89 (s, 3H). LC-MS: m/z (ES$^+$) 781 [M+1]$^+$.

Example 25: Preparation of 2-nitroxyethyl 4-(2-[4-(5,7-dimethoxy-4-oxo-3,4-dihydro-quinazolin-2-yl)-2,6-dimethyl-phenoxy]butoxy)-4-oxo-2-(2-(nitroxy) acetamino)-butyrate (H125)

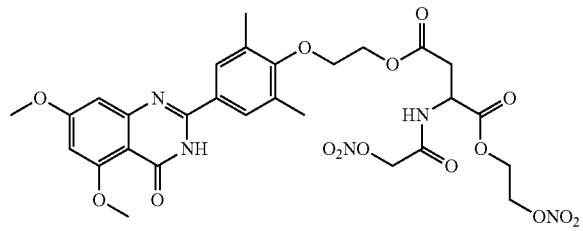

Step 1

The intermediate H130 (2.11 g, 5.7 mmol) was dissolved in dichloromethane (100 mL) to form a solution. 4-(allyloxy)-3-(tert-butoxycarbonylamino)-4-oxobutanoic acid (1.55 g, 5.7 mmol) and DMAP (catalytic amount) were added. The reactants were cooled to 0° C. Then EDAC (1.49 g, 7.85 mmol) was added. The reactants were stirred at room temperature for 12 h, and distilled under reduced pressure. The residue was purified by silica gel column chromatography (gradient elution with eluent: n-hexane/ethyl acetate) to give the intermediate 2-allyl 4-(2-[4-(5,7-dimethoxy-4-oxo-3,4-dihydro-quinazolin-2-yl)-2,6-dimethyl-phenoxy] butyloxy)-4-oxo-2-(tert-butoxycarbonylamino) succinate (1.92 g, yield 54%).

Step 2

The product from the previous step (1.53 g, 2.45 mmol) was dissolved in dichloromethane (40 mL) to form a solution. HCl gas was introduced for 15 min. The mixture was distilled under reduced pressure to give the intermediate 2-allyl 4-(2-[4-5,7-dimethoxy-4-oxo-3,4-dihydro-quinazolin-2-yl)-2,6-dimethyl-phenyl] butyloxy)-4-oxo-2-amino butyrate hydrochloride (0.66 g, yield 48%).

Step 3

The product from the previous step (702 mg, 1.25 mmol) was dissolved in dichloromethane (80 mL) to form a solution. DMAP (143 mg, 1.2 mmol) and pentafluorophenol 2-nitroxyacetate (359 mg, 1.25 mmol, the preparation method referred to WO 2005011646). The reactants were stirred at room temperature for 12 h. The solvent was evaporated under reduced pressure. The residue was purified by silica gel column chromatography (gradient elution with eluent: n-hexane/ethyl acetate) to give the intermediate 2-allyl 4-(2-[4-5,7-dimethoxy-4-oxo-3,4-dihydro-quinazolin-2-yl)-2,6-dimethyl-phenoxy]butyloxy)-4-oxo-2-(2-(nitroxy)acetamino)-butyrate (495 mg, yield 63%).

Step 4

The product from the previous step (440 mg, 0.70 mmol) was dissolved in dichloromethane (20 mL) to form a solution. 5,5-dimethyl-1,3-cyclohexanedione (0.13 g, 0.97 mmol), triphenyl phasphine (0.30 g, 1.16 mmol), and tetrakis (triphenyl phosphine) palladium (0.045 g, 0.039 mmol) were added. The reactants were stirred at room temperature for 12 h. The solvent was evaporated under reduced pressure. The residue was purified by silica gel column chromatography (eluent: n-hexane/acetone/acetic acid 4/6/0.1%) to give the intermediate 4-(2-[4-(5,7-dimethoxy-4-oxo-3,4-dihydro-quinazolin-2-yl)-2,6-dimethyl-phenoxy]butoxy)-4-oxo-2-(2-(nitroxy)acetamino)-butyric acid (239 mg, yield 58%).

Step 5

The product from the previous step (265 mg, 0.45 mmol) was dissolved in dichloromethane (20 mL) to form a solution. 2-chloroethanol (0.04 mL, 0.5 mmol) and DMAP (catalytic amount) were added. The reactants were cooled to 0° C. Then EDAC (0.12 g, 0.62 mmol) was added. The reactants were stirred at room temperature for 12 h. The solvent was evaporated under reduced pressure. The residue was purified by silica gel column chromatography (gradient elution with n-hexane/ethyl acetate) give the intermediate 2-chloroethyl 4-(2-[4-(5,7-dimethoxy-4-oxo-3,4-dihydro-quinazolin-2-yl)-2,6-dimethyl-phenoxy]butoxy)-4-oxo-2-(2-(nitroxy)acetamino)-butyrate (186 mg, yield 65%).

Step 6

The product from the previous step (191 mg, 0.3 mmol) was dissolved in acetonitrile (10 mL) to form a solution. Sodium iodide (0.18 g, 1.25 mmol) was added. The reactants were heated to 120° C. under microwave irradiation, standing for 60 min. The resulting mixture was cooled, and filtrated. The resulting organic layer was distilled under reduced pressure to give the intermediate 2-iodine ethyl 4-(2-[4-(5,7-dimethoxy-4-oxo-3,4-dihydro-quinazolin-2-yl)-2,6-dimethyl-phenoxy]butyl oxy)-4-oxo-2-(2-(nitroxy) acetamino)-butyrate (95.5 mg, yield 46%).

Step 7

The product from the previous step (203 mg, 0.3 mmol) was dissolved in acetonitrile (10 mL) to form a solution. Silver nitrate (0.21 g, 1.24 mmol) was added. The reactants were heated to 120° C. under microwave irradiation, standing for 5 min. The resulting mixture was cooled, and filtrated. The resulting organic layer was distilled under reduced pressure. The residue was then purified by silica gel column chromatography (gradient elution with eluent:n-hexane/acetone) to give the target compound (115 mg, yield 58%). The structure of the resulting target compound was confirmed by $^1$H NMR and mass spectrometry. $^1$H NMR (400 MHz, DMSO-$d_6$) δ: 11.81 (s, 1H), 8.55 (s, 1H), 7.91 (s, 2H), 6.83 (s, 1H), 6.52 (s, 1H), 5.89-5.82 (m, 1H), 5.48 (s, 2H), 4.81 (t, 2H), 4.46-4.37 (m, 4H), 4.05 (m, 2H), 3.91 (d, 6H), 3.11-3.04 (m, 2H), 2.34 (s, 6H). LC-MS: m/z (ES$^+$) 678 [M+1]$^+$.

Biological Experiments

Experiment 1. Experimental Study on the Tested Compounds for Releasing Nitric Oxide in vitro Experimental Procedure:

(1) Preparation of Griess Reagent: 4 g of aminobenzenesulfonamide, 0.2 g of N-naphthyl ethylene diamine hydrochloride, and 10 mL of 85% phosphoric acid solution were taken to form a solution, which is diluted to 100 mL with distilled water.

(2) Plotting of the standard curve: a serie of standard solution of 0.01, 0.03, 0.05, 0.07, 0.09, 0.2, 0.4 μg/mL of nitrite nitrogen was prepared, 10 mL of each was taken to sufficiently mix with 2.5 mL of Griess reagent, standing at room temperature for 10 min, and its absorbance value at the wavelength of 540 nm was measured. The standard curve was plotted based on the resulting data.

(3) Measuring the amount of the released NO of the tested drug: all of the tested substances were dissolved in dimethylsulfoxide (1 mL) firstly. Then phosphate buffer (pH 7.4) was slowly added dropwise, and shaken. The drug solution was diluted to 50 mL, allowing the buffer solution to contain excess cysteine (5 mmol/L), and the final concentration of the tested substances being $10^{-4}$ mol/L; the solution was incubated at 37° C. 2 mL of the reaction solution was taken to mix with 500 μl of Griess reagent at 1 h respectively, standing at room temperature for 10 min. The absorbance value of the mixture at 540 nm was measured. Isosorbide mononitrate was used as a positive control, and H130 was used as a negative control. The amount of the released NO was represented by the amount of its oxidation product, nitrite ($NO_2^-$).

Experimental Results: The Results of the Released NO in vitro by the Tested Substances are Shown in Table 1.

Experimental conclusion: From the experimental results, it can be seen that NO releases with different levels can be detected within 1 h for all compounds expect H102 and H130. However, there are differences among the NO releasing rates of the NO providers having different structures. The releasing rate may be related to the molecular weight of the NO provider and the coupling manner of the NO provider to the original drug. Table 1 only shows the released NO detected at the time point of 1 h, wherein the compound H102 produces NO after 2 h or longer, although it does not produce NO within 1 h.

TABLE 1

| Tested Substance No. | Amount of Released No (μM) |
|---|---|
| Isosorbide Mononitrate | 3.31 |
| H101 | 5.97 |
| H102 | −0.55 |
| H106 | 2.56 |
| H108 | 0.33 |
| H109 | 1.49 |
| H111 | 52.12 |
| H113 | 45.63 |
| H117 | 1.36 |
| H118 | 1.74 |
| H119 | 1.24 |
| H120 | 1.32 |
| H124 | 2.89 |
| H130 (Negative Control) | −1.03 |

Experiment 2. Experimental study on the tested compounds for releasing HNO HNO rapidly dimerizes and dehydrates to produce nitrous oxide in aqueous solution. In the experiment of detecting HNO, gas chromatographic headspace analysis is generally used to determine the amount of the released nitrous oxide, thereby indirectly detect the level of releasing HNO of the compound.

Experimental procedure: Each of the tested compounds was prepared to 20 mg/mL of mother liquor with DMF. Prior to the start of the experiment, 50 μL of drug mother liquor was placed into a 20 mL headspace sample vial. The tested compound was diluted by adding 5 mL of PBS buffer with pH 7.4. The temperature of the resulting sample was kept at 37° C. under argon gas for 90 min. Then the top gas was extracted for gas chromatographic analysis of nitrous oxide by using Angeli's Salt as a positive compound in the experiment.

Experimental result: The result of the released HNO for each tested substance is shown in Table 2.

Experimental conclusion: Since the structures of the compounds selected in this experiment comprise HNO providers, no released NO in vitro can be detected for this kind of compounds. The level of released HNO can be only indirectly detected by determining the amount of the released nitrous oxide gas via gas chromatography headspace analysis. From the experimental result, it can be seen that no HNO release can be detected for the prototype compound H130 (negative control), and the HNO releases with different levels within 1.5 h can be detected for other compounds.

Experimental discussion: Nitroxyl or nitrosyl hydrogen (HNO) is a single electron reduction product of nitric oxide (NO). Studies have shown that they have positive inotropic effect on a living heart and can significantly improve the myocardial contractile function in patients with heart failure. Studies on mechanism reveal that HNO providers may regulate myocardial contractility in a redox-dependent manner. At present, the studies on HNO providers indicate that drugs containing HNO providers can be used to treat heart failure, such as acute congestive heart failure and early chronic heart failure. HNO provider drugs can also be administered together with positive inotropic drugs to patients undergoing β-antagonist treatment with heart failure. HNO provider drugs can also treat or prevent ischemia/reperfusion injuries, reduce the tissue infarct area of risky tissues, and can be used in organ transplant surgeries, which are completed by contacting an organ with a HNO provider before the reperfusion of the transplanted receptor organ.

TABLE 2

| Compound | Molar Quantities of $N_2O$/Sample (%) |
|---|---|
| Angeli's Salt | 62.4 |
| H103 | 19.7 |
| H104 | 23.6 |
| H115 | 17.8 |
| H116 | 15.3 |
| H121 | 24.6 |
| H122 | 18.3 |
| H130 (Negative Control) | −0.15 |

Experiment 3. Plasma Stability Experiment in vitro on the Tested Compounds

Experimental method: The tested compounds (2 μM) were added into mouse or human plasma, and incubated at 37° C. Samples were taken at 0, 10, 30, 60 and 120 min respectively. The reaction was stopped by adding a stop agent. The mixture was sufficient shaken, and centrifuged at 4000 rpm for 10 min at 4° C. The supernatant was taken. The concentrations of the tested compounds and their metabolite (H130) in the supernatant were measured by LC-MS/MS.

Experimental result: Changes in the plasma concentrations of tested compounds in vitro are shown in Table 3.

Experimental conclusion: The in vitro experimental result shows that the compound H101 has good stability in mouse and human plasma, and its concentration does not change significantly within 2 h. The compounds H102, H103, H104, H108, and H116 also have good stability in human plasma.

TABLE 3

| Tested Substance No. | Species/ Medium | Timepoint (min) | Content of Tested Substance (n = 2) | Content of H130 (n = 2) |
|---|---|---|---|---|
| H101 | CD-1 Mice/ Plasma | 0 | 100.0 | <1.5% |
| | | 10 | 101.4 | <1.5% |
| | | 30 | 94.8 | <1.5% |
| | | 60 | 99.7 | <1.5% |
| | | 120 | 99.1 | <1.5% |
| | Human/ Plasma | 0 | 100.0 | <1.5% |
| | | 10 | 99.5 | <1.5% |
| | | 30 | 96.4 | <1.5% |
| | | 60 | 97.5 | <1.5% |
| | | 120 | 95.8 | <1.5% |
| H102 | CD-1 Mice/ Plasma | 0 | 100.0 | <1.5% |
| | | 10 | 10.8 | 96.4 |
| | | 30 | 1.3 | 93.3 |
| | | 60 | 3.1 | 101.6 |
| | | 120 | 1.8 | 112.8 |
| | Human/ Plasma | 0 | 100.0 | <1.5% |
| | | 10 | 101.5 | <1.5% |
| | | 30 | 98.4 | 3.3 |
| | | 60 | 95.0 | 6.1 |
| | | 120 | 84.5 | 10.0 |
| H103 | CD-1 Mice/ Plasma | 0 | 100.0 | 71.1 |
| | | 10 | 0.0 | 113.1 |
| | | 30 | 0.0 | 106.1 |
| | | 60 | 0.0 | 113.8 |
| | | 120 | 0.0 | 121.3 |
| | Human/ Plasma | 0 | 100.0 | 51.8 |
| | | 10 | 97.3 | 53.2 |
| | | 30 | 89.6 | 55.2 |
| | | 60 | 83.3 | 54.6 |
| | | 120 | 86.9 | 58.9 |
| H104 | CD-1 Mice/ Plasma | 0 | 100.0 | 94.7 |
| | | 10 | 0.5 | 120.8 |
| | | 30 | 0.0 | 125.4 |
| | | 60 | 0.0 | 126.0 |
| | | 120 | 0.3 | 132.4 |
| | Human/ Plasma | 0 | 100.0 | 76.6 |
| | | 10 | 99.5 | 79.9 |
| | | 30 | 88.7 | 86.3 |
| | | 60 | 81.1 | 85.9 |
| | | 120 | 75.8 | 95.8 |
| H111 | CD-1 Mice/ Plasma | 0 | 100.0 | 5.1 |
| | | 10 | 1.9 | 54.6 |
| | | 30 | 1.1 | 76.5 |
| | | 60 | 1.3 | 103.6 |
| | | 120 | 0.2 | 115.8 |
| | Human/ Plasma | 0 | 100.0 | 4.1 |
| | | 10 | 53.1 | 11.7 |
| | | 30 | 15.1 | 19.6 |
| | | 60 | 2.0 | 26.7 |
| | | 120 | 0.2 | 32.8 |
| H116 | CD-1 Mice/ Plasma | 0 | 100.0 | <1.5% |
| | | 10 | 0.0 | 58.7 |
| | | 30 | 0.0 | 100.2 |
| | | 60 | 0.5 | 142.0 |
| | | 120 | 5.7 | 167.6 |
| | Human/ Plasma | 0 | 100.0 | <1.5% |
| | | 10 | 90.1 | <1.5% |
| | | 30 | 79.0 | 2.0 |
| | | 60 | 81.0 | 2.2 |
| | | 120 | 81.4 | 3.3 |

TABLE 3-continued

| Tested Substance No. | Species/ Medium | Timepoint (min) | Content of Tested Substance (n = 2) | Content of H130 (n = 2) |
|---|---|---|---|---|
| H108 | CD-1 Mice/ Plasma | 0 | 100.0 | 7.5 |
| | | 10 | 0.5 | 97.2 |
| | | 30 | 0.3 | 96.9 |
| | | 60 | 1.7 | 101.7 |
| | | 120 | 0.3 | 104.0 |
| | Human/ Plasma | 0 | 100.0 | 2.2 |
| | | 10 | 101.5 | 4.0 |
| | | 30 | 95.5 | 6.5 |
| | | 60 | 93.8 | 10.4 |
| | | 120 | 85.3 | 16.7 |
| H118 | CD-1 Mice/ Plasma | 0 | 100.0 | 30.8 |
| | | 10 | 0.0 | 82.4 |
| | | 30 | 0.0 | 81.8 |
| | | 60 | 0.0 | 89.0 |
| | | 120 | 0.0 | 89.6 |
| | Human/ Plasma | 0 | 100.0 | 18.4 |
| | | 10 | 96.3 | 20.7 |
| | | 30 | 75.2 | 28.2 |
| | | 60 | 61.9 | 36.4 |
| | | 120 | 33.1 | 52.0 |
| H119 | CD-1 Mice/ Plasma | 0 | 100.0 | 1.7 |
| | | 10 | 0.3 | 105.8 |
| | | 30 | 0.7 | 106.1 |
| | | 60 | 1.1 | 116.8 |
| | | 120 | 0.1 | 119.2 |
| | Human/ Plasma | 0 | 100.0 | <1.5% |
| | | 10 | 49.5 | 58.6 |
| | | 30 | 12.9 | 94.6 |
| | | 60 | 1.9 | 109.1 |
| | | 120 | 0.1 | 112.7 |

Experiment 4. Study on Pharmacokinetics and Bioavailability of Tested Compounds

Experimental method: Intravenous injection solutions (the administration concentrations of the tested compounds were 1 mg/kg) and oral gastric perfusates (the administration concentrations of the test compounds were 5 mg/kg) of the test compounds were prepared, and intravenously and orally administered to three SD rats, respectively. The concentrations of the whole blood for H130 at 0.083 h, 0.25 h, 0.5 h, 1 h, 2 h, 4 h, 8 h, and 24 h after administration were determined by LC-MS/MS, respectively. The pharmacokinetic parameters were compared by a drug-time curve. Sample pretreatment: 150 μL of the whole blood to be tested was aspirated accurately. 600 μL of internal standard solution (diluted to 0.5 μg/mL with methanol) was added, sufficiently mixed by a vortex mixer, and centrifuged at 13000 r/min for 20 min at 4° C. 3 μL of the supernatant was taken into a sample vial.

Chromatographic conditions: C18 reversed-phase chromatographic column; gradient elution with mobile phase A: water/acetonitrile (v:v=95:5) with 0.025% of formic acid and 1 mM of ammonium acetate added thereto, and mobile phase B: acetonitrile/water (v:v=95:5) with 0.025% of formic acid and 1 mM of ammonium acetate added thereto. The experimental results are shown in Tables 4 and 5, in which Table 4 shows the pharmacokinetic parameters for H130 after the intravenous injection of each tested compound in the rats, and Table 5 shows the pharmacokinetic parameters for H130 after oral administration of the original drug and various test compounds to the rats. Experimental conclusion: The experimental results indicate that after the administration of H101, H111, H116, H118, and H119, the prototype compound H130 can be rapidly released. This prototype compound H130 has been clinically proven to be a new drug that can be used to reduce the incidence of adverse cardiac events, and has high safety.

TABLE 4

| Pharmacokinetic Parameters | H130 | H101 | H111 | H116 | H118 | H119 |
|---|---|---|---|---|---|---|
| $T_{max}$ (h) | 0.0833 | 0.833 | 0.139 | 0.139 | 0.083 | 0.139 |
| $C_{max}$ (ng/mL) | 787 | 123 | 330 | 402 | 138 | 311 |
| $T_{1/2}$ (h) | 0.657 | 0.772 | 0.585 | 0.507 | 1.12 | 0.745 |
| $AUC_{0-t}$ (ng · h/mL) | 579 | 239 | 318 | 299 | 111 | 322 |
| $AUC_{Ratio}$ (Dosage Calibration)(%) | / | 37.7 | 54.9 | 51.6 | 19.2 | 55.6 |

TABLE 5

| Pharmacokinetic Parameters | H130 | H101 | H111 | H116 | H118 | H119 |
|---|---|---|---|---|---|---|
| $T_{max}$ (h) | 0.667 | 0.833 | 1.00 | 1.33 | 4.00 | 4.00 |
| $C_{max}$ (ng/mL) | 879 | 355 | 221 | 211 | 60.9 | 8.46 |
| $T_{1/2}$ (h) | 1.18 | 1.16 | 1.54 | 2.47 | ND | ND |
| $AUC_{0-t}$ (ng · h/mL) | 1657 | 786 | 693 | 751 | 234 | 13.9 |
| $AUC_{Ratio}$ (Dosage Calibration)(%) | / | 42.4 | 41.8 | 45.3 | 14.1 | 0.84 |

Experiment 5. Regulation of the Tested Compounds on ApoA-I mRNA HepG2 cells were cultured for 24 h in a 24-well plate with 400 μl of MEM medium containing 0.5% (v/v) of fetal bovine serum. Then each of the tested compounds (100 μM) and the positive control RVX-208 (100 μM) were added. The cells were cultured for another 48 h. The medium was aspirated out. After washing with 200 μl of PBS, 85 μl of cell lysis solution was added into the cells in each well. The cells were incubated at room temperature for 5 to 10 min to be completely dissolved and detached. The mRNA was extracted from the cells with a kit. The extracted mRNA were used for a real-time fluorescence quantitative PCR detection with RNA Fluorescence (RiboGreen) Quantitation Assay Kit and ApoA-I mRNA Primer-Probe Mixture from the company of Applied Biosystems.

After obtaining the Ct values, the induction fold of each test compound relative to DMSO control was calculated. The induction fold was used to reflect the ability of regulating ApoA-I mRNA for the tested compounds. When 100 μM of the tested compound allowed ApoA-I mRNA in HepG2 cells to increase more than 15%, then the test compound was known as an ApoA active compound.

The experimental results on regulating activity for each tested substance on ApoA-I mRNA in HepG2 cells are shown in Table 6. It can be seen from Table 6 that all of the synthesized tested substances can upregulate ApoA-I mRNA in liver cells. Apolipoprotein A-I (ApoA-I) is an important component of functional high-density lipoprotein (HDL) particles, and can effectively eliminate atherosclerotic plaque, prevent and treat hyperlipidemia, and improve blood glucose metabolism in vivo. Therefore, the fact that the compounds disclosed by the invention can increase intracellular ApoA-I level indicates that these compounds will play an active role in the prevention and treatment of cardiovascular diseases.

TABLE 6

| Tested Substance No. | Upregulation of Apoa-I Mrna Level |
|---|---|
| H101 | Active |
| H104 | Active |
| H106 | Active |
| H108 | Active |
| H109 | Active |
| H111 | Active |
| H116 | Active |
| H118 | Active |
| H119 | Active |

Experiment 6: Study on Effects of Tested Compounds on apoE−/− mouse atherosclerosis Models Experimental method: 36 eight-week-old male apoE−/− mice were selected and randomly divided into a blank administration group, an H101 administration group, an H111 administration group, an H116 administration group, an H119 administration group, and an H130 administration group, 6 mice per group. The mice in each group were fed with high-fat diet for 10 weeks. At the beginning of the high-fat feeding, the mice in each group were administrated. Each tested compound was intragastric administered at the dose of 150 mg/kg twice a day. The blank administration group was given corresponding dose of saline. The mice were fasted for more than 12 h, and 20% of urethane solution was used to anesthetize the mice before the mice were killed. After the blood was taken, the serum, heart, and aorta were isolated. The levels of total cholesterol (TC), high density lipoprotein cholesterol (HDL-C), and low density lipoprotein cholesterol (LDL-C) in the serum of the mice in each group were measured by automatic biochemical analyzer. The ApoA1 expression level was detected with an ApoA1 kit. The content of NO in the serum of the mice was determined with a total NO test kit (Beyotime). The NOS activities of the heart, aorta, and serum were determined with an NOS test kit (Beyotime). The content of eNOS was calculated by the difference between the measured values determined before and after adding eNOS inhibitor L-NAME (Beyotime).

The experimental results are shown in Table 7 and Table 8. Table 7 shows the blood lipid levels of the mice in each group after 10 weeks of high-fat diet. * $p<0.05$, and ** $p<0.01$, compared with the model group. Table 8 shows the NO and eNOS activity changes of the mice in each group after 10 weeks of high-fat diet.

TABLE 7

| Group | TC (mg/dL) | LDL-C (mg/dL) | HDL-C (mg/dL) | ApoA1 (%) |
|---|---|---|---|---|
| Blank Administration Group | 1397 ± 106 | 462 ± 43 | 50 ± 12 | 100 |
| H101Administration Group | 985 ± 68* | 273 ± 38 | 78 ± 9** | 126 |
| H111Administration Group | 1021 ± 57* | 296 ± 29* | 83 ± 13* | 118 |
| H116Administration Group | 1123 ± 73 | 315 ± 31** | 74 ± 11 | 128 |
| H119Administration Group | 994 ± 85* | 308 ± 35* | 88 ± 14* | 114 |
| H130Administration Group | 1005 ± 44* | 273 ± 33* | 86 ± 13* | 130 |

TABLE 8

| Group | Heart eNOS (%) | Aorta eNOS (%) | Serum eNOS (%) | Serum NO (%) |
|---|---|---|---|---|
| Blank Administration Group | 100 | 100 | 100 | 100 |
| H101 Administration Group | 135 | 132 | 128 | 126 |
| H111 Administration Group | 145 | 127 | 132 | 134 |
| H116 Administration Group | 148 | 136 | 123 | 138 |
| H119 Administration Group | 138 | 124 | 126 | 127 |
| H130 Administration Group | 115 | 105 | 107 | 108 |

Experimental conclusion: After the administration of each tested compound, compared with the mice in the blank administration group, TC and LDL-C values in the serum of the apoE−/− mice after 10 weeks of high-fat diet were significantly decreased, the HDL-C and ApoA1 were significantly increased, the eNOS activity of the heart, serum and aorta were increased, and the released NO in the serum increased.

Experimental discussion: Endothelial dysfunction is the first step in atherosclerosis. Endothelial dysfunction in vivo leads to abnormal vasoconstriction, increased endothelial permeability, platelet adhesion and aggregation, and leukocyte adhesion. The low density lipoprotein (LDL) transfers to the intima to form thrombosis, inflammatory response, abnormal proliferation and migration of smooth muscle cells, thereby promoting the formation of atherosclerosis. Nitric oxide (NO) synthesized by endothelial nitric oxide synthase (eNOS) can regulate vascular tone, act as an anti-oxidant, prevent the production of oxidized low density lipoprotein (ox-LDL) and inhibit the expression of adhesion molecules by activated endothelial cells, reduce the adhesion and activation of inflammatory cells; inhibit platelet adhesion, aggregation; effectively inhibit the proliferation and migration of vascular smooth muscle cells and the synthesis of extracellular matrix, and ultimately prevent the occurrence and development of atherosclerosis. Studies have proven that exogenous NO provider drugs can prevent and treat atherosclerosis by inhibiting the proliferation of vascular smooth muscle cells and the production of extracellular matrix and collagen. NO produced by activating eNOS can resist atherosclerosis by many effects of regulating vascular tone, lipid infiltration, inflammatory reaction, thrombosis, vascular remodeling and the like.

In this experiment, each tested compound can improve the dyslipidemia in ApoE gene-deleting mice, indicating that the tested compound has an inhibitory effect on the occurrence and development of atherosclerosis, and its mechanism may be related to the tested compound which promotes the expression of ApoA1 in vivo, increases the eNOS activity in vivo, and promotes the release of NO for vascular cells.

Experiment 7. Study on the Effect of the Test Compounds on C57 Mice and db/db Mice Experiment 1): Study on the Effect of the Tested Compounds on C57 Mice Experimental method: 60 eight-week-old C57BL/6 mice (level: SPF; gender: male; source: Shanghai SLAC Laboratory Animal Co., Ltd.) were selected. 2 of them were selected as the blank control. 12 mice were used as the positive drug control (isosorbide mononitrate). 12 mice were used as H101 administration group. The other 32 mice were randomly divided into 4 groups, 8 mice per group, which are H111 administration group, H116 administration group, H119 administration group, and H130 administration group, respectively. The tested compounds of the positive drug control group and each administration group were dissolved in DMSO and then PEG400 was added thereto. The mixture was shaken and mixed thoroughly. At last, 10% of HP-β-CD was added. The mixture was shaken and mixed thoroughly. The ratio of each solvent was DMSO: PEG400:10% of HP-β-CD=5:67.5:27.5. The administration groups were administered by oral gavage at the dose of 150 mg/kg. The positive drug control group was administered at the dose of 5 mg/kg. The mice in each group were sacrificed by inhaling excess $CO_2$ at 10 min, 30 min, 60 min, 120 min, 180 min, and 240 min after administration. The blood was collected into a 1.5 mL centrifuge tube, standing at room temperature for more than 30 min, and then centrifuged (3000 rpm, 10 min). The supernatant serum was aspirated, and stored at −80° C. for testing. After the blood was collected, the heart was cut with the thoracic aorta. Three parts of the heart were weighed and placed into cryovials, rapidly frozen in liquid nitrogen, and cryopreserved at −80° C. for testing. The aorta and aortic arch were weighed, rapidly frozen in liquid nitrogen, and cryopreserved at −80° C. for testing. The content of NO in the serum of C57BL/6 mice was determined by using the total NO test kit (Beyotime).

The experimental results are shown in FIG. 1.

Experimental conclusion: It can be seen from the experimental results that after the administration of the tested compounds to the C57 mice of each group, except the H130 administration group, the NO levels in the serum of all mice in the other groups increases to a certain extent, compared with the mice in the blank control group. After the administration of H111 and H119 compounds for 1 h, the NO level in the serum of the C57 mice increases and then the amount of the released NO decreased. After the administration of the positive drug and H101 compound for 2 h, the NO in the serum of the C57 mice was released to maximum level, and then the amount of the released NO gradually decreases.

Experiment 2): Study on the Effect of the Tested Compounds on db/db Mice

Experimental method: 25 eight-week-old db/db mice (strain: BKS.Cg-+Leprdb/+leprdb/JclSlac; grade: SPF; gender: male; source: Shanghai SLAC Laboratory Animal Co., Ltd.) were selected. 3 of them were selected as the blank administration control. 2 mice were used as the positive drug control (isosorbide mononitrate). The remaining 20 mice were randomly divided into 5 groups, 4 mice per group, which are H101 administration group, H111 administration group, H116 administration group, H119 administration group, and H130 administration group. The tested compounds of the positive drug control group and each administration group were dissolved in DMSO. Then PEG400 was added. The mixture was shaken and mixed thoroughly. At last, 10% of HP-β-CD was added. The mixture was shaken and mixed thoroughly. The ratio of each solvent was DMSO:PEG400:10% of HP-β-CD=5:67.5:27.5. The administration group was administered by oral gavage at the dose of 150 mg/kg. The positive drug control group was administered at the dose of 5 mg/kg. The mice in the H101 administration group were sacrificed at 2 h after the administration. The mice in the remaining administration groups were sacrificed at 1 h after the administration. The blood was collected respectively into 1.5 mL centrifuge tube, standing at room temperature for more than 30 min, and then centrifuged (3000 rpm, 10 min). The supernatant serum was aspirated, and stored at −80° C. for testing. After the blood was collected, the heart was cut with the thoracic aorta. Three parts of the heart were weighed and placed into cryovials, rapidly frozen in liquid nitrogen, and cryopreserved at −80° C. for testing. The aorta and aortic arch were weighed, rapidly frozen in liquid nitrogen, and cryopreserved at −80° C. for testing. The content of NO in the serum of the C57BL/6 mice was determined by a total NO test kit (Beyotime). The content of NOS in the heart of the mice was determined with an NOS test kit (Beyotime). The content of eNOS was calculated by the difference between the measured values before and after adding the eNOS inhibitor L-NAME (Beyotime).

Experimental result: changes of NO in the serum and the activity of eNOS in the heart of the db/db mice after administration are shown in Table 9.

Experimental conclusion: In the experiments on db/db mice, after the administration of the tested compounds, compared with the blank control mice, except the H130 administration group, eNOS in the heart and NO in the serum of the mice in the other tested compound administration groups increases at different levels.

The above experimental results indicate that the NO provider compounds provided by the inventor can promote releasing NO by blood vessels, and increase the activity of eNOS once entering a body.

TABLE 9

| Group | Heart eNOS (%) | Serum NO (%) |
|---|---|---|
| Blank Administration Group | 100 | 100 |
| Isosorbide Mononitrate | 169 | 136 |
| H101 Administration Group | 162 | 142 |
| H111 Administration Group | 165 | 154 |
| H116 Administration Group | 159 | 147 |
| H119 Administration Group | 156 | 152 |
| H130 Administration Group | 123 | 111 |

Experiment 8. Acute Toxicity Test of the Tested Compounds on Balb/c Mice

Compounds: H101, H111, and H118 were respectively dissolved in DMSO to prepare 500 μM of drug mother liquor. Appropriate amount of each tested compound was slowly diluted in PBS. The control group was injected with PBS (with the same concentration of DMSO).

Animals: Balb/c mice, 10 mice per group.

Method: The drugs were administered by intraperitoneal injection. The high dose group: 300 mg/kg/day; the low dose group: 150 mg/kg/day, administered once a day for 3 days. Changes of the animals were observed within 14 days.

Result: Compared with the mice in the control group, no body weight and behavioral abnormalities in the mice of the administration group were observed within 14 days from the date of administration, indicating that the above-mentioned concentrations of the tested compounds of the present invention were substantially non-toxic to mice.

The invention claimed is:

1. A compound of formula (II):

A-B    (II)

or a pharmaceutically acceptable salt or stereoisomer thereof,
wherein:

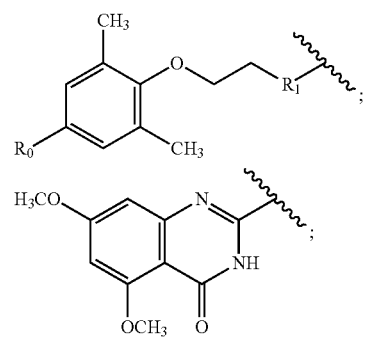

$R_1$ is —O—;
$R_2$ is H or $C_{1-4}$ alkyl;
$R_3$ is —CH—;
$R_4$ is $C_{1-3}$ alkyl;
$R_5$ is —O—;
T is $C_{1-5}$ alkylene;
$T_2$ is selected from the group consisting of $C_{1-6}$ alkyl and phenyl;
B is selected from the group consisting of:

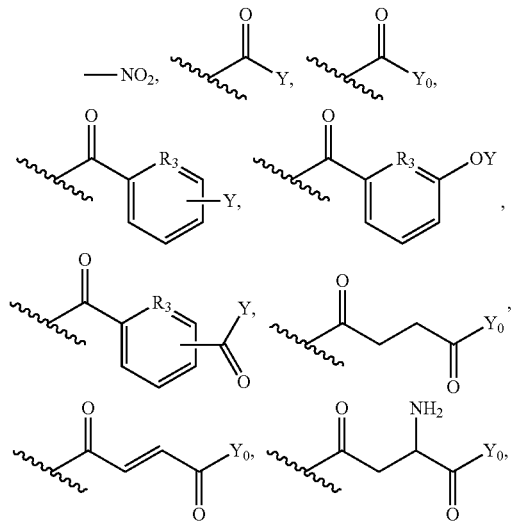

-continued
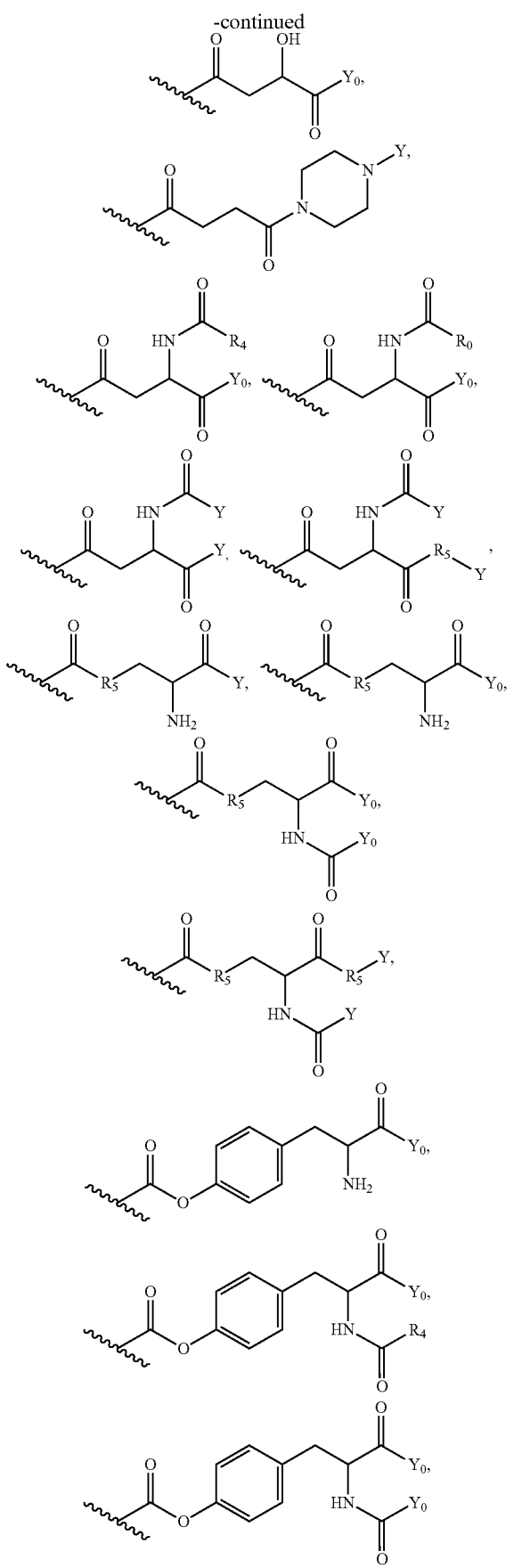
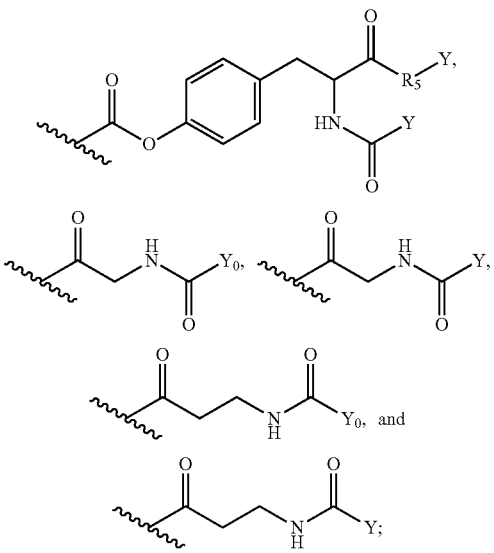
Y is selected from the group consisting of:
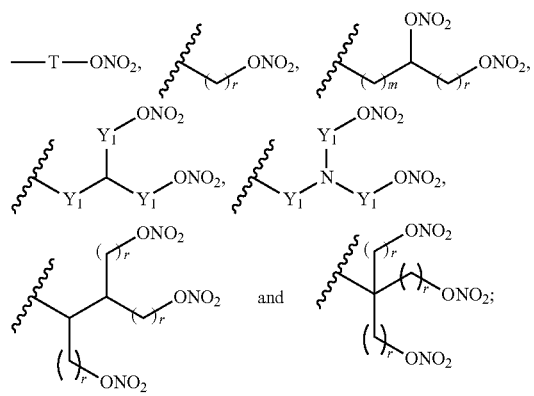
$Y_0$ is selected from the group consisting of:
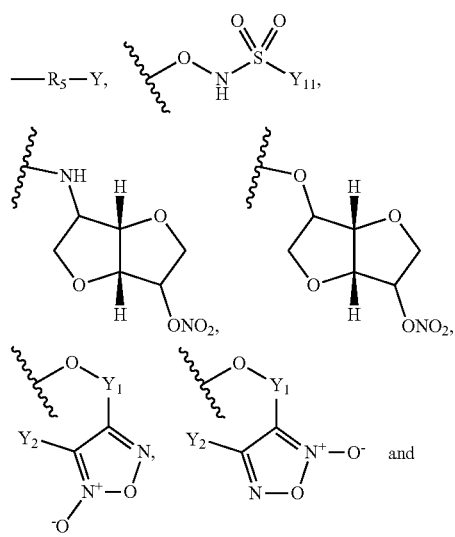

-continued

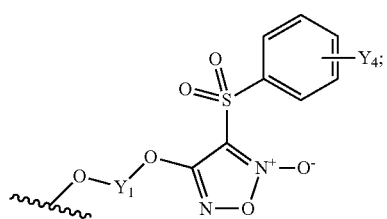

$Y_1$ is $C_{1-5}$ alkylene or $C_{1-5}$ alkylene substituted with one $T_2$;

$Y_2$ is selected from the group consisting of CN, $C_{1-6}$ alkyl, $CF_3$, $OC_{1-4}$ alkyl, $C_{1-4}$ alkyl-$ONO_2$, $S(O)_2$-phenyl and phenyl;

$Y_4$ is H;

$Y_{11}$ is selected from the group consisting of:

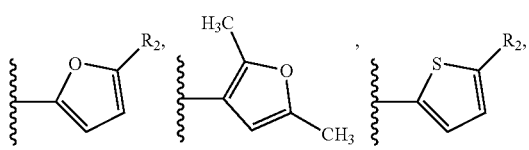

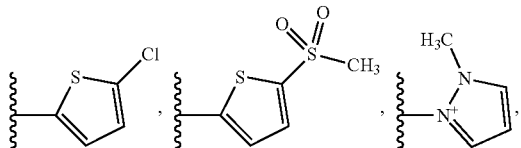

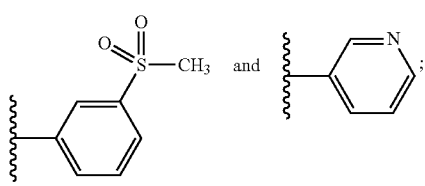

m is 0, 1, 2 or 3; and r is 1 or 2.

2. The compound according to claim 1, or a pharmaceutically acceptable salt or stereoisomer thereof, wherein:

T is $C_{1-4}$ alkylene;

$T_2$ is linear $C_{1-4}$ alkyl;

Y is selected from the group consisting of:

T-$ONO_2$,

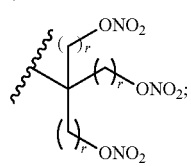

$Y_0$ is selected from the group consisting of:
—$R_5$—Y,

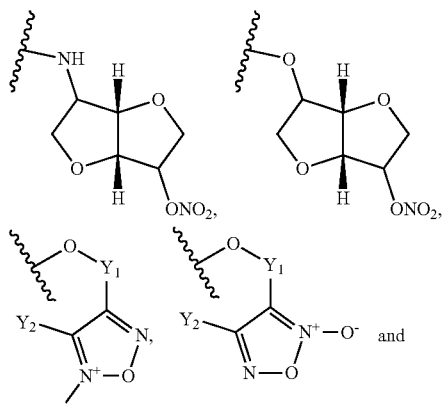

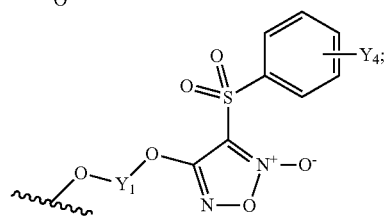

and $Y_2$ is selected from the group consisting of $C_{1-6}$ alkyl, $C_{1-4}$ alkyl-$ONO_2$, $S(O)_2$-phenyl and phenyl.

3. The compound according to claim 1, or a pharmaceutically acceptable salt or stereoisomer thereof, wherein:

B is selected from the group consisting of:

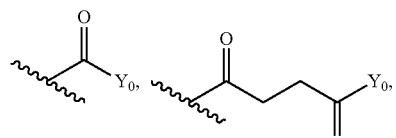

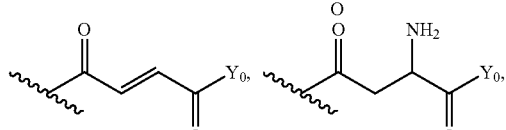

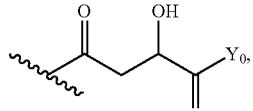

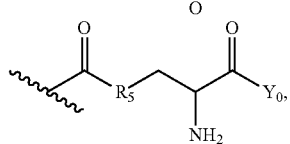

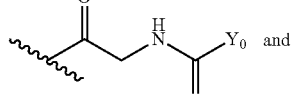

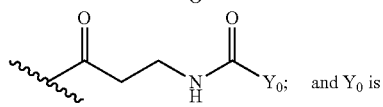

and $Y_0$ is

-continued

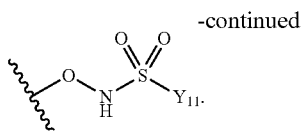

4. The compound according to claim 1, wherein the compound is selected from the group consisting of:

2-(4-(2-nitrooxy-ethoxy)-3,5-dimethylphenyl)-5,7-dimethoxyquinazolin-4(3H)-one;

2-[4-(5,7-dimethoxy-4-oxo-3,4-dihydro-quinazolin-2-yl)-2,6-dimethyl-phenoxy]-ethyl 3-nitrooxy methylbenzoate;

N-((2-(4-(5,7-dimethoxy-4-oxo-3,4-dihydroquinazolin-2-yl)-2,6-dimethylphenoxy)ethoxy)carbonyloxy)-5-methylthiophene-2-sulfonamide;

N-((2-(4-(5,7-dimethoxy-4-oxo-3,4-dihydroquinazolin-2-yl)-2,6-dimethylphenoxy)ethoxy)carbonyloxy)-5-methylfuran-2-sulfonamide;

2-[4-(5,7-dimethoxy-4-oxo-3,4-dihydro-quinazolin-2-yl)-2,6-dimethyl-phenoxy]-ethyl 3-(3-nitrooxy-propionyl)-benzoate;

2-[4-(5,7-dimethoxy-4-oxo-3,4-dihydro-quinazolin-2-yl)-2,6-dimethyl-phenoxy]-ethyl 3-(nitrooxy)-2,2-di((nitrooxy)methyl) propyl succinate;

2-[4-(5,7-dimethoxy-4-oxo-3,4-dihydro-quinazolin-2-yl)-2,6-dimethyl-phenoxy]-ethyl 3-(2,3-dinitrooxy-propoxy)-benzoate;

2-[4-(5,7-dimethoxy-4-oxo-3,4-dihydro-quinazolin-2-yl)-2,6-dimethyl-phenoxy]-ethyl 4,5-dinitrooxy-pentanoate;

2-[4-(5,7-dimethoxy-4-oxo-3,4-dihydro-quinazolin-2-yl)-2,6-dimethyl-phenoxy]-ethyl (4-nitrooxy-butylamido)-acetate;

2-nitrooxy-ethyl 2-amino-3-(4-{2-[4-(5,7-dimethoxy-4-oxo-3,4-dihydro-quinazolin-2-yl)-2,6-dimethyl-phenoxy]-ethoxycarbonyloxy}-phenyl)-propionate hydrochloride;

2-[4-(5,7-dimethoxy-4-oxo-3,4-dihydro-quinazolin-2-yl)-2,6-dimethyl-phenoxy]-ethyl 4-(2-oxo-3-nitrooxymethyl-1,2,5-oxadiazole-3-methyl)oxy-4-oxo-butyrate;

2-[4-(5,7-dimethoxy-4-oxo-3,4-dihydro-quinazolin-2-yl)-2,6-dimethyl-phenoxy]-ethyl 3-(6-nitrooxy-caproylamido)-propionate;

2-[4-(5,7-dimethoxy-4-oxo-3,4-dihydro-quinazolin-2-yl)-2,6-dimethyl-phenoxy]-ethyl (2-oxo-4-phenyl-furazan-3-yl)-methyl 2-hydroxy succinate;

4-(2-(((2-(4-(5,7-dimethoxy-4-oxo-3,4-dihydro-quinazolin-2-yl)-2,6-dimethyl-phenoxy)ethoxy)carbonyl)oxy)ethoxy)-3-(phenylsulfonyl)-2-oxo-furazan;

2-[4-(5,7-dimethoxy-4-oxo-3,4-dihydro-quinazolin-2-yl)-2,6-dimethyl-phenoxy]-ethyl (E)-4-((furan-2-sulfonylamino)oxy)-4-oxo-2-butenoate;

2-[4-(5,7-dimethoxy-4-oxo-3,4-dihydro-quinazolin-2-yl)-2,6-dimethyl-phenoxy]-ethyl 4-(((3-(methylsulfonyl)phenyl)sulfonamido)oxy)-4-oxo-butyrate;

2-[4-(5,7-dimethoxy-4-oxo-3,4-dihydro-quinazolin-2-yl)-2,6-dimethyl-phenoxy]-ethyl 4-[4-(2-(nitrooxy)ethyl)-piperazin-1-yl]-4-oxo-butyrate;

1-(2,3-dinitrooxy-propyl) 4-{2-[4-(5,7-dimethoxy-4-oxo-3,4-dihydro-quinazolin-2-yl)-2,6-dimethyl-phenoxy]-ethyl}2-amino-succinate hydrochloride;

2-[4-(5,7-dimethoxy-4-oxo-3,4-dihydro-quinazolin-2-yl)-2,6-dimethyl-phenoxy]-ethyl (6-nitrooxy-hexahydrofuro [3,2-b] furan-3-yl)-carbonate;

2-[4-(5,7-dimethoxy-4-oxo-3,4-dihydro-quinazolin-2-yl)-2,6-dimethyl-phenoxy]-ethyl (6-nitrooxy-hexahydrofuro [3,2-b] furan-3-yl)-carbamate;

2-[4-(5,7-dimethoxy-4-oxo-3,4-dihydro-quinazolin-2-yl)-2,6-dimethyl-phenoxy]-ethyl 4-(((5-chlorothiophene)-2-sulfonylamino)oxy)-4-oxo-butyrate;

2-(N-(((2-(4-(5,7-dimethoxy-4-oxo-3,4-dihydro-quinazolin-2-yl)-2,6-dimethyl-phenoxy]-ethoxy)carbonyl)oxy)sulfamoyl)-1-methyl-1H-pyridine 1-2-onium salt;

3,4-(dinitrooxy) butyl 2-acetyl amino-3-(4-(((2-(4-(5,7-dimethoxy-4-oxo-3,4-dihydro-quinazolin-2-yl)-2,6-dimethyl-phenoxy]-ethoxy)carbonyl)oxy)phenyl) propionate;

3-(nitrooxy)-2,2-di(nitrooxymethyl) propyl 4-(2-[4-(5,7-dimethoxy-4-oxo-3,4-dihydro-quinazolin-2-yl)-2,6-dimethyl-phenoxy]butyl)-4-oxo-2-acetylamino-butyrate; and 2-nitrooxyethyl 4-(2-[4-(5,7-dimethoxy-4-oxo-3,4-dihydroquinazolin-2-yl)-2,6-dimethylphenoxy]butoxy)-4-oxo-2-(2-(nitrooxy)acetylamino)butyrate, or a pharmaceutically acceptable salt or stereoisomer thereof.

5. A pharmaceutical composition comprising a therapeutically effective amount of a compound according to claim 1, or a pharmaceutically acceptable salt or stereoisomer thereof, and one or more pharmaceutically acceptable carriers and/or diluents.

6. A method for increasing apolipoprotein A-1 levels in a subject or releasing nitric oxide in a subject, comprising administering to a subject in need thereof a therapeutically effective amount of a compound according to claim 1, or a pharmaceutically acceptable salt or stereoisomer thereof, or a pharmaceutical composition according to claim 5.

7. The method according to claim 6, wherein the subject has a disease selected from the group consisting of a cardiovascular disease, a cerebrovascular disease and a metabolic disease.

8. The method according to claim 7, wherein the cardiovascular disease or cerebrovascular disease is atherosclerosis.

9. The method according to claim 7, wherein the metabolic disease is selected from the group consisting of type 2 diabetes, diabetic dyslipidemia, diabetic macular edema, diabetic retinopathy, diabetic nephropathy, diabetic neuropathy, appetite regulation and obesity.

* * * * *

UNITED STATES PATENT AND TRADEMARK OFFICE
CERTIFICATE OF CORRECTION

PATENT NO. : 10,456,405 B2  
APPLICATION NO. : 15/756476  
DATED : October 29, 2019  
INVENTOR(S) : Jian Ge et al.

Page 1 of 2

It is certified that error appears in the above-identified patent and that said Letters Patent is hereby corrected as shown below:

In the Claims

In Column 62, Claim 1, Line 25, please delete:

"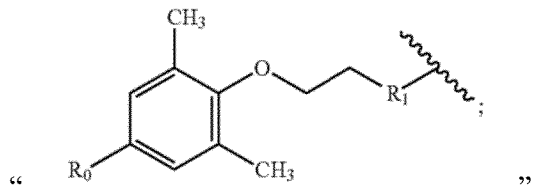"

And replace with:

A is 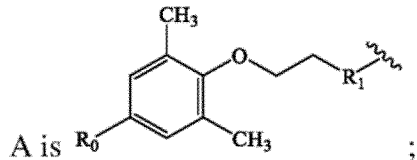 ;

In Column 62, Claim 1, Line 30, please delete:

"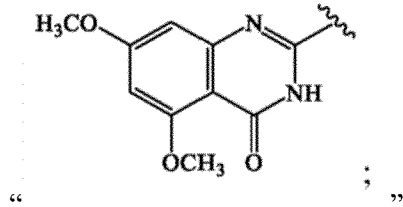"

And replace with:

Signed and Sealed this  
Fifth Day of May, 2020

Andrei Iancu  
*Director of the United States Patent and Trademark Office*

CERTIFICATE OF CORRECTION (continued)
U.S. Pat. No. 10,456,405 B2

$R_0$ is 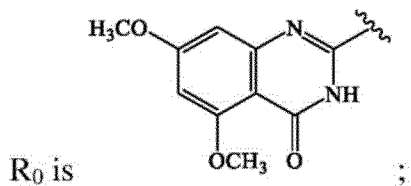 ;

In Column 65, Claim 2, Line 53, please delete:
"T-ONO$_2$"

And replace with:
-T-ONO$_2$